US011925465B2

(12) United States Patent
Laing et al.

(10) Patent No.: US 11,925,465 B2
(45) Date of Patent: Mar. 12, 2024

(54) UROFLOWMETER

(71) Applicant: ClearTrac Technologies, LLC, Elizabethton, TN (US)

(72) Inventors: Brent Laing, Greenwood Village, CO (US); John Green, Elizabethton, TN (US); Paul R. Johnson, Boulder, CO (US); Robert John Smith, Louisville, CO (US); Robert Edwin Schneider, Erie, CO (US); Magnus Hargis, Hudson, CO (US); Elise Geolat Edson, Boulder, CO (US); Elizabeth A. O'Brien, Louisville, CO (US); Joseph L. Kapushion, Westminster, CO (US)

(73) Assignee: ClearTrac Technologies, LLC, Elizabethton, TN (US)

( * ) Notice: Subject to any disclaimer, the term of this patent is extended or adjusted under 35 U.S.C. 154(b) by 315 days.

(21) Appl. No.: 16/297,192

(22) Filed: Mar. 8, 2019

(65) Prior Publication Data

US 2019/0365307 A1 Dec. 5, 2019

Related U.S. Application Data

(60) Provisional application No. 62/679,582, filed on Jun. 1, 2018.

(51) Int. Cl.
A61B 5/20 (2006.01)
A61B 5/00 (2006.01)
(Continued)

(52) U.S. Cl.
CPC .............. A61B 5/208 (2013.01); A61B 5/205 (2013.01); A61B 10/007 (2013.01);
(Continued)

(58) Field of Classification Search
CPC ....... A61B 5/0059; A61B 5/204; A61B 5/205; A61B 5/208; A61B 10/007;
(Continued)

(56) References Cited

U.S. PATENT DOCUMENTS 2,648,981 A 8/1953 Drake
3,172,130 A 3/1965 Lange
(Continued)

FOREIGN PATENT DOCUMENTS

CN 2221776 Y 3/1996
CN 105769223 A 7/2016
(Continued)

OTHER PUBLICATIONS

Do It Yourself, "Urinal Repair: Troubleshoot Urinal Plumbing Problems", https://web.archive.org/web/20-171015111849/http://www.doityourself.com/urinal-repair-troubleshoot-urinal-plumbing-problems; accessed on May 13, 2019, published on Oct. 15, 2017, 3 pages.

(Continued)

Primary Examiner — May A Abouelela
Assistant Examiner — Anna Roberts
(74) Attorney, Agent, or Firm — Dorsey & Whitney LLP

(57) ABSTRACT

Uroflowmeters and methods for processing data generated therefrom are disclosed. In one aspect, the uroflowmeter is a handheld device. The uroflowmeter includes a handle, a flow chamber coupled to the handle, and a sensor associated with the flow chamber that detects a parameter of urine received in the flow chamber. The uroflowmeter may include both reusable and disposable components. As a uroflowmeter it can identify and record data corresponding to the rate of flow over the measured duration of a void of urine, but may also timestamp the voiding act and communicate the data to an external data collection center for additional (Continued)

analysis and incorporation into a comprehensive voiding report or voiding diary.

18 Claims, 34 Drawing Sheets

(51) Int. Cl.
- A61B 10/00 (2006.01)
- B23Q 1/54 (2006.01)
- G01D 21/00 (2006.01)
- G01F 23/26 (2022.01)
- G01M 99/00 (2011.01)
- G06F 9/54 (2006.01)

(52) U.S. Cl.
CPC ........... *B23Q 1/5475* (2013.01); *G01D 21/00* (2013.01); *G01F 23/26* (2013.01); *G01M 99/00* (2013.01); *G06F 9/542* (2013.01); *A61B 5/0059* (2013.01); *A61B 5/204* (2013.01); *A61B 5/7275* (2013.01); *A61B 2562/0223* (2013.01)

(58) Field of Classification Search
CPC .... A61B 2560/0223; A61B 2562/0223; G01F 23/26; G01F 25/0007; G06F 9/542; G01G 17/04; G01N 2035/1025
See application file for complete search history.

(56) References Cited

U.S. PATENT DOCUMENTS

| | | |
|---|---|---|
| 3,219,276 A | 11/1965 | Norris |
| 3,859,854 A | 1/1975 | Dye et al. |
| 3,871,230 A | 3/1975 | Dye et al. |
| 3,884,072 A | 5/1975 | Cheng |
| 3,929,412 A | 12/1975 | Villari |
| 3,931,972 A | 1/1976 | Fabian |
| 4,051,431 A | 9/1977 | Wurster |
| 4,085,616 A | 4/1978 | Patel et al. |
| 4,131,016 A | 12/1978 | Layton |
| 4,238,448 A | 12/1980 | Layton et al. |
| 4,343,316 A | 8/1982 | Jespersen |
| 4,554,687 A | 11/1985 | Carter et al. |
| 4,569,090 A * | 2/1986 | Muller ................. A61B 10/007 4/144.2 |
| 4,576,076 A | 3/1986 | Pyle |
| 4,619,273 A | 10/1986 | Iosif |
| D296,360 S | 6/1988 | Oelberg |
| 4,832,046 A | 5/1989 | Parrish |
| 4,891,993 A | 1/1990 | Barker |
| 5,046,510 A | 9/1991 | Ams et al. |
| 5,062,304 A | 11/1991 | Van et al. |
| 5,176,148 A | 1/1993 | Wiest et al. |
| 5,186,394 A | 2/1993 | Tsuji |
| D340,768 S | 10/1993 | Jabour |
| 5,377,101 A | 12/1994 | Rollema |
| 5,422,076 A | 6/1995 | Jones |
| D378,129 S | 2/1997 | Wexler et al. |
| 5,794,541 A | 8/1998 | Hirose |
| D422,851 S | 4/2000 | Joergensen |
| D425,365 S | 5/2000 | Chien |
| D436,801 S | 1/2001 | Wonderley |
| 6,398,742 B1 | 6/2002 | Kim |
| D460,328 S | 7/2002 | De et al. |
| D461,105 S | 8/2002 | Law |
| 6,651,259 B1 | 11/2003 | Hartman et al. |
| D492,995 S | 7/2004 | Rue et al. |
| D494,279 S | 8/2004 | Cogan et al. |
| 6,889,563 B2 | 5/2005 | Tomita et al. |
| 6,904,809 B1 | 6/2005 | Aundal |
| 6,931,943 B1 | 8/2005 | Aundal |
| D545,621 S | 7/2007 | Hood |
| D551,032 S | 9/2007 | Lion et al. |
| D552,431 S | 10/2007 | Chou |
| D572,089 S | 7/2008 | Teys et al. |
| 7,416,542 B2 | 8/2008 | Aundal |
| D598,251 S | 8/2009 | Ikoma et al. |
| 7,606,617 B2 | 10/2009 | Wariar |
| 7,739,907 B2 | 6/2010 | Boiarski |
| D619,246 S | 7/2010 | Hazeres |
| 7,762,596 B1 | 7/2010 | Gaydos et al. |
| 7,819,020 B2 | 10/2010 | Jacobi et al. |
| 7,892,217 B2 | 2/2011 | Boiarski |
| 8,141,420 B2 | 3/2012 | Hirao |
| D659,558 S | 5/2012 | Johnson et al. |
| 8,231,552 B2 | 7/2012 | Shahar et al. |
| 8,424,376 B2 | 4/2013 | Boiarski |
| D681,392 S | 5/2013 | Dichraff et al. |
| D688,370 S | 8/2013 | Desai |
| 8,500,705 B2 | 8/2013 | Kim |
| 8,544,341 B2 | 10/2013 | Grumbles et al. |
| 8,574,492 B2 | 11/2013 | Morita et al. |
| D709,185 S | 7/2014 | Queiroli |
| 8,813,551 B2 | 8/2014 | Boiarski |
| 9,021,878 B2 | 5/2015 | Grinstein et al. |
| D736,043 S | 8/2015 | Lee et al. |
| D770,613 S | 11/2016 | Roberts |
| 9,642,737 B2 | 5/2017 | Seres et al. |
| 9,775,556 B2 | 10/2017 | Dimino et al. |
| 9,885,598 B2 * | 2/2018 | Tesar ..................... G01F 23/38 |
| D823,652 S | 7/2018 | Dooley et al. |
| 10,034,659 B2 | 7/2018 | Siller Gonzalez et al. |
| D842,985 S | 3/2019 | Heckerman |
| 10,219,733 B2 | 3/2019 | Shimokawa et al. |
| D862,999 S | 10/2019 | Riedel et al. |
| D871,137 S | 12/2019 | Brouillac |
| D873,995 S | 1/2020 | Laing et al. |
| D876,183 S | 2/2020 | Yee |
| 10,578,196 B2 | 3/2020 | Haremaki et al. |
| D889,918 S | 7/2020 | Hubert |
| D893,947 S | 8/2020 | Pulk |
| D914,204 S | 3/2021 | Roberts |
| D919,798 S | 5/2021 | Laing et al. |
| D920,502 S | 5/2021 | Laing et al. |
| 11,029,239 B2 | 6/2021 | Littley et al. |
| D932,632 S | 10/2021 | Laing et al. |
| D932,633 S | 10/2021 | Laing et al. |
| D932,648 S | 10/2021 | Laing et al. |
| D933,238 S | 10/2021 | Laing et al. |
| D933,239 S | 10/2021 | Laing et al. |
| D933,240 S | 10/2021 | Laing et al. |
| D933,241 S | 10/2021 | Liang et al. |
| D978,358 S | 2/2023 | Laing et al. |
| D979,076 S | 2/2023 | Laing et al. |
| 2005/0261605 A1 | 11/2005 | Shemer et al. |
| 2008/0312556 A1 | 12/2008 | Dijkman |
| 2008/0312557 A1 | 12/2008 | Cho et al. |
| 2011/0000309 A1 | 1/2011 | Griffiths et al. |
| 2012/0109008 A1 | 5/2012 | Charlez et al. |
| 2013/0143252 A1 * | 6/2013 | Knight ..................... C12Q 1/04 435/25 |
| 2016/0029942 A1 | 2/2016 | Paulsen et al. |
| 2016/0051176 A1 | 2/2016 | Ramos et al. |
| 2017/0020433 A1 * | 1/2017 | Hotaling .............. A61B 10/007 |
| 2017/0086728 A1 | 3/2017 | Hidas |
| 2017/0105670 A1 | 4/2017 | Holt et al. |
| 2017/0135622 A1 | 5/2017 | Shimokawa et al. |
| 2017/0307423 A1 | 10/2017 | Pahwa et al. |
| 2018/0085008 A1 | 3/2018 | Hall et al. |
| 2018/0303465 A1 | 10/2018 | Lyon et al. |
| 2019/0039201 A1 | 2/2019 | Müller |
| 2019/0365306 A1 | 12/2019 | Laing et al. |
| 2019/0365307 A1 | 12/2019 | Laing et al. |
| 2019/0365308 A1 | 12/2019 | Laing et al. |
| 2020/0209044 A1 * | 7/2020 | Holt ....................... A61B 5/204 |
| 2020/0268303 A1 * | 8/2020 | Oliva ................. A61B 5/0022 |

FOREIGN PATENT DOCUMENTS

| | | | |
|---|---|---|---|
| CN | 205494247 U | * | 8/2016 |
| CN | 106037766 A | | 10/2016 |
| DE | 3007855 A1 | | 9/1981 |

(56) References Cited

FOREIGN PATENT DOCUMENTS

| | | | |
|---|---|---|---|
| DE | 19733630 A1 | 2/1999 | |
| DE | 102014008760 A1 | 1/2015 | |
| EM | 005840378-0001 | 11/2018 | |
| EM | 005840378-0002 | 11/2018 | |
| EM | 005840378-0003 | 11/2018 | |
| EM | 005840436-0001 | 11/2018 | |
| EM | 005840436-0002 | 11/2018 | |
| EM | 005840436-0003 | 11/2018 | |
| EM | 006821633-001 | 9/2019 | |
| EM | 006821633-0002 | 9/2019 | |
| EM | 006821633-0003 | 9/2019 | |
| EM | 006821633-0004 | 9/2019 | |
| EP | 2303124 B1 | 8/2012 | |
| EP | 2741671 B1 | 1/2016 | |
| EP | 2716219 B1 | 3/2017 | |
| EP | 2564778 B1 | 4/2018 | |
| JP | 3729732 B2 | 10/2005 | |
| KR | 20110030826 A | 3/2011 | |
| KR | 20180036022 A * | 4/2018 | |
| RU | 2034516 C1 | 5/1995 | |
| RU | 2071724 C1 | 1/1997 | |
| RU | 2643110 C1 | 1/2018 | |
| WO | 9925246 A1 | 5/1999 | |
| WO | WO-9925246 A1 * | 5/1999 | ............. A61B 5/208 |
| WO | 2009035599 A1 | 3/2009 | |
| WO | 2009142508 A1 | 11/2009 | |
| WO | 2014141234 A1 | 9/2014 | |
| WO | 2016056571 A1 | 4/2016 | |
| WO | 2017036952 A1 | 3/2017 | |
| WO | 2017149272 A1 | 9/2017 | |
| WO | 2018036664 A1 | 3/2018 | |
| WO | 2018051244 A1 | 3/2018 | |

OTHER PUBLICATIONS

PCT, "International Search Report and Written Opinion", Application No. PCT/US19/21421, dated May 31, 2019, 16 pages.

Drive Medical. "Drive Medical Folding Steel Bedside Commode, Grey." obtained Nov. 12, 2018 from <https://www.amazon.com/Drive-Medical-Folding-Bedside-Commode/dp/B001HP7AQE/ref=sr_1_3?s=industrial&ie=UTF8&qid=1539732631&sr=1-3&keywords=commode>, 8 pages.

Specimen Collection Unit. "Specimen Collection Unit, QTY of 1." obtained Nov. 12, 2018 from <https://www.amazon.com/Specimen-Collection-Unit-QTY-1/dp/B002ZUCVP0#feature-bullets-btf>, 6 pages.

Bestmedical. "Uroflowmeter: Portable & wireless." obtained Nov. 12, 2018 from <http://www.best-medical.nl/uroflowmeter/>, 6 pages, Jan. 1, 2016.

MDTI. "Uflow meter Male Urine Peak Flow Device." obtained Nov. 12, 2018 from <https://www.mdti.co.uk/uflow->, 2 pages, Jan. 1, 2017.

Albyn Medical Product Detail. "SmartFlow: SmartFlow brings together high specifications and ease-of-use." Obtained Nov. 12, 2018 from <http://www.albynmedical.com/products/ProductDetail.aspx?ID=8>, 2 pages, Jan. 1, 2018.

Laborie: "Uroflometry: Uroflowmeters designed for practical, every-day studies, available in a range of configurations to meet different demands." obtained Nov. 12, 2018 from <https://www.laborie.com/category/urology-urogynecology/uroflowmetry/>, 6 pages, Jan. 1, 2018.

Minze Health. "Homeflow." obtained Nov. 12, 2018 from <https://minzehealth.com/products/homeflow/>, 8 pages, Jan. 1, 2018.

Chun, Kwonsoo et al., Kwonsoo, Chun et al. "Noninvasive Medical Tools for Evaluating Voiding Pattern in Real Life." International Neurology Journal, 2017, S10-16, Jan. 1, 2017.

"International Search Report and Written Opinion", Application No. PCT/US2019/021292, dated May 8, 2019, 11 pages.

Extended European Search Report dated Feb. 3, 2022 in connection with European Patent Application No. 19812560.1, 8 pages.

* cited by examiner

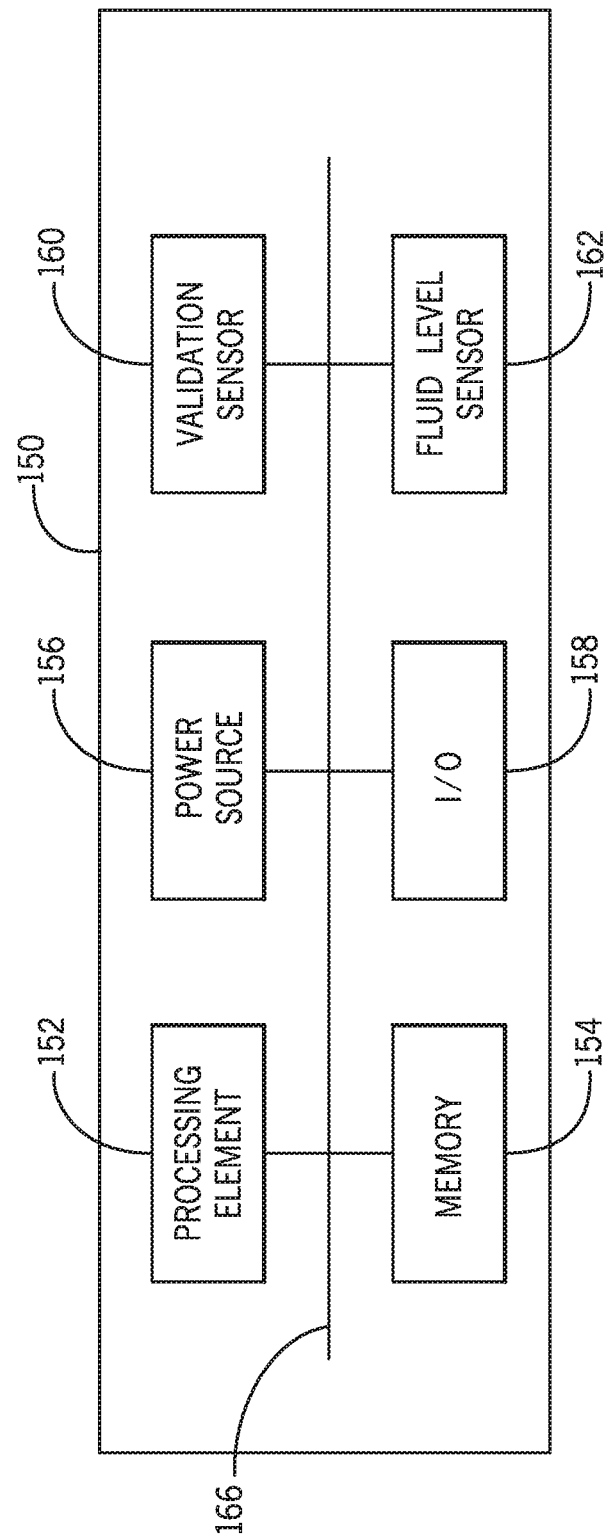

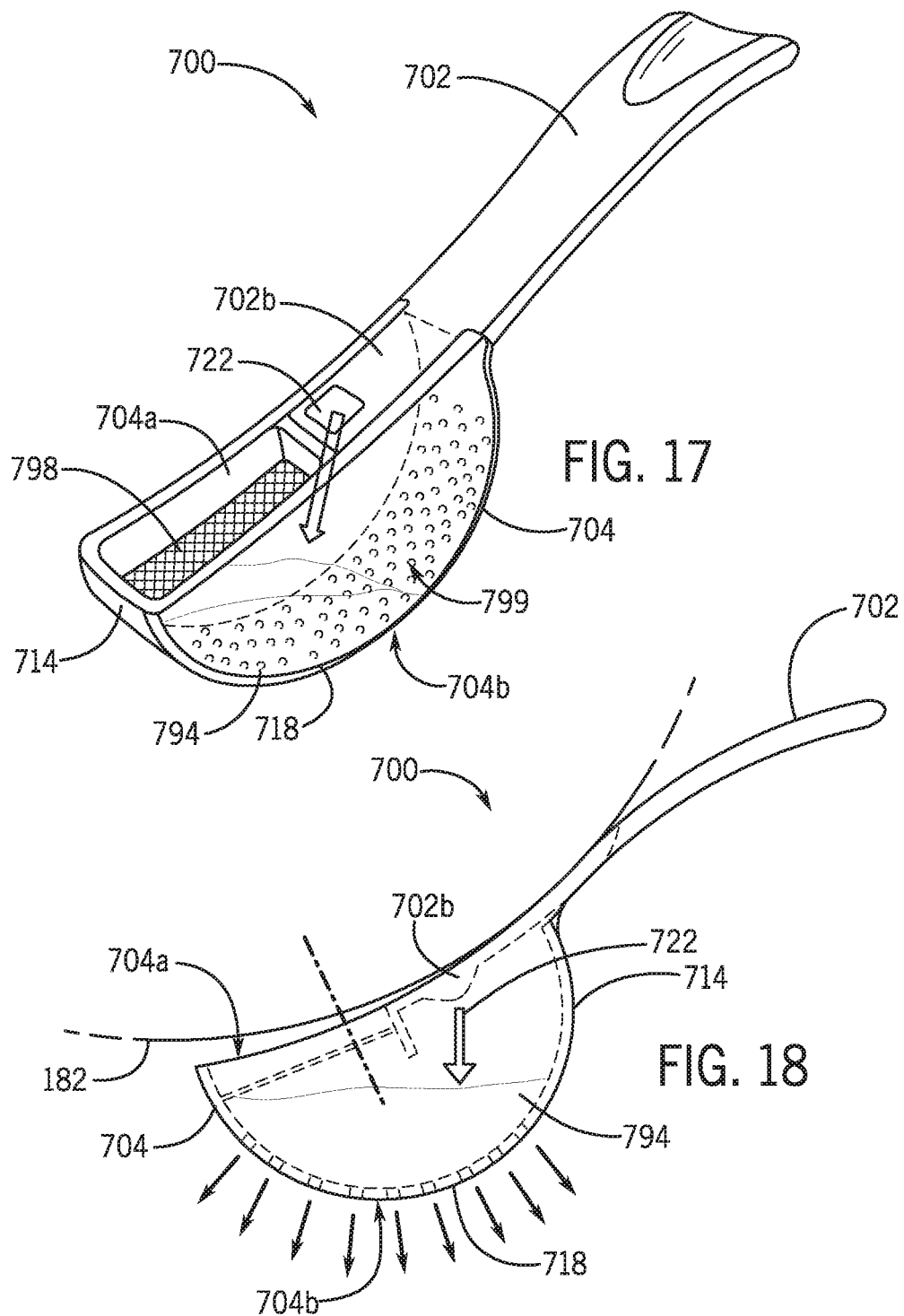

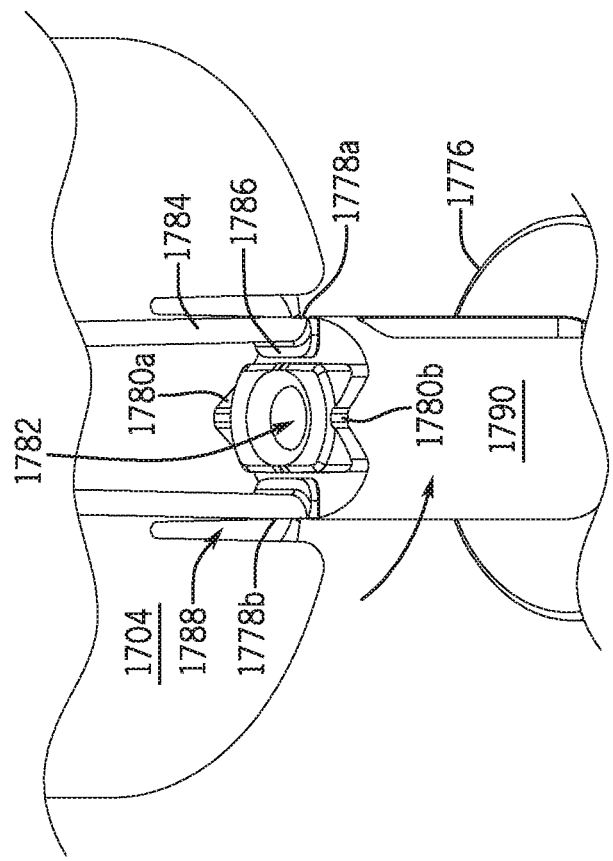
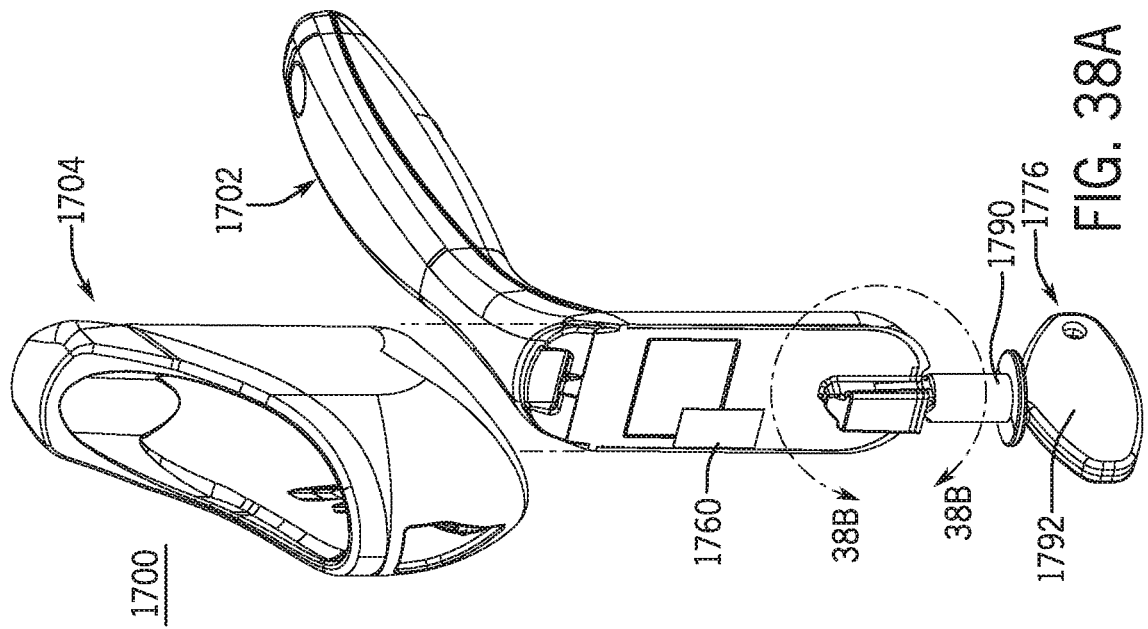
FIG. 38B
FIG. 38A

UROFLOWMETER

CROSS REFERENCE TO RELATED APPLICATIONS

This application claims the benefit of priority to U.S. Application No. 62/679,582, filed 1 Jun. 2018, which is hereby incorporated by reference in its entirety.

This application is related to U.S. patent application Ser. No. 16/296,647, now U.S. Pat. No. 11,534,093, filed 8 Mar. 2019 and titled, "Testing Device for a Uroflowmeter"; and U.S. patent application Ser. No. 16/297,417, now U.S. Pat. No. 11393,436, filed 8 Mar. 2019 and titled "Urinary Event Detection, Tracking and Analysis", the entireties of which are incorporated herein by reference for all purposes.

TECHNICAL FIELD

The technology described herein relates generally to uroflowmeters and methods for processing data generated therefrom.

BACKGROUND

Urine flow rate or urinary flow rate is the volumetric flow rate of urine during urination. That is, it is a measure of the quantity of urine excreted in a specified period of time and the periodic change in rate of urine flow during that time. Urinary flow rate is measured with uroflowmetry, a type of flowmetry device. For example, a uroflowmeter is a device for recording rates of urine flow over the time of a completed void.

Uroflowmeters generally are used to quantitate obstruction to urine flowing from the bladder. For example, a uroflowmeter can be used by a patient to quantify their urine flow rate, and this data can be used with other relevant data (such as the amount of time elapsed and fluid consumed since the patient's last urination or "void") to determine whether urine flow from the bladder is being impeded or obstructed. A voiding diary is the serial collection of data from each and every patient void over a defined period of time, such as twenty-four to seventy-two hours, in order to define the voiding behavior/misbehavior of that person's bladder. The urination data and assessment can be used by a medical practitioner to develop a treatment plan for the patient and to objectively quantify responses to therapy.

Related to traditional in-office uroflowmeters, patients may be asked to record void information in a voiding diary, such as: urgency, frequency, or volume of urine, of void events over a prescribed period of time. Patients may record voiding volume by voiding into a voiding measurement bowl placed over a toilet. Despite the availability of uroflowmeters, patients tend to not use these devices for various reasons, such as lack of portability and difficulty in consistently keeping a handwritten record of urination and other related data. Patients are reluctant to carry the voiding measurement bowl and paper diary with them because the bowl is large, indiscrete, and inconvenient. Due to the lack of portability, there are often voids missing from the diary. Additionally, often there is a delay between a patient completing a void and filling out the diary, which results in erroneous information being recorded or missing information. Finally, there is potential for delay in submitting a paper voiding diary back to the doctor's office for transcription into an electronic form. Handwriting may be illegible, or worse, the entire diary could be lost. These shortcomings result in delays and reduction in the quality of patient care.

Costly, non-portable devices, generally housed in physician's offices, fail to allow for optimal timing of the opportunity to empty a naturally full bladder, and producing errant results. There is a need for a uroflowmeter that remedies one or more problems of existing uroflowmeters, or at least provide an alternative thereto.

SUMMARY

The present disclosure generally relates to uroflowmeters and methods for processing data generated therefrom.

A uroflowmeter is disclosed herein. The uroflowmeter includes a handle, a flow chamber coupled to the handle, and a sensor associated with the flow chamber for detecting a parameter of urine received in the flow chamber. Sample parameters include, but are not limited to, urine flow rate, duration, void volume, and so on. The uroflowmeter may further include a funnel coupled to the flow chamber. Optionally, the funnel is removably coupled to the flow chamber and/or the flow chamber is removably coupled to the handle. In some aspects, the flow chamber defines an inlet for receiving urine from a patient and an outlet for outflow of the urine from the flow chamber. The outlet may be a V-shaped, T-shaped, or triangular slot. Optionally, electronics may be received or housed in the handle. In some aspects, a magnet is positioned adjacent to the sensor. In some aspects, the sensor detects an angular orientation of the magnet assembly to determine a fluid level of the urine in the flow chamber. In some aspects, a light emitting diode ("LED") is integrated with the elongated handle. The LED indicates an orientation of the uroflowmeter corresponding to a target condition, such as a target orientation. In some aspects, a funnel and a float are positioned between a side wall of the flow chamber and a side wall of the funnel. Optionally, the magnet is coupled to the float such that movement of the float causes rotation of the magnet. In some aspects, the float is pivotable about a pivot axis, and the magnet is axially aligned with the pivot axis. In some aspects, the parameter comprises a fluid level of the urine in the flow chamber, and/or the parameter comprises a flow rate of the urine entering and/or exiting the flow chamber. In some aspects, the uroflowmeter includes an orientation sensor that detects the orientation of the uroflowmeter. In some aspects, the uroflowmeter automatically powers on depending on the orientation of the uroflowmeter. In some aspects, the uroflowmeter further includes an accelerometer. In some aspects, the uroflowmeter further includes a capacitive sensor, wherein the accelerometer and the capacitive sensor are used to automatically power on the uroflowmeter. In some aspects, the handle is reusable. In some aspects, at least one of the flow chamber and the funnel are disposable and/or single patient use. In some aspects, the uroflowmeter is handheld. In some aspects, the uroflowmeter is not mounted to a toilet bowl, seat, or rim.

A method of using a uroflowmeter is disclosed herein. The method includes receiving a urine stream through an inlet of a flow chamber, measuring a fluid level of urine in the flow chamber via a sensor, and flowing the urine out of the flow chamber via an outlet of the flow chamber. The method may further include removing a disposable funnel from engagement with the flow chamber. The method may further include automatically powering on the uroflowmeter in response to positioning the uroflowmeter in an orientation suitable for receiving the urine stream.

A method of processing data from a uroflowmeter is disclosed. The method includes providing a uroflowmeter in communication with a voiding diary system, measuring urine flow rate, volume, and/or duration data obtained by the uroflowmeter, transmitting the urine flow rate, duration data, and timestamp to the voiding diary system, analyzing the urine flow rate data, and generating a graphical output of the urine flow rate, duration, volume, and timestamp data to develop a treatment plan. Optionally, the method may further include providing additional data including at least one of data related to total volume of urine output, fluid intake, bladder leaks, bedtime, and awake time.

A uroflowmeter is disclosed herein. The uroflowmeter includes a flow chamber receiving a flow of urine. The uroflowmeter further includes a magnet associated with the flow chamber and moves in response to the flow of urine. The uroflowmeter further includes a sensor adjacent the magnet detecting a movement of the magnet. A float may be included within the flow chamber that is positionable according to a fill level of urine within the flow chamber. An arm may connect the float and the magnet, and thus as the float rises due to a fill level of urine within the flow chamber, the magnet may rotate, such as about a pivot axis. The sensor further detects a change in an angular position of the magnet, which may in turn, be associated with the fill level. The uroflowmeter optionally includes a cantilevered handle extending away from the flow chamber and a funnel directs the flow of urine into a reservoir space of the flow chamber. The funnel can produce a smooth flow of urine into the flow chamber. The flow chamber can define an inlet which receives the flow of urine and an outlet evacuates urine from the flow chamber at a predetermined rate. The outlet can be defined by a T-shaped slot. In this regard, the uroflowmeter can further include electronics that determine a fill volume of the flow chamber using the movement of the magnet and/or determine a rate of the flow of urine using the movement of the magnet and the predetermined rate of the urine evacuated from the flow chamber. In order to facilitate anatomic positioning of the uroflowmeter, the flow chamber has a width, a length that is greater than the width, and a height that is greater than the length.

A uroflowmeter is disclosed herein. The uroflowmeter includes a flow chamber defining a reservoir space that has an inlet that receives a flow of urine and an outlet, separated from the inlet, that empties the reservoir space. The uroflowmeter further includes a funnel at least partially received within the inlet and having one or more contoured surfaces. A side wall of the funnel and a side wall of the flow chamber may define an annular space. The uroflowmeter further includes electronics associated with the flow chamber responsive to the flow of urine. The electronics can include a sensor associated with the flow chamber that detects a parameter of urine received in the chamber, such as a fill level of urine within the chamber. To facilitate the foregoing, the uroflowmeter can further include a magnet positionally responsive to the flow of urine, and the sensor is further detects a movement of the magnet. To facilitate proper anatomical positioning, the flow chamber includes contoured side walls and/or has a width, a height that is greater than the width, and a length that is greater than the height. The outlet of the uroflowmeter can empty urine from the flow chamber at a predetermined rate and may be defined by a triangular-shaped slot, such as a triangular-shaped slot that empties the reservoir space at an increasing rate as the reservoir space fills with urine. Optionally, the uroflowmeter includes a detachable handle. This detachable handle can house at least some of the electronics.

In some embodiments, these features and components may be included in a uroflowmeter to the exclusion of some, or all, of the others. In some embodiments, any or all of these features and components may be combined together without limitation.

BRIEF DESCRIPTION OF THE DRAWINGS

FIG. 6A is a simplified block diagram of a computing device or system associated with the uroflowmeter of FIG. 1 in accordance with various embodiments of the present disclosure.

FIG. 17 is a perspective view of an alternative uroflowmeter in accordance with various embodiments of the present disclosure.

FIG. 18 is a longitudinal sectional view of the uroflowmeter of FIG. 17 in accordance with various embodiments of the present disclosure.

FIG. 38A is a partially exploded view of the uroflowmeter of FIG. 36 illustrating a method of decoupling a flow chamber and a handle of the uroflowmeter in accordance with various embodiment of the present disclosure.

FIG. 38B is a partial detailed perspective view of an example of an attachment of a flow chamber and a handle of the uroflowmeter of FIG. 36 taken at line 38B-38B of FIG. 38A.

DETAILED DESCRIPTION

The present disclosure generally relates to a uroflowmeter and method for processing data generated therefrom. The uroflowmeter may collect, measure, and transmit data regarding urine flow rate, duration, volume, timestamp of the void, and/or other parameters. The uroflowmeter may be a handheld device, and may include a handle and a urine flow chamber. In some aspects, the uroflowmeter is a portable handheld device. For example, the handle may be grasped by a patient's hand rather than mounting the device on a toilet seat or within a toilet. In some aspects, the device may be attached to the toilet seat or rim of the toilet. The flow chamber may receive the patient's urine, and a sensor may be operatively associated with the flow chamber to measure the urine flow rate, for example. Data from the sensor may be transmitted to a database for data processing. A data processing system, for example an automated voiding diary system, may gather and/or process data from the sensor to help a physician diagnose and treat conditions related to urinary incontinence (and/or lower urinary tract symptoms or "LUTS") and/or other conditions. The automated voiding diary system may include an application for an electronic device, such as a mobile phone, for tracking fluid intake before the urination, symptoms associated with the urination and incontinence before the urination, thus falsely reducing the true urine volume measured by the uroflowmeter. Optionally, the device may be portable and sized for receipt in a discreet bag that can be carried alone by a patient or is small enough to fit into a purse, handbag, backpack, satchel, or other similar carrying case.

Figure 1:
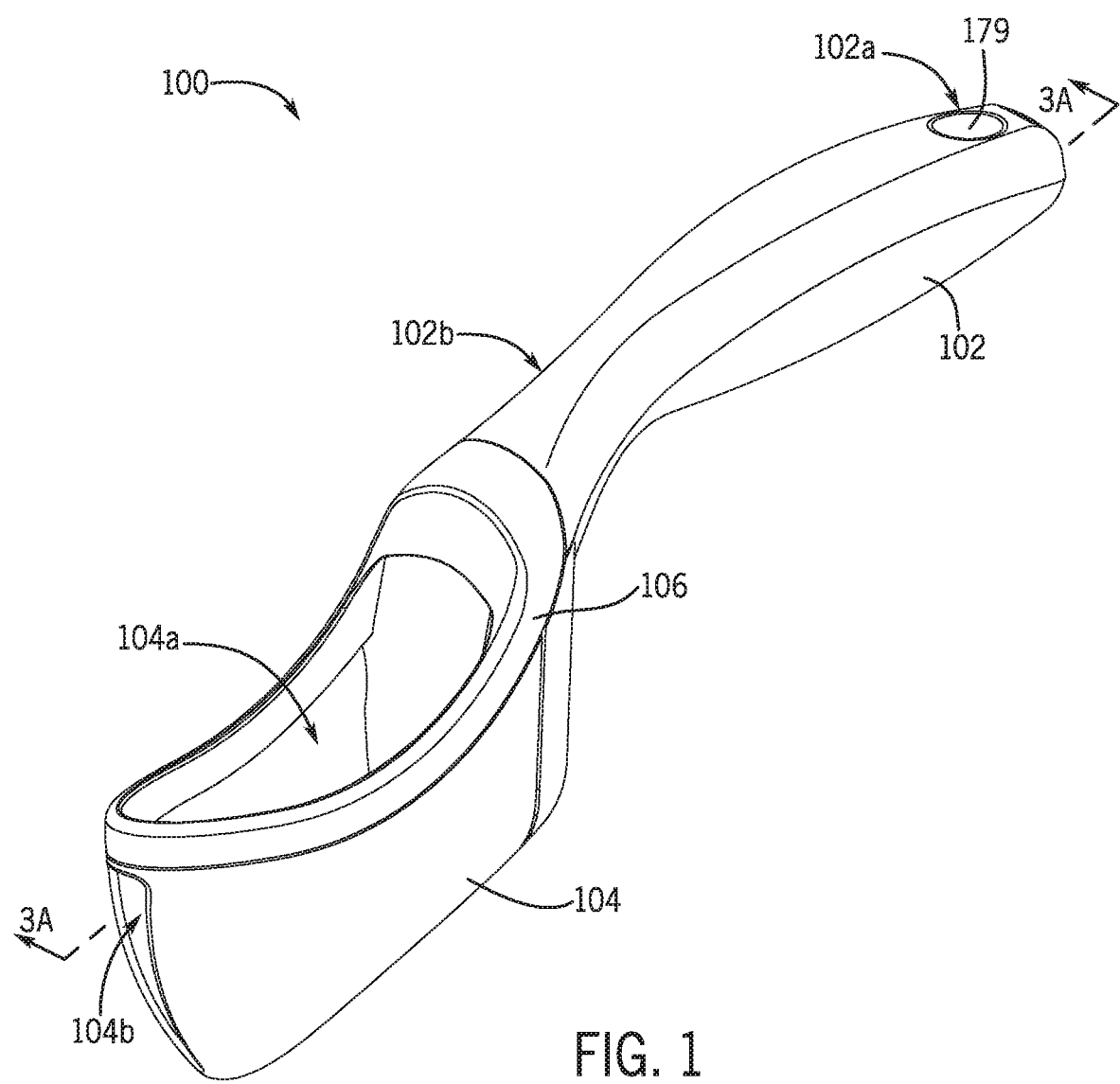
FIG. 1 is a perspective view of a uroflowmeter in accordance with various embodiments of the present disclosure.

FIG. 1 is a perspective view of a uroflowmeter in accordance with various embodiments of the present disclosure. Referring to FIG. 1, a uroflowmeter 100 includes a handle 102 for grasping by a patient. The handle 102 is elongate and relatively slender to provide an ergonomic grip for a patient's hand. The handle 102 includes a proximal end or portion 102a and a distal end or portion 102b. The handle 102 may taper inwardly from its proximal end or portion 102a toward its distal end or portion 102b to facilitate grasping by a patient's hand.

The uroflowmeter 100 may measure urine flow. For example, as illustrated in FIG. 1, the uroflowmeter 100 may include a urine flow chamber or flow chamber 104 that collects and measures urine during patient use. In another example, the uroflowmeter 100 collects urine level data and device orientation data, and transmits that data over a network to another device, such as a server that analyzes and measures urine flow. The flow chamber 104 may include an inlet 104a and an outlet 104b. The inlet 104a may receive urine during patient use, and the outlet 104b may allow the collected urine to exit the uroflowmeter 100, such as into a toilet, for disposal. The inlet 104a may be defined along a top side of the uroflowmeter 100 to facilitate urine collection. The outlet 104b may be defined along a side (such as a front side as illustrated in FIG. 1) of the uroflowmeter 100 to facilitate urine disposal.

Figure 2:
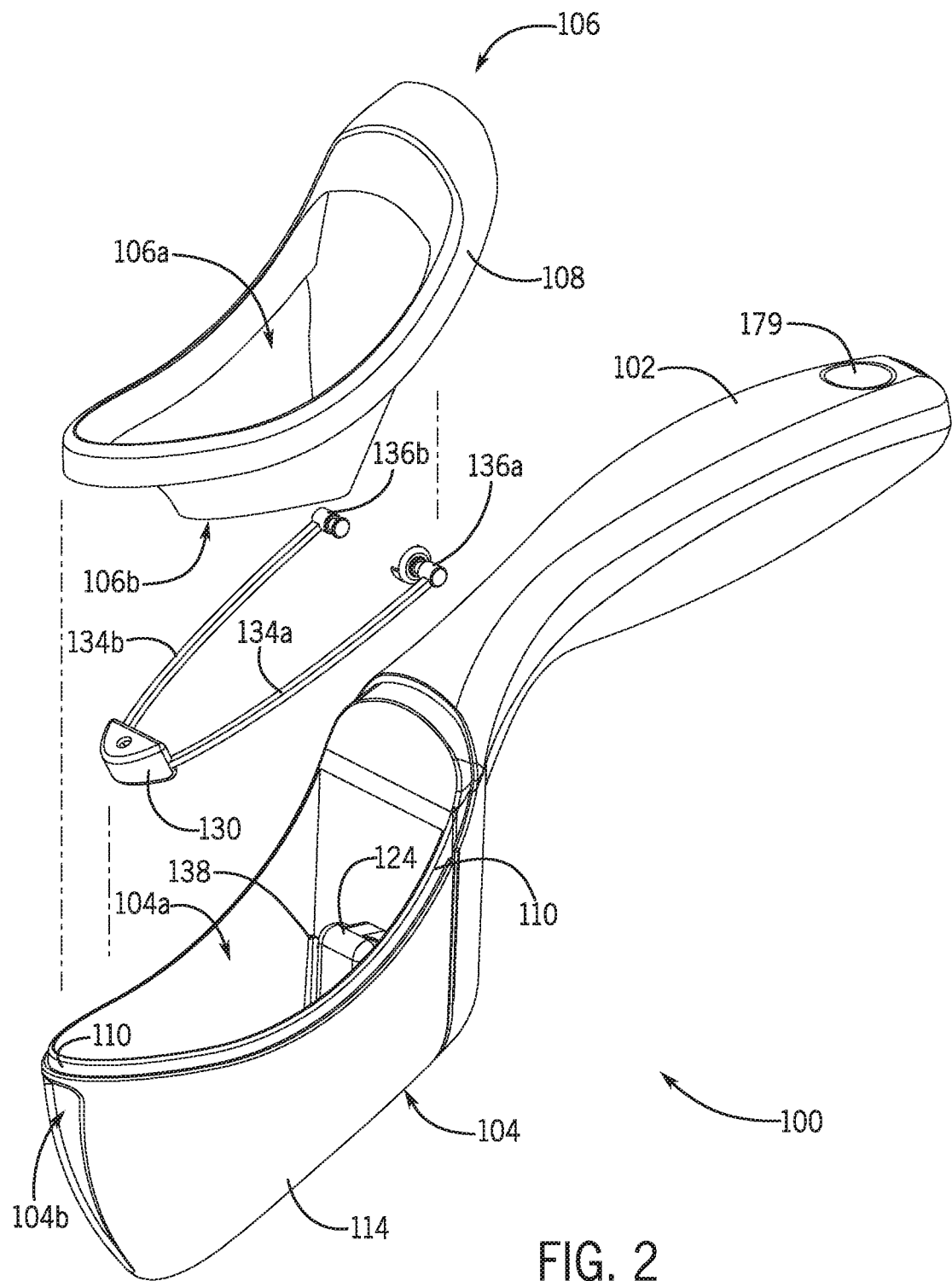
FIG. 2 is an exploded view of the uroflowmeter of FIG. 1 in accordance with various embodiments of the present disclosure.

The uroflowmeter 100 may have a determinable outflow rate. For example, based on the level of urine within the flow chamber 104, the outflow rate of the uroflowmeter 100 can be determined at any given point in time. As illustrated in FIG. 1, the outlet 104b may be formed as a vertically-oriented slot. As illustrated in FIG. 2, the outlet 104b may extend upwardly from a bottom wall 118 toward a rim 110 of the flow chamber 104. In various embodiments, the width of the outlet 104b may increase as the outlet 104b progresses upwardly from the bottom wall 118 toward the rim 110 of the flow chamber 104 (e.g., forming a triangularly-shaped or V-shaped opening), thereby increasing the outflow rate of the uroflowmeter 100 as the fluid level increases within the flow chamber 104 to ensure urine does not overflow out of the flow chamber 104. In other embodiments, the outlet 104b may be a constant width dimensioned to inhibit urine overflow. The outlet 104b restricts urine flow out at low flow rates to improve "low-flow" sensitivity of the system, and larger for higher flowrates (i.e. where less sensitivity is required) to prevent overflow or backflow conditions. In other embodiments, the outlet 104b may also be a series of holes or slots having a different diameter or size, or some combination thereof.

The uroflowmeter 100 may reduce turbulent flow and/or splash back of urine. For example, as illustrated in FIG. 1, the uroflowmeter may include a diffuser or funnel 106 associated with the inlet 104a of the flow chamber 104. The funnel 106 may be friction or interference fit onto the flow chamber 104. The funnel 106 may define a contour that directs or guides a flow of urine into the flow chamber 104. The contour of the funnel 106 may facilitate reducing turbulent flow of the urine within the flow chamber 104. This may produce a smooth or settled flow of the patient's urine within the flow chamber 104. In some cases, the funnel 106 may form a consistent, laminar flow of the urine. As illustrated in the exploded view of FIG. 2, the funnel 106 may include a peripheral lip 108 that mounts onto the rim 110 of the flow chamber 104 to provide a substantially seamless attachment of the funnel 106 to the flow chamber 104; however, this is not required. In other cases, the funnel 106 may be seated at least partially within the flow chamber 104 in a manner that exposes a portion of the rim 110 or other top surface of the flow chamber 104.

Figure 3A:
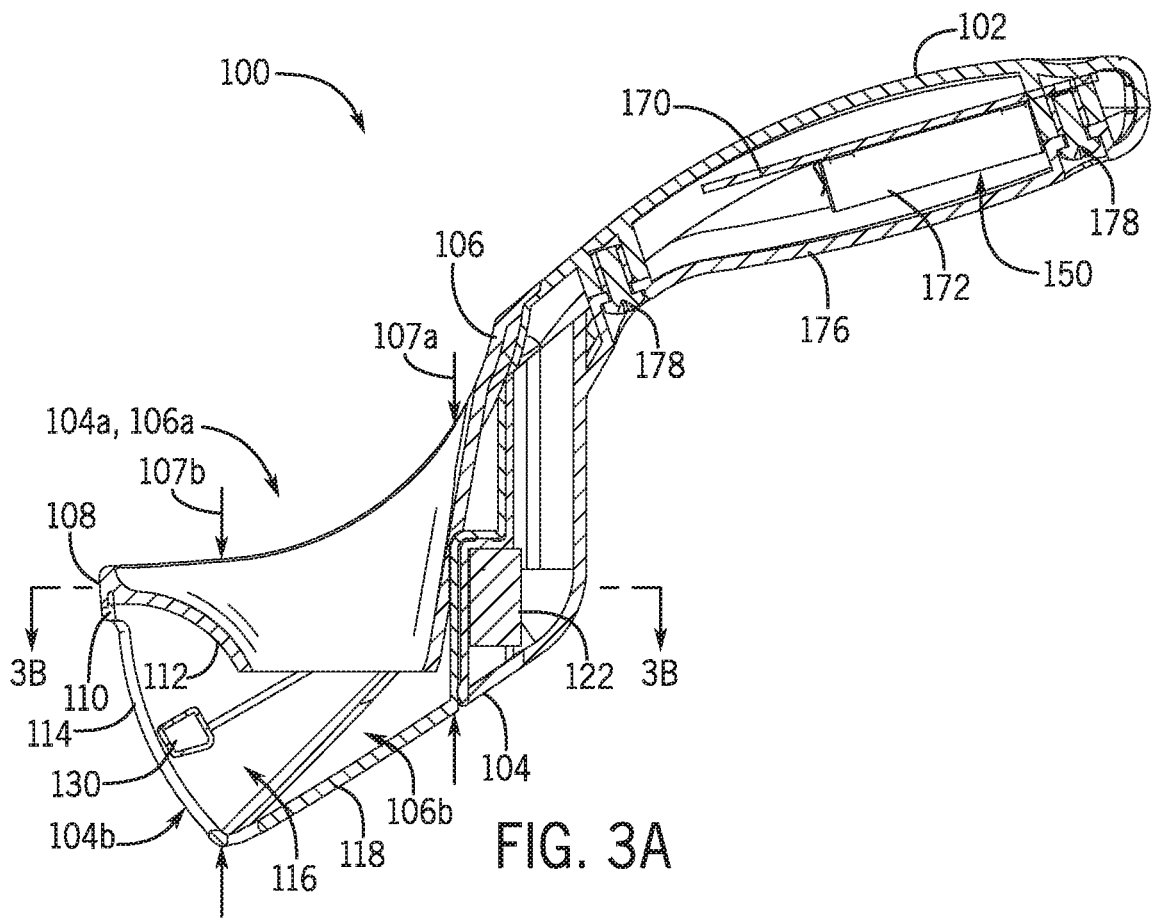
FIG. 3A is a cross-sectional view of the uroflowmeter of FIG. 1 taken along line 3A-3A in accordance with various embodiments of the present disclosure.

As shown in FIGS. 2 and 3A, the funnel 106 may include an inlet 106a and an outlet 106b, and a side wall 112 that tapers inwardly from the inlet 106a to the outlet 106b. The side wall 112 may be shaped (e.g., contoured) to reduce turbulent flow and/or splash back of urine where the urine impacts the side wall 112, and the outlet 106b of the funnel 106 may direct urine toward the bottom wall 118 of the flow chamber 104. Upon impact with the bottom wall 118, the urine may be dispersed outwards toward a side wall 114 of the flow chamber 104 to inhibit splash back of the urine back through the outlet 106b and toward the inlet 106a of the funnel 106. Optionally, features on the interior surface of the flow chamber, where the urine stream strike, may absorb, deflect or diffuse stream energy, reducing or preventing temporary effects on the float or float arm (see later discussion) as well as potential splashback on the user. In one embodiment, the features may be an array of narrow, short projections, like pegs, or channels. The side wall 112 of the funnel 106, and the side wall 114 of the flow chamber 104 may define an annular space. The float may be positioned within the annular space.

In various embodiments, the uroflowmeter 100 is configured for use by female patients. For example, as illustrated in FIG. 1, the flow chamber 104 may be relatively slender to facilitate proper anatomic positioning of the uroflowmeter 100 to receive urinary flow from a female patient. In other cases, such as that described with respect to FIGS. 24-28, a flow chamber may receive flow from a male patient and include an elongated vertical backstop that directs or guides a patient's urine. The funnel 106 (e.g., the lip 108) may contact the patient to provide a seal between the uroflowmeter 100 and the patient during use. In other embodiments, the funnel 106 (e.g., the lip 108) may be placed near the patient to receive the urinary flow but no seal is created. As such, the uroflowmeter 100 may be partially separated from or otherwise detached from a patient during use.

The flow chamber 104 may be coupled to the handle 102. For example, as illustrated in FIG. 1, the flow chamber 104 may be coupled to the distal end 102b of the handle 102. The flow chamber 104 may project distally from the distal end 102b of the handle 102, such that the flow chamber 104 may be referred to as being cantilevered from the handle 102. The cantilevered nature of the flow chamber 104 relative to the handle 102 may facilitate positioning of the flow chamber 104 for patient use. In various embodiments, the handle 102 and the flow chamber 104 may be formed as a unitary or monolithic structure, such as by molding. In other embodiments, the flow chamber 104 may be removably attached to the handle 102. The flow chamber may be made from plastic, in combination with a plastic material, or other appropriate material. The handle may be made from plastic, in combination with a plastic material, or other appropriate material.

The uroflowmeter 100 may be portable, yet sanitary, to facilitate patient use. For example, one or more components of the uroflowmeter 100 may be disposable. In various embodiments, one or more components of the uroflowmeter 100 that are contacted by the patient's urine are disposable, such that the patient, medical professional or supplier may dispose of these components after use. That is, the uroflowmeter includes both reusable components and single-patient use components. In some embodiments, the funnel 106 is disposable and may be considered a single-patient use component. For example, the funnel 106 may be removed from the flow chamber 104 and discarded after patient use. The patient may insert a new funnel 106 into the flow chamber 104 for subsequent use of the uroflowmeter 100. Alternatively, a first patient may return the device to the medical professional or other supplier. The medical professional may return the used device to the supplier. The supplier may dispose of the used funnel, clean and disinfect the rest of the device and then fit the flow chamber with a new funnel. As such, the handle, flow chamber and float may be reused, such as by a different patient, but the single patient use component—the funnel—is thrown away. Alternatively, the funnel, flow chamber, and float may be single patient use.

FIG. 3A is a longitudinal sectional view of the uroflowmeter 100 in accordance with various embodiments of the present disclosure. As illustrated in FIG. 3A, when the funnel 106 is attached to the flow chamber 104, the inlet 106a of the funnel 106 may connect with the inlet 104a of the flow chamber 104, and the side wall 112 of the funnel 106 may project downwardly into the flow chamber 104. The side wall 112 of the funnel 106 may be spaced inwardly of the side wall 114 of the flow chamber 104 to define a reservoir space 116 between the funnel 106 and the flow chamber 104, such as between respective side walls. The outlet 106b of the funnel 106 may be spaced apart from the bottom wall 118 of the flow chamber 104 to provide a flow path for the evacuated or voided urine to flow from the funnel 106 into the flow chamber 104, such as into the reservoir space 116. The funnel may be made from rubber or a soft plastic or other appropriate material to provide more comfort and a better seal for the user.

As descried herein, the flow chamber 104 may be relatively slender to facilitate proper anatomic positioning of the uroflowmeter 100 to receive urinary flow from a female patient. The flow chamber 104 shown in FIGS. 3A and 3B has a width 109 and a length 111. The length 111 may be greater than the width 109 in order to define the relatively slender contour of the flow chamber 104. The flow chamber 104 may also have a height, such as the first height 107a and the second height 107b. The first height 107a may be a height of the flow chamber 104 adjacent the handle 102 and the second height 107b may be a height of the flow chamber 104 adjacent the outlet 104b. Generally, in the embodiment of FIGS. 3A and 3B one or both of the first height 107a or the second height 107b may be less than the length 111. Further, the first height 107a may be different than the second height 107b, in order to define a curved contour along the flow chamber 104.

The uroflowmeter 100 may measure one or more parameters of a patient's urinary voiding. For example, the flow chamber 104 may collect urine and measure one or more urine parameters, for example urine flow rate, flow duration and volume, and then timestamp the act during patient use. The flow chamber 104 may include a differential flow meter or sensor for determining the urinary flow rate. The uroflowmeter 100 may include various types of sensors to determine the flow rate. For example, the uroflowmeter 100 may include a sensor for determining the fluid level in the flow chamber 104. In various embodiments, the uroflowmeter 100 may include one or more image or optical sensors (e.g., for time of flight sensor systems), inductive sensors, and/or magnetic sensors, among others.

Figure 3B:
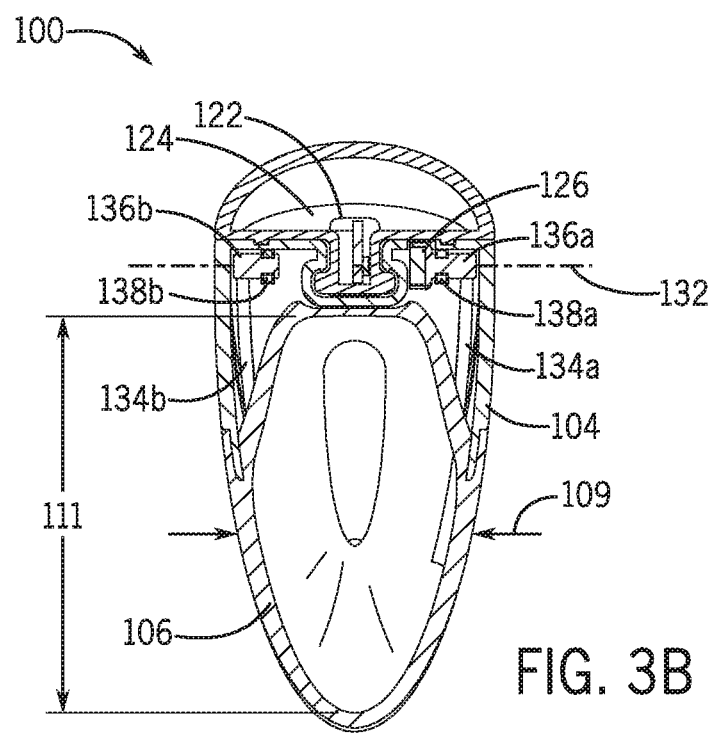
FIG. 3B is a cross-sectional view of the uroflowmeter of FIG. 3A taken along line 3B-3B in accordance with various embodiments of the present disclosure.

As illustrated in the longitudinal sectional view of FIG. 3A and the cross-sectional view of FIG. 3B, the uroflowmeter 100 may include a sensor 122 for detecting the fluid level in the flow chamber 104. The sensor 122 may be coupled to the flow chamber 104 and may be fluidly sealed from the reservoir space 116. For example, as illustrated in FIG. 3B, the flow chamber 104 may define a housing 124 in which the sensor 122 is seated. The housing 124 may seal the sensor 122 from urine in the flow chamber 104, while permitting the sensor 122 to detect the urine level in the flow chamber 104.

In various embodiments, the uroflowmeter 100 may use magnetic Hall effect sensing to determine the fluid level in the flow chamber 104. For example, the sensor 122 may be a magnetic sensor, such as a rotary Hall effect sensor, that detects movement of a magnet located proximate to the sensor 122. In some cases, the sensor 122 may detect a rotary angle of the magnet. Additionally or alternatively, the sensor 122 may detect a change in position of the magnet, including a magnitude of the change in position. Detection may be robust to temperature variations and magnetic and mechanical (for example, air gap, eccentricity, and vibration) tolerances. Also, magnetic field sensors generally are insensitive to dirt, dust, oil, gas, and other contaminants.

As illustrated in FIG. 3B, a magnet 126 may be located proximate the sensor 122. For example, the magnet 126 may be positioned sufficiently close to the sensor 122 such that the sensor 122 can detect the magnetic flux of the magnet 126 to determine the rotary angle of the magnet 126. The sensor 122 may be separated from the magnet 126 by the housing 124, and thus the distance between the magnet 126 and the sensor 122 may ensure the sensor 122 can detect the magnetic flux of the magnet 126 through the housing 124.

The rotational position of the magnet 126 may indicate the fluid level of urine in the flow chamber 104. For example, the magnet 126 may be coupled to a float 130. The float 130 may be positioned in the flow chamber 104, such as the reservoir space 116, and may rise or fall in response to increases or decreases, respectively, in the level of urine in the flow chamber 104. For example, the float 130 may pivot about a pivot axis 132 in response to changes in the level of urine in the flow chamber 104. In various embodiments, one or more arms may extend from the float 130 towards the sensor 122. For example, as illustrated in FIGS. 2 and 3B, first and second arms 134a, 134b may extend from the float 130 toward the sensor 122. The first arm 134a and the second arm 134b may extend along opposite sides of the side wall 112 of the funnel 106 and may terminate on opposite sides of the sensor 122. The first arm 134a and the second arm 134b may be pivotally coupled to the flow chamber 104. For example, first and second axles 136a, 136b may extend inwardly from the terminal ends of the first and second arms 134a, 134b, respectively, and may be rotationally supported by the flow chamber 104 such that the axles 136a, 136b are axially aligned with the pivot axis 132. The first arm 134a and/or the second arm 134b may connect the float 130 and the magnet 126. As illustrated in FIGS. 2 and 3B, the axles 136a, 136b may be supported by one or more cradles 138 (such as first and second cradles 138a, 138b illustrated in FIG. 3B), and the first cradle 138a and the second cradle 138b may be positioned on opposite sides of the housing 124. The magnet 126 may be coupled to one of the axles 136a, 136b (e.g., the first axle 136a as illustrated in FIG. 3B), and the magnet 126 may be axially aligned with the pivot axis 132 of the float 130 such that the magnet 126 is rotatable, but not translatable, relative to the sensor 122 during use. A portion of the float 130 may extend below the arms 134a and 134b to allow the float 130 shape to more closely match the internal geometry of the flow chamber 104.

Figure 4A:
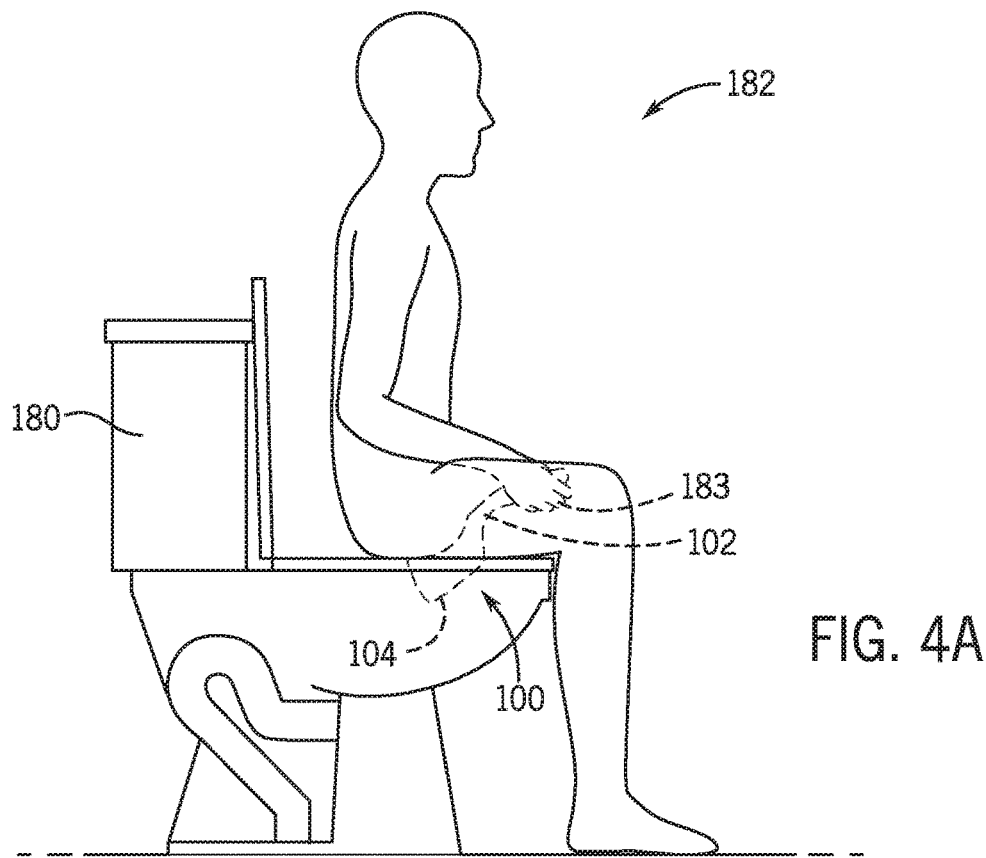
FIG. 4A is a schematic representation of a patient and the uroflowmeter of FIG. 1.
Figure 4B:
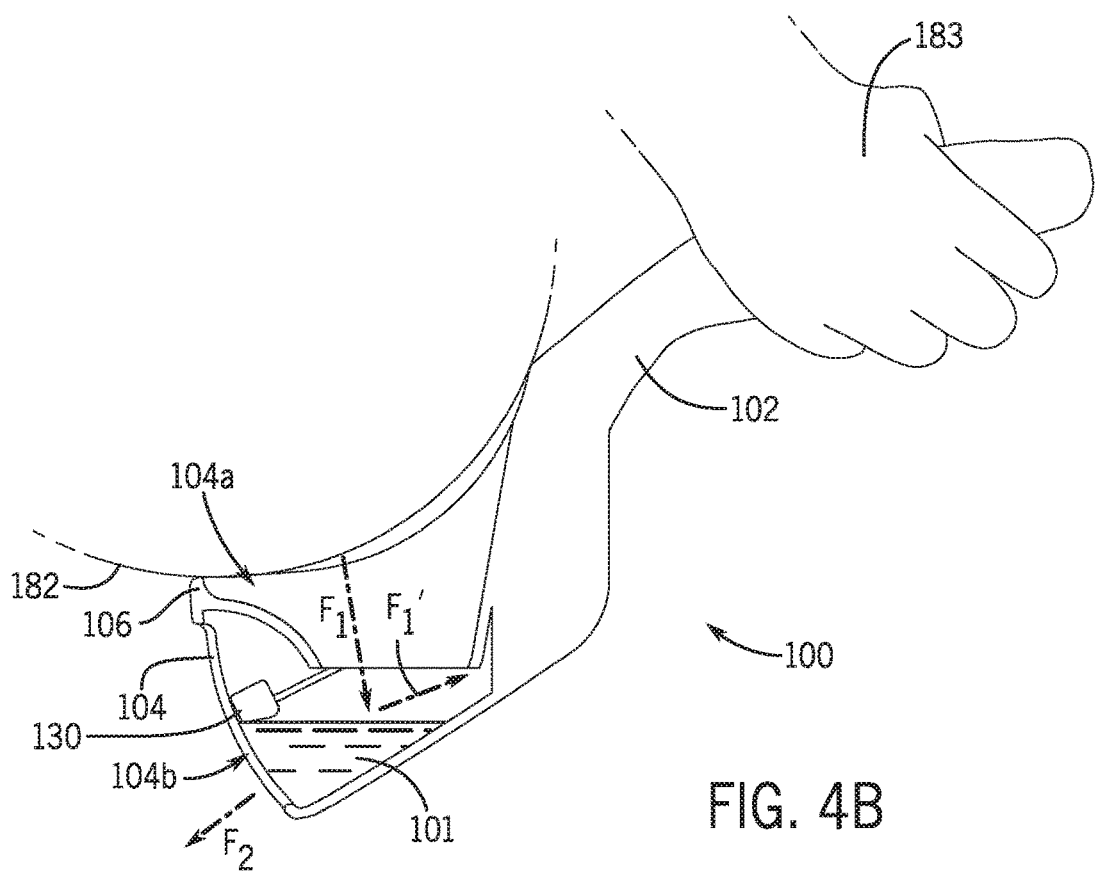
FIG. 4B is an enlarged view of the patient and the uroflowmeter of FIG. 4A, illustrating sample flow paths during use.

FIGS. 4A and 4B depicts the uroflowmeter during a sample use. Broadly, during use, a patient 182 may grasp the handle 102 of the uroflowmeter 100 and position the flow chamber 104 in a proper location for receiving a urine stream from the patient 182. As shown in FIG. 4A, the patient 182 may be seated on a waste receptacle 180. The patient 182 may hold the uroflowmeter 100 while in the seated position shown in FIG. 4A. For example, a hand 183 of the patient 182 may hold the uroflowmeter 100 using the handle 102. This may allow the uroflowmeter 100 to be supported during a voiding event without necessary engaging or contacting the waste receptacle 180.

As shown in FIG. 4B, urine may flow into the flow chamber 104 via the funnel 106. For example, urine may flow generally along a flow path $F_1$ through the funnel 106 via its inlet 106a and may flow out of the funnel 106 via its outlet 106b. The side wall 112 of the funnel 106 may be shaped (e.g., contoured) to reduce splash back of urine onto the patient, for example, such as that which may propagate generally along flow path $F_1'$, shown in FIG. 4B. The urine may be directed into the flow chamber 104 via the funnel 106, and the collected urine may be disposed in the reservoir space 116 within the flow chamber 104. FIG. 4B shows urine 101 within the flow chamber 104. The urine 101 collected within the flow chamber 104 may subsequently exit the flow chamber 104 at the outlet 104b, for example, generally along the flow path $F_2$, shown in FIG. 4B. The flow path $F_2$ may extend away from the uroflowmeter 100 and the patient 182, and be subsequently received by the waste receptacle 180.

Figure 5A:
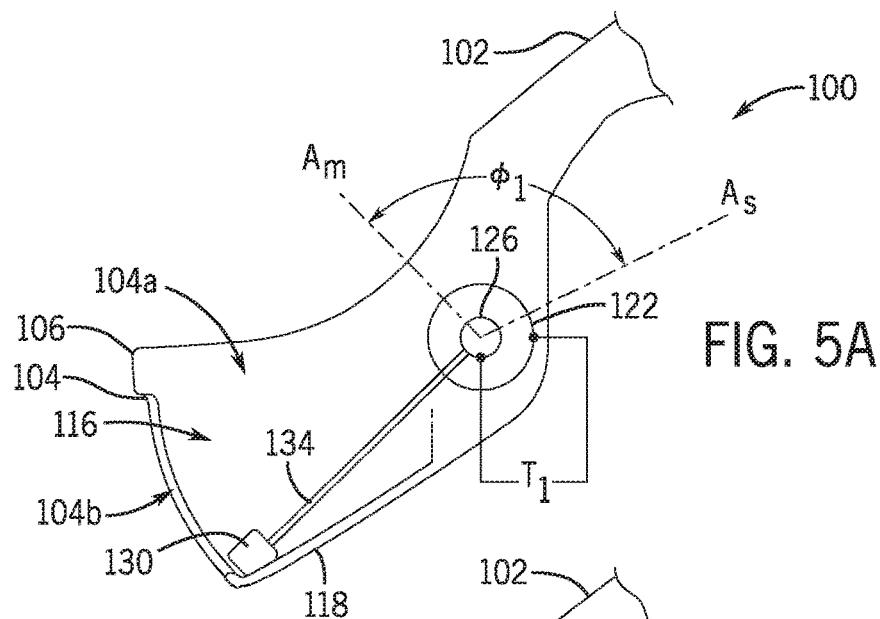
FIG. 5A depicts the uroflowmeter of FIG. 1 in a first configuration.
Figure 5B:
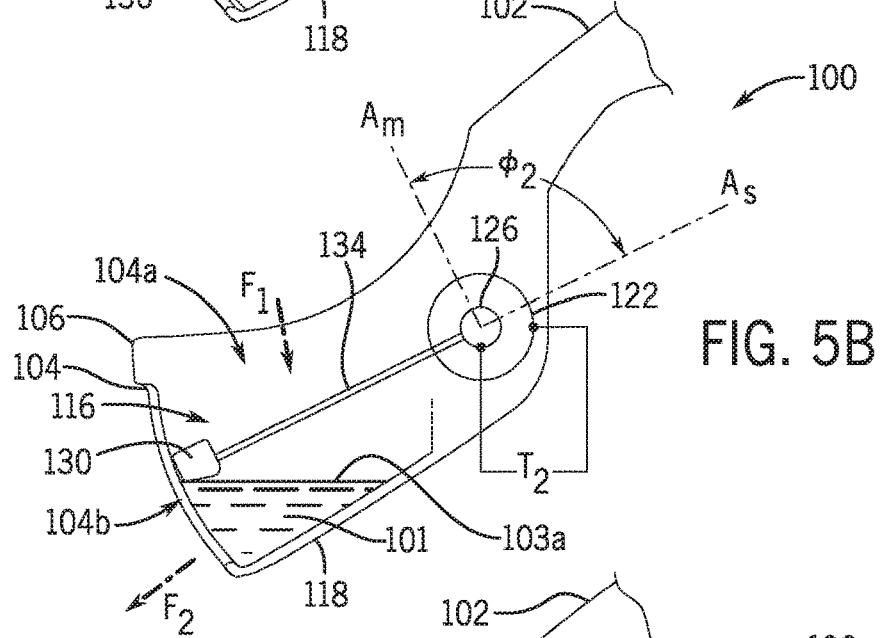
FIG. 5B depicts the uroflowmeter of FIG. 1 in a second configuration.
Figure 5C:
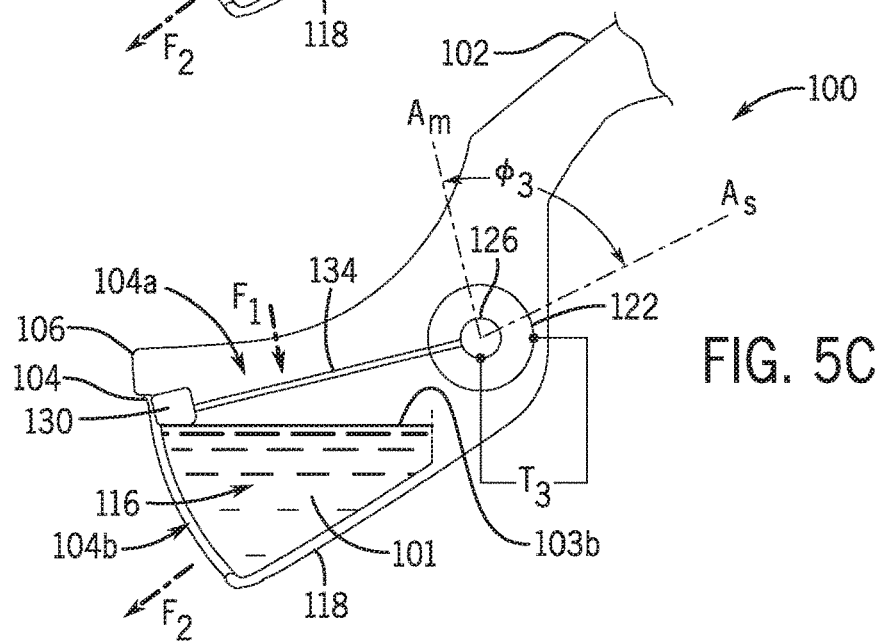
FIG. 5C depicts the uroflowmeter of FIG. 1 in a third configuration.

FIGS. 5A-5C depict the uroflowmeter 100 in various configurations corresponding to a level of urine within the flow chamber 104. Broadly, the float 130 may provide an indication of the fluid level in the flow chamber 104 at any given point in time. With reference to FIG. 5A, the uroflowmeter 100 is shown in a first configuration in which the flow chamber 104 is substantially empty or otherwise free of urine. The first configuration may be representative of the uroflowmeter 100 prior to use by the patient 182. With reference to FIGS. 5B and 5C, the uroflowmeter is shown in a second configuration and a third configuration, respectively, in which the flow chamber 104 includes a volume of urine, such as that received generally along the flow path $F_1$. During a voiding event, the volume of urine in the flow chamber 104 may increase, and thus the embodiment of FIG. 5C shows the flow chamber holding an increased volume of urine as compared with the configuration of FIG. 5B. The uroflowmeter 100, as described herein, detects the increased volume and/or the flow rate during the voiding event.

For example, as the level of urine increases in the flow chamber 104, the float 130 rises within the flow chamber 104. Similarly, as the level of urine decreases in the flow chamber 104, the float 130 falls within the flow chamber 104. As the float 130 rises and falls, the magnet 126 is rotated relative to the sensor 122 via the first and second arms 134a, 134b. The sensor 122 detects an angular position φ of the magnet 126 using its magnetic flux, and the fluid level in the flow chamber 104 can be determined from the angular position data of the magnet 126 (e.g., by using a look-up table that correlates the angular position of the magnet 126 to the position of the float 130, and thus the fluid level in the flow chamber 104).

To illustrate the foregoing, FIGS. 5A-5C show the sensor 122 having a reference direction $A_s$ and the magnet 126 having a reference direction $A_m$. For purposes of illustration, the angular position φ of the magnet 126 may be defined as an angle bounded by the reference direction $A_s$ and the reference direction $A_m$. As the fill level in the flow chamber 104 increases, the magnet 126 rotates, and as such, the reference direction $A_m$ moves relative to the reference direction $A_s$, thereby indicating a change in the angular position φ of the magnet 126.

FIGS. 5A-5C show the sensor 122 detecting a distinct magnetic characteristic T for different angular positions of the magnet 126. For example, in the first configuration of FIG. 5A, the sensor 122 may detect a magnetic characteristic $T_1$, which may correspond to the magnetic flux exhibited by the magnet 126 when arranged at an angular position $φ_1$. The angular position $φ_1$ may correspond to a position of the float 130 at a bottommost portion of the flow chamber 104, such as when the flow chamber 104 is empty.

The float 130 may change position according to a fill level of urine within the flow chamber 104. As the flow chamber 104 fills with urine, such as generally from the flow path $F_1$, the float 130 rises, thereby rotating the magnet 126 and allowing the magnet 126 to exhibit a different magnetic characteristic that is detectable by the sensor 122. To illustrate and with reference to FIG. 5B, the uroflowmeter 100 is shown in a second configuration in which the flow chamber 104 includes urine 101 at a fill level 103a. The float 130 is shown in FIG. 5B in an elevated position from that of FIG. 5A, which corresponds to the fill level 103a of the urine 101. The elevated position of the float 130 at the fill level 103a causes the magnet 126 to rotate for arrangement at an angular position $φ_2$. At the angular position $φ_2$ the magnet 126 may exhibit a magnetic characteristic $T_2$ that is detectable by the sensor 122. In this regard, the sensor 122 may detect the magnetic characteristic $T_2$, which may in turn be used by the uroflowmeter 100 (or associated system or device) to determine a fill level of the flow chamber 104 being the fill level 103a shown in FIG. 5B.

As the flow chamber 104 continues to fill with urine, such as generally from the flow path F1, the float 130 may continue to rise, thereby further rotating the magnet 126 and allowing the magnet 126 to exhibit a different magnetic characteristic that is detectable by the sensor 122. To illustrate and with reference to FIG. 5C, the uroflowmeter 100 is shown in a third configuration in which the flow chamber 104 includes urine 101 at a subsequent fill level 103b. The float 130 is shown in FIG. 5C in an elevated position from that of FIG. 5B, which corresponds to the subsequent fill level 103b of the urine 101. The elevated position of the float 130 at the subsequent fill level 103b causes the magnet 126 to rotate for arrangement at an angular position $φ_3$. At the angular position $φ)_3$ the magnet 126 may exhibit a magnetic characteristic $T_3$ that is detectable by the sensor 122. In this regard, the sensor 122 may detect the magnetic characteristic $T_3$, which may in turn be used by the uroflowmeter 100 (or associated system or device) to determine a fill level of the flow chamber 104 being the subsequent fill level 103b shown in FIG. 5C.

The urinary flow rate of the patient can be determined using the fluid level information (e.g., by calculating changes in the fluid level based on a given outflow rate out of the flow chamber 104, such as the outflow rate of flow along the flow path $F_2$). The fluid level also can be converted to a total volume collected by the uroflowmeter 100 (e.g., by integrating the flow rate curve over the total time period of patient use), or in other words the total volume of urine evacuated or voided by the patient. The fluid level, in addition to pitch and roll, are used as inputs to a multi-dimensional lookup table to determine retained volume and outflow rate. For example, the calculation/process may be: (pitch, roll, fluid level)=>[lookup table]=>(retained volume, outflow rate).

A method of using multi-dimensional lookup tables to determine retained volume, inlet and outlet urine flow rates, and duration data may be as follows. The uroflowmeter 100 may have an outlet 104b that has different outlet flow characteristics at different uroflowmeter 100 orientations, e.g., at different pitch, roll, and/or fluid level sensor 162 positions, which allow determination of flow characteristics by detecting changes of these characteristics. Tables 1A, 1B, and 1C below illustrate exemplary relationships between these values.

TABLE 1A

| Predetermined Float Angular Position φ: 10° | Predetermined Roll deg. 10 | Actual roll deg. 12 | Predetermined Roll deg. 20 |
|---|---|---|---|
| Predetermined Pitch deg. 20 | 12 | | 17 |
| Actual Pitch deg. 30 | 18.5 | 19.7 | 24.5 |
| Predetermined Pitch deg. 40 | 25 | | 32 |
| | Outlet flows mL/sec | | |

TABLE 1B

| Predetermined Float Angular Position φ: 20° | Predetermined Roll deg. 10 | Actual roll deg. 12 | Predetermined Roll deg. 20 |
|---|---|---|---|
| Predetermined Pitch deg. 20 | 17 |  | 23 |
| Actual Pitch deg. 30 | 26 | 27.6 | 34 |
| Predetermined Pitch deg. 40 | 35 |  | 45 |

Outlet flows mL/sec

TABLE 1C

| Predetermined Float Angular Position φ | | Outlet flows mL/sec |
|---|---|---|
| Predetermined Float Angular Position φ | 10 | 19.7 |
| Actual Float Angular Position φ | 18 | 23.65 |
| Predetermined Float Angular Position φ | 20 | 27.6 |

With reference to Tables 1A, 1B, and 1C above, in one example, at a particular moment or snapshot in time (such as a particular sampling interval) during a flow event, the voiding device 100 has a pitch of 30 degrees from horizontal on an axis parallel to pivot axis 132, with the flow chamber 104 angled down relative to the handle 102, has a roll of 12 degrees from horizontal on an axis perpendicular to pivot axis 132, and the float 130 angular position φ is 18°. Continuing the example, a server, such as server environment 2008 (FIG. 6C) contains the following predetermined output flow rate characteristics at a float 130 angular position of 10 degrees. See Table 1A. The server environment 2008 contains an outlet flow rate of 12 mL/sec corresponding to a pitch of 20 degrees, and a roll of 10 degrees. The server environment 2008 contains predetermined output flow rate of 25 mL/sec at a pitch of 40 degrees, a roll of 10 degrees, a predetermined output flow rate of 17 mL/sec at a pitch of 20 degrees and a roll of 20 degrees, and a predetermined output flow rate of 32 mL/sec at a pitch of 40 degrees and a roll of 20 degrees. As shown, the server environment 2008 contains the following predetermined output flow rate characteristics at a float 230 angular position of 20 degrees, an outlet flow rate of 17 mL/sec corresponding to a pitch of 20 degrees, and a roll of 10 degrees, and the server environment 2008 contains predetermined output flow rate of 35 mL/sec at a pitch of 40 degrees, a roll of 10 degrees. Further, the server environment 2008 contains a predetermined output flow rate of 23 mL/sec at a pitch of 20 degrees and a roll of 20 degrees and contains a predetermined output flow rate of 45 mL/sec at a pitch of 40 degrees and a roll of 20 degrees.

The processing element 152 or the server environment 2008 uses interpolation, for example bi-linear interpolation, to determine the outlet flow rate of 19.7 at the conditions in Table 1A, and 27.6 mL/sec at the conditions of Table 1B. The respective processing element then interpolates between the outlet flow values at predetermined float angular positions φ of 10 and 20 degrees from tables 1A and 1B, respectively, for an actual float position φ of 18 degrees. The respective processing element determines the outlet flow rate of 23.65 mL/sec. See Table 1C. The respective processing element may use other types of interpolation, e.g., linear, cubic, bi-cubic, one dimension nearest neighbor or two dimension nearest neighbor. In various examples, the processing element 152 determines outlet flows using one of the pitch, roll or fluid level sensor 162 position inputs; or any two of the preceding inputs in any combination.

The processing element 152, or the server environment 2008 then uses the float 130 angular position φ and the interpolated outlet flow rate to determine the inlet flow rate. For example, the inlet flow rate is determined as the output flow rate plus any change in retained volume in the flow chamber 104 since the last sampling interval. If the fluid level sensor 162 rises from one sampling interval to the next, then there is more fluid volume retained in the flow chamber 104 in the current sampling relative to the previous sample, and the input flow rate is correspondingly higher than the outlet flow rate. Likewise, if the fluid level sensor 162 falls in the current sampling interval relative to the previous sampling interval, then the outlet flow rate is higher than the inlet flow rate. This retained volume is determined from lookup tables, using similar methods and inputs (e.g., pitch, roll, and fluid level sensor 162 position) as with the outlet flow rates as illustrated e.g., in Tables 1A, 1B, and 1C.

In another example, the predetermined characteristics take the form of a mathematical relationship with float 130 angular position 4, pitch, and optionally roll, as inputs and input flow rate as an output. In one example, the processing element 152 determines urine flow rate by analyzing the outflow rate with float 130 angular position 4 data, and/or uroflowmeter 100 orientation data. In particular, the server environment 2008 (or processing element 152) uses the float 130 position over the detected time period in light of the known exit rate of the flow chamber 104 to determine the rate of flow into the flow chamber 104, e.g., from the user. The above is meant as illustrative only and the flow rate input into the uroflowmeter 100 can be determined in other manners.

The uroflowmeter 100 may provide automatic data transfer to a remote computing device. FIG. 6A is a simplified block diagram of electronics 150 associated with the uroflowmeter 100. Referring to FIG. 6A, the electronics 150 may include one or more processing elements 152, one or more memory components 154, a power source 156, an input/output (I/O) interface 158, one or more orientation sensors 160, and one or more fluid level sensors 162. The electronics 150 may include other components typically found in computing systems, such as communication interfaces and other sensors, among others. Each element of the electronics 150 may be in communication via one or more system buses 166, wirelessly, or the like.

At least some of the components or elements of the electronics 150 may be housed in the uroflowmeter 100. For example, one or more of the processing elements 152, memory components 154, power source 156, input/output (I/O) interface 158, orientation sensors 160, and fluid level sensors 162 may be positioned in or received in the uroflowmeter 100. As illustrated in FIG. 3A, the electronics 150 may be housed in the uroflowmeter 100. For example, one or more of the processing elements 152, memory components 154, power source 156, input/output (I/O) interface 158, and orientation sensors 160 may be housed or received in the handle 102, and the fluid level sensors 162 may be received in the flow chamber 104. The processing elements 152 may be associated with a printed circuit board 170, and the printed circuit board 170 may be received in the handle 102 of the uroflowmeter 100 as illustrated in FIG. 3A, for example. Each element of the electronics 150 will be discussed in turn below.

The one or more processing elements 152 may be substantially any type of electronic device capable of processing, receiving, and/or transmitting instructions. For example, the processing element 152 may be a microprocessor or a microcontroller. Additionally, it should be noted that select components of the electronics 150 may be controlled by a first processing element 152 and other components may be controlled by a second processing element 152, where the first and second processing elements 152 may or may not be in communication with each other. Additionally or alternatively, select data processing steps may be performed by one processing element 152 with other data processing steps performed by different processing elements 152, where the different processing elements 152 may or may not be in communication with each other.

The one or more memory components 154 may store electronic data that is used by the electronics 150 to store instructions for the processing element 152, as well as to store data collected by the sensor 122, for example. The one or more memory components 154 may be magneto-optical storage, read only memory, random access memory, erasable programmable memory, flash memory, or a combination of one or more types of memory components.

The power source 156 may provide power to the components of the electronics 150. Depending on the particular application, the power source 156 may be a battery (for example, battery 172 received in the handle 102 of the uroflowmeter 100 as illustrated in FIG. 3A), a power cord, or any other element that transmits electrical power to the components of the electronics 150. As illustrated in FIG. 3A, the battery 172 may be accessible via a removable cover 176, which may be located on an underside of the handle 102. The cover 176 may be attached to the handle 102 via one or more fasteners 178. The battery may be rechargeable by a power cord or an induction charger component.

The I/O interface 158 may provide communication to and from the electronics 150, such as to or from the uroflowmeter 100. The I/O interface 158 may include one or more input buttons, a communication interface (such as WiFi, Ethernet, Bluetooth™, Cellular, IR or the like), communication components (such as universal serial bus (USB) ports/cables, or the like). In various embodiments, the I/O interface 158 transmits sensor data from the uroflowmeter 100 to a remote computing device, such as a remote server including storage, for processing the sensor data to calculate urine flow rate and total volume voided for each urinary event, reprocessing the data, storing the data, and/or generating reports. In other embodiments, summary flow rate calculations are transmitted to the server.

The one or more orientation sensors 160 may be substantially any type of electronic device capable of measuring the orientation of the uroflowmeter 100. For example, the one or more orientation sensors 160 may be a gyroscope for measuring the orientation of the uroflowmeter 100. Additionally or alternatively, the one or more orientation sensors 160 may be a capacitive (or capacitance) sensor for proximity detection and to automatically power the device on/off. That is, a capacitance sensor in the handle may determine that the handle is held in the patient's hand and may measure the device proximity to the human body. In various embodiments, the one or more orientation sensors 160 may include one or more accelerometers. In various embodiments, both an accelerometer and a capacitive sensor are used to turn the uroflowmeter on automatically. The one or more orientation sensors 160 may measure the orientation of the uroflowmeter 100, and the orientation data may be stored in memory 154. In various embodiments, the uroflowmeter 100 may be configured such that it automatically turns on depending on the orientation of the uroflowmeter 100, e.g., as detected by an accelerometer. For example, when the uroflowmeter 100 is positioned in a proper orientation for patient use as detected by the one or more orientation sensors 160, the one or more processing elements 152 may supply power to the uroflowmeter 100 via the battery 172, thereby turning on the uroflowmeter 100 for patient use. Powering on the device when it is in the correct orientation may happen automatically or may be facilitated via a power button. For example, the uroflowmeter 100 may include a power button 179 (see, e.g., FIGS. 1 and 2) to permit the patient to manually turn the uroflowmeter 100 on or off. As illustrated in FIGS. 1 and 2, the power button 179 may be located at the proximal end 102*a* of the handle 102, such as on an upper surface of the proximal end 102*a* of the handle 102, to facilitate operation by the patient.

In other embodiments, an LED light may illuminate when the device is in a correct, desired, or optimal position or orientation Additionally or alternatively, the uroflowmeter 100 may include a display, such as an LED display. The LED display may be integrated with the handle of the uroflowmeter 100 and operatively coupled with the one or more orientation sensors 160 and/or other sensors. The display may indicate a current or instantaneous orientation of the uroflowmeter 100, including a pitch and/or roll condition. As described herein, the uroflowmeter 100 may have a target condition or target orientation that is associated with an optimal operation of one or more components of the uroflowmeter 100, such as the sensor 122. In this regard, the display may indicate the current orientation of the uroflowmeter 100 relative to the target condition or orientation. When the current orientation matches and/or is within an acceptable range of the target, the uroflowmeter 100 may be in a state in which it receives a flow of a patient's urine. In another example, the LED may illuminate to indicate or communicate a fault condition with the uroflowmeter 100, (e.g., if the battery charge is depleted, a sensor had malfunctioned, or another hardware or software fault condition is detected). In another example, the LED may indicate the state of charge of the battery, e.g., fully charged, partially charged, charge in progress, faulted, or the LED may indicate the end of the battery life.

In some cases, the uroflowmeters described herein may include a validation sensor or assembly that is used to determine collected data as corresponding to a void event. The validation sensor may measure characteristics of the uroflowmeter and/or characteristics of the environment. Such measurements may be compared against a predetermined void characteristic and/or voiding environment. Based on this comparison, the validation sensor may be used to determine that a void event is valid or usable for the calculation of one or more parameters of the event, such as urine flow or volume. Where the comparison varies, the validation sensor may determine that despite the detection of a void event, data collected may be unusable, such as being noisy or error prone. In this regard, to facilitate the foregoing, the validation sensor may include or be coupled with the orientation sensor 160. Additionally or alternatively, the validation sensor may include or be coupled with the fluid level sensors 162.

The one or more fluid level sensors 162 may be substantially any type of electronic device capable of measuring the fluid level in the flow chamber 104 of the uroflowmeter 100. As previously discussed, the uroflowmeter 100 may include one or more images or optical sensors (e.g., for time of flight sensor systems), inductive sensors, magnetic sensors, and/or other sensors. In various embodiments, the uroflowmeter 100 may use magnetic Hall effect sensing to determine the fluid level in the flow chamber 104. For example, the fluid level sensor 162 may be a magnetic sensor, such as a rotary Hall effect sensor, that detects movement of a magnet located proximate to the sensor, such as the sensor 122 and the magnet 126 illustrated in FIG. 3B. The data from the one or more fluid level sensors 162 may be stored in memory 154, and the one or more processing elements 152 may use the fluid level data along with the orientation data from the one or more orientation sensors 160 to determine, for example, the urine flow rate and total volume for each urinary event.

Additionally or alternatively, the fluid level 162 sensor may include a resistive strip, such as that which encounters a change in electrical resistance when exposed to an electrically conductive fluid. In another example, the fluid level sensor 162 may include an optical detector, such as a camera, or light emitter and receiver, that measures liquid level in flow chamber 204 relative to graduation marks (e.g., lines showing the volume of fluid at a given point) within flow chamber 204. In another example, the fluid level sensor 162 may include a light emitter and receiver that measure changes in optical transmissive power through a fiber-optic element at that element is exposed to varying levels of fluid within flow chamber 204. In another example, the fluid level sensor may include a strain gauge, such as a Wheatstone bridge coupled to a buoyant element. The strain gauge measures the strain on the float as it moves, such as in response to various levels of fluid within flow chamber 204.

Figure 6B:
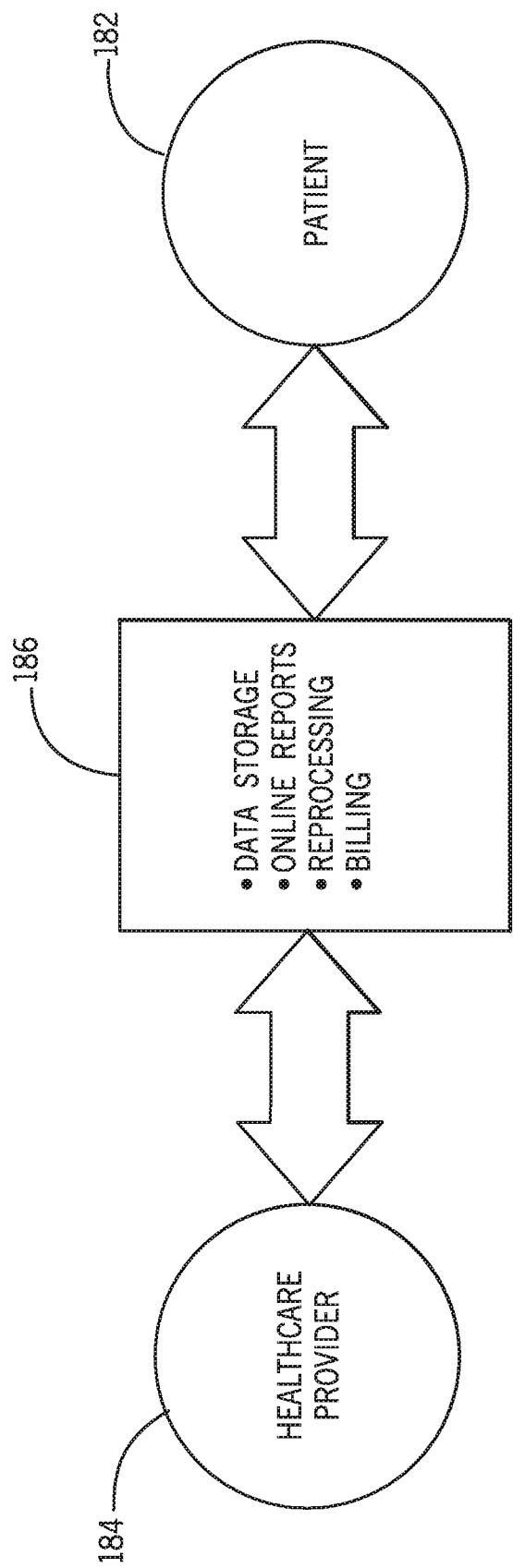
FIG. 6B is a simplified flow chart illustrating a method for gathering and/or processing data of the uroflowmeter of FIG. 1 in accordance with various embodiments of the present disclosure.

FIG. 6B is a simplified flow chart illustrating a method for gathering and/or processing data from the uroflowmeter 100. Referring to FIG. 6B, a patient 182 may schedule an appointment with a healthcare provider 184. In response, the healthcare provider 184 may request an automated voiding diary and/or a uroflow be supplied to the healthcare provider 184 upon the patient's visit to help a physician diagnose and treat conditions related to urinary incontinence. To facilitate preparation of the automated voiding diary, the healthcare provider may transmit the patient contact information to an automated voiding diary system 186 and order an automated voiding diary from the patient. In response, the automated voiding diary system 186 may contact the patient and obtain the patient's billing information, and order a uroflowmeter, such as uroflowmeter 100, for delivery to the patient. The patient may use the uroflowmeter 100 to gather and record their urinary data (e.g., urinary flow rate, total volume, time between urinations, etc.), and the uroflowmeter 100 may automatically transfer or transmit the collected data to the automated voiding diary system 186. The automated voiding diary system 186 may generate reports for the healthcare provider to review prior to the patient's subsequent appointment. The automated voiding diary system 186 may provide a central, online site for the data and reports, including storage and analysis thereof. Additionally or alternatively, the automated voiding diary system can provide information to the device supplier and facilitate ordering, resupply and reprocessing of the device.

Figure 6C:
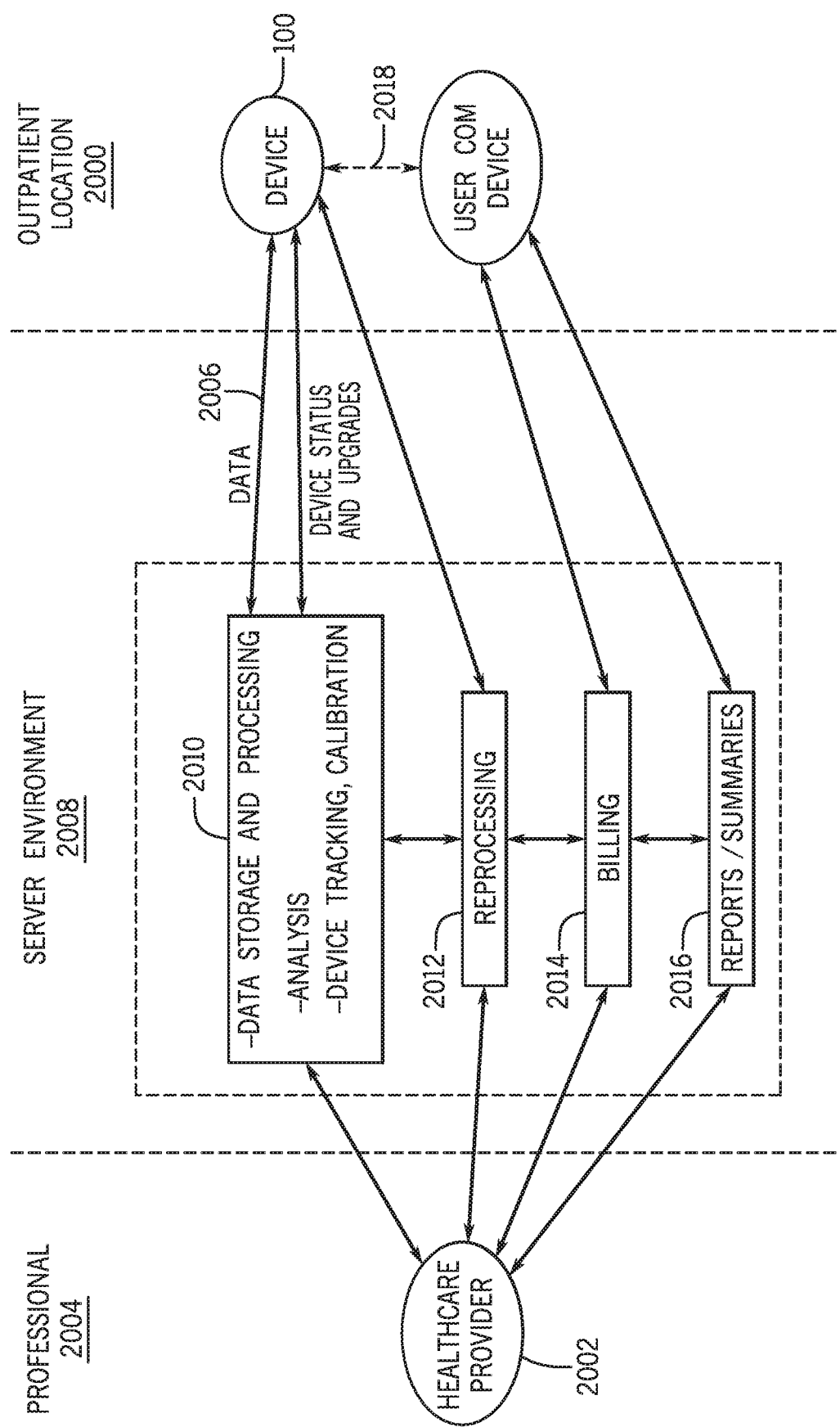
FIG. 6C is one example of a method of implementation of the flow chart of FIG. 6B.

In FIG. 6C, one example is shown of a diagram for implementing the flow chart of FIG. 6B. For ease of the reader, this example is discussed with reference to uroflowmeter 100. However, it is understood that any uroflowmeter disclosed herein may be used in this method of implementation, including, without limitation, uroflowmeter 200, 300, 400, 500, 600, 700, 800, 900, 1000 or 1100.

As depicted in FIG. 6C, the user may be in an outpatient setting 2000 or location remote from the healthcare provider 2002, which is located in a professional setting 2004 such as a doctor's office, a hospital, care facility or the like. For example, the outpatient setting 2000 may be at a patient's home, or substantially any location of the patient remote from the professional setting 2004. The device 100 may be used by a user to collect urine flow data from a voiding act in many outpatient settings, such as in a home setting, an office setting, a public setting, outdoors, or other locations where the user finds himself/herself when the need to void arises. The portable nature of the device 100, given its small size and ease of fitting into a case or container, briefcase, purse, or backpack, for instance, allows the user to keep the device 100 close and in some examples on the user's person in the settings noted herein.

When used during a voiding event, the device may include a capacitive sensor, such as on the handle, to turn on the device 100 by sensing the capacitance of the user's gripping or holding of the device or handle. The orientation sensor (for example an accelerometer) functions to indicate to the user by a signal, such as by a light, sound, or vibration, or combination, when the device 100 is oriented properly for use which aids in obtaining accurate urine flow data collection. For instance, the orientation sensor may detect when the device is oriented with the proper angle (end to end), the proper angle side to side, and/or when it is being held sufficiently still. Upon receiving the indication that the device 100 is ready for use, device 100 is ready to collect the urine flow data and the user may then start and complete the voiding event.

Once the urine flow data is collected, such as in some examples any one or more of the time duration, flow rate, change in flow rate, volume, etc., data is stored in a memory unit within the device 100. The data may be raw and unprocessed or minimally processed, such as by being aggregated and organized to prepare it for transfer. In other examples, the data may be analyzed and summarized and then prepared for transfer. As shown in FIG. 6C, the data, in this example raw data with minimal processing, is transferred to the server environment for subsequent handling via a communication link 2006. The device 100 may transfer the data wireless through a variety of means, including cellularly, by Bluetooth™ connection, over a wireless network, over a wired network, or the like. Suitable network connectivity and components may be disclosed in US2016/0029942, which is incorporated herein by reference in its entirety as if disclosed herein.

The server environment 2008 may include a data storage and processing unit (DSPU) 2010 that may receive the data transferred from the device 100, and also include integrally or separately a reprocessing unit 2012, a billing unit 2014, and a reports and summaries unit 2016. Each of these units may communicate to one or more, including all, of each other. The DSPU may receive input from other sources than the device. The DSPU may output data and information to other components or systems. As shown in FIG. 6B, the device 100 transmits data to the DSPU, in this instance using cellular technology. The DSPU may then act on the data in the manner desired, such as by performing any one or more of the following actions in any order: analyzing the data, correcting the data, deleting the data, storing the data, combining the data, copy or duplicate the data, and/or transmitting the data, among other actions. The DSPU may not act on the data, and may keep it in the form as it was received from the device 100. The results of the actions taken with the data create analyzed data. The analyzed data may take the form of urine flow performance reports, insurance forms, billing forms, or may remain as raw data or minimally processed data. After processing the data from the device 100, the analyzed data may be sent to the healthcare provider 2002. The analyzed data may be requested by the healthcare provider, or may be pushed to the healthcare provider at regular times or irregular times.

The device 100 may send to the DSPU and may receive from the DSPU communication containing the status of the device 100, and may also request and receive firmware upgrades, which may also be pushed to the device from the DSPU without prompting. The device may also provide information to the DSPU, such as to the reprocessing unit, or the DSPU may obtain information from the device 100 and provide it to the reprocessing unit, or the device may directly communicate with the reprocessing unit, about the status of the device 100 relative to the reprocessing function. Upon thresholds being met, such as number of voiding events as one non-limiting example, the DSPU, whether directly or through the reprocessing unit, may shut down the device 100 so that it may be sent back, for example to a reprocessing agent, and reprocessed for subsequent use.

The DSPU, directly or through the billing unit, may act on the data with regard to billing matters and communicate such information to the healthcare provider or to the user, or both, such as through the user com device.

The DSPU, directly or through the Reports and Summaries unit, may provide data and reports based on the data (whether from an individual voiding event or aggregated between more than one voiding event) to the healthcare provider or to the user, such as through the user com device.

In one example, the user device 100 and the user com device do not communicate directly with one another. The user com device may communicate with the DSPU in order to obtain reports on the user's urine data flow, or perform any other functions available to the user on the DSPU (either by accessing a website allowing access to the DSPU, or by using an app on the user com device that allows access to the DSPU).

In another example, the user device and the user com device may communicate directly with one another, as shown by the dashed line 2018 between the two in FIG. 6C.

The user may or may not have in their possession a user communication device, such as a mobile device including a tablet, mobile phone, a computer, e-reader, and so on that may allow access to information stored on the internet, such as on a cloud device or a physical server, referred collectively herein as a server environment.

By sending un-analyzed or raw data from the device 100 to the DSPU, and performing the analytics of the urine flow data on the DSPU and not on the device 100, the data flow between the two devices can be made efficient, the processing capabilities of the control unit of the device may be simplified and be less costly, the reliability of the performance of the device 100 would be improved, and the power consumption may be reduced.

Additionally or separately, in some examples the device performance may be calibrated to develop a calibration factor in order to help insure accurate urine flow readings during voiding events. The calibration of each device 100 may be custom to each device or may be a known constant across more than one device 100. Either way, the data sent from the device to the DSPU may include the identification of the device 100 from which was collected. The DSPU may then be able to apply the correct calibration factor to the correct device in order to properly interpret the data received from the device and create accurate reports and summaries.

The example shown here may also be applied where a user is in the facility of the healthcare provider, for instance, providing urine flow data by using the device 100 in a restroom, in which case the method and system described herein would also work.

Reprocessing of the device may include cleaning, disinfecting and sanitizing reusable components of the device and disposing and replacing the new, single-patient use components of the device. Reprocessing may also include quality control and repackaging of the device with new components, ready for shipping to the next patient. Reprocessing may also include recharging the battery, purging stored information, and/or testing the device for readiness.

In some aspects, the reprocessing workflow may include various steps, and not all steps are necessarily included in the process. In one aspect, a step of ordering, where the uroflowmeter is ordered by a medical professional. In a distribution step, the uroflowmeter is activated and given to a patient at the office of the medical professional. In a use step, the patient uses the device to create a voiding diary or measure uroflow. Optionally or additionally, in a collection step, the device is collected at the office of the medical professional and mailed to the device supplier. In a reprocessing step, the device is reprocessed according to Food and Drug Administration, The Association for Professionals in Infection Control and Epidemiology, and Centers for Disease Control guidelines. Optionally or additionally, in a restocking step, the device is restocked with the medical professional.

To facilitate use of the automated voiding diary system 186, the patient may download an application for their electronic device (e.g., a mobile phone), and the application may track urine voidance measured by the uroflowmeter 100. In various embodiments, the application may also receive patient input of other diagnostically relevant patient data, such as fluid intake, bladder leaks, bedtime and awake time and other voiding details. In various embodiments, the application (and/or the system as described above) may provide data storage, generate online reports, reprocessing, and/or billing, among other items. The healthcare provider may be able to access the application to view the patients reports, invoice the patient, distribute and/or activate and/or return the device, for example. In various embodiments, the application may automatically transmit the automated voiding diary reports to the healthcare provider based on information (e.g., appointment dates) entered into the application by the patient or the healthcare provider, for example.

Figure 7:
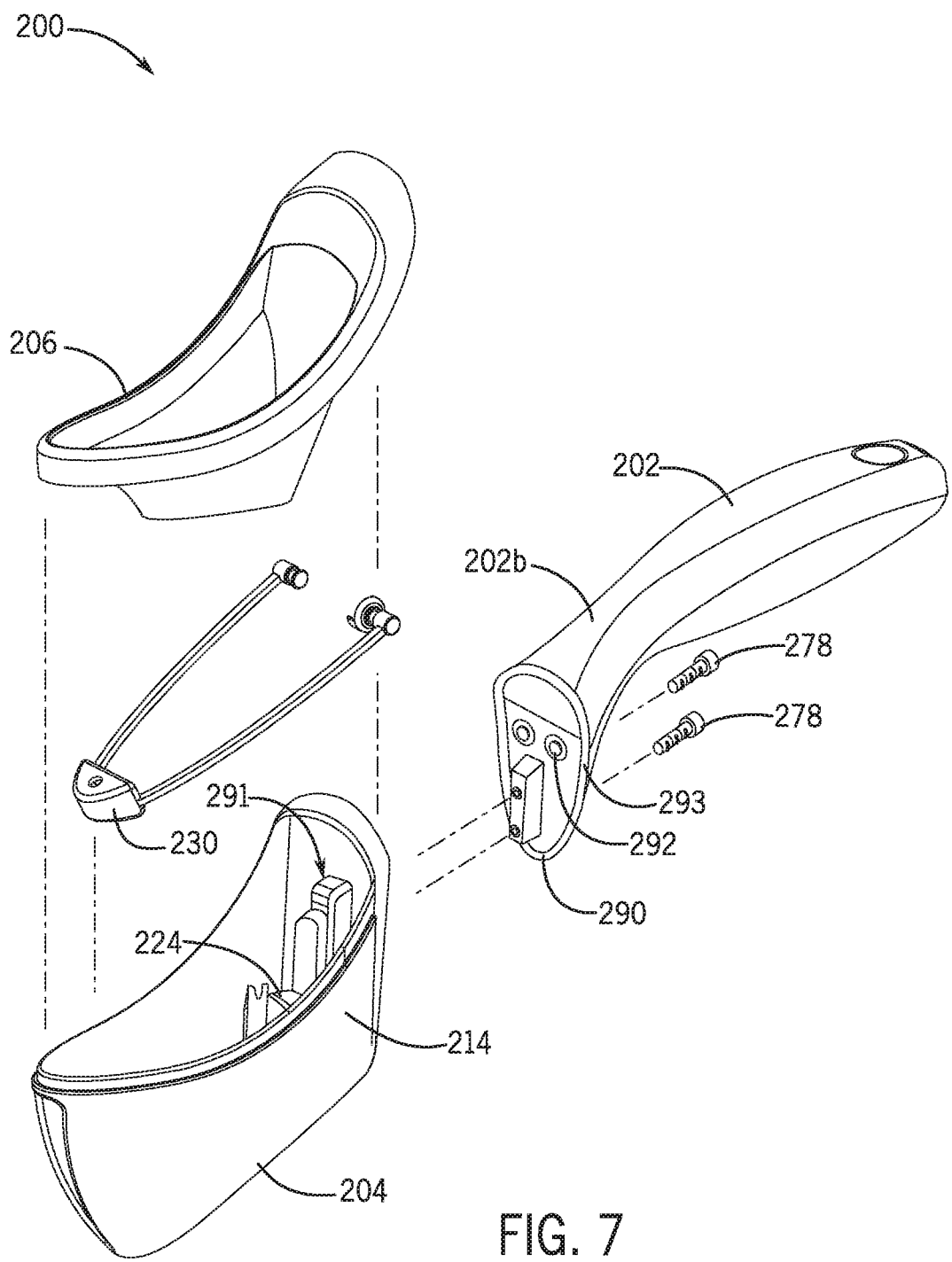
FIG. 7 is an exploded view of an alternative uroflowmeter in accordance with various embodiments of the present disclosure.

FIG. 7 is an exploded view of a uroflowmeter 200 including a handle 202, a flow chamber 204, a funnel 206, and a float 230. The uroflowmeter 200 generally includes the same components and operates in the same manner as the uroflowmeter 100, and thus the description of the uroflowmeter 100, including the handle 102, the flow chamber 104, the funnel 106, and the float 130, is equally applicable to the uroflowmeter 200, including the handle 202, the flow chamber 204, the funnel 206, and the float 230, except as noted below.

Figure 8:
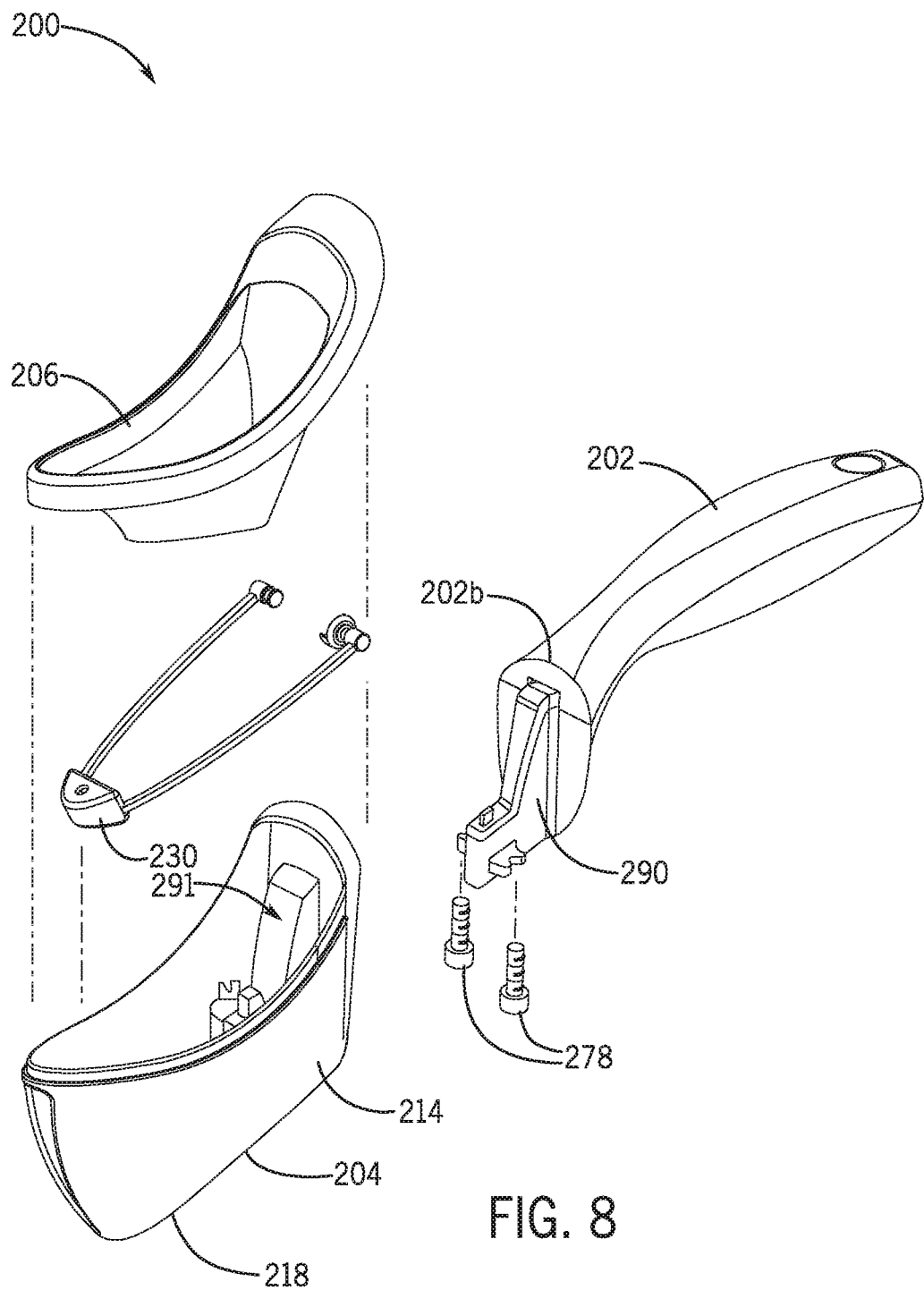
FIG. 8 is an exploded view of an alternative uroflowmeter in accordance with various embodiments of the present disclosure.

In contrast to the uroflowmeter 100, the flow chamber 204 of the uroflowmeter 200 is removably attached to the handle 202. For example, as illustrated in FIG. 7, the flow chamber 204 may be removably attached to the handle 202 via one or more fasteners 278. The fasteners 278 may be orientated generally parallel to a longitudinal centerline of the handle 202 and may threadedly engage the side wall 214 of the flow chamber 204 near the magnetic sensor housing 224 (as illustrated in FIG. 7), or the fasteners 278 may be orientated generally perpendicular to the longitudinal centerline of the handle 202 and may threadedly engage the bottom wall 218 of the flow chamber 204 (as illustrated in FIG. 8). Additionally or alternatively, the fasteners 278 may engage by friction fit or snap fit, rather than having threads. By including a removable flow chamber 204, the patient, supplier or medical professional may dispose of the flow chamber 204, the funnel 206, and/or the float 230 after use for cleanliness and disinfecting purposes. In other words, the flow chamber 204, the funnel 206, and the float 230 may be disposable and are single-patient use. That is, the handle may be reused, such as by a different patient, but the single patient use components—the flow chamber, funnel and float—are thrown away.

A locating protrusion 290 may project distally from the distal end 202b of the handle 202 and may facilitate alignment of the flow chamber 204 relative to the handle 202 prior to fastening the flow chamber 204 to the handle 202 via the fasteners 278. For example, the protrusion 290 may be received in a corresponding recess 291 formed in a portion of the side wall 214 of the flow chamber 204 facing the distal end 202b of the handle 202. One or more electrical contacts 292 may be provided on the distal end 202b of the handle 202 for providing electrical communication between the sensor 122 and, for example, the printed circuit board 170 and/or battery 172 (see, e.g., FIG. 3A for reference). A gasket 293 may extend around a peripheral portion of the distal end 202b of the handle 202 and may provide a sealed interface between the flow chamber 204 and the handle 202 to ensure uncontaminated contact between the one or more electrical contacts 292 and the sensor 122. For example, the gasket 293 may define a water or moisture barrier between the handle 202 and the flow chamber 204. This may help prevent contamination of the handle 202 and facilitate reuse of the handle 202 for subsequent patients. As illustrated in FIG. 8, the fluid level sensor may be housed within the protrusion 290, and thus the one or more electrical contacts 292 and the gasket 293 may not be needed.

Figure 9:
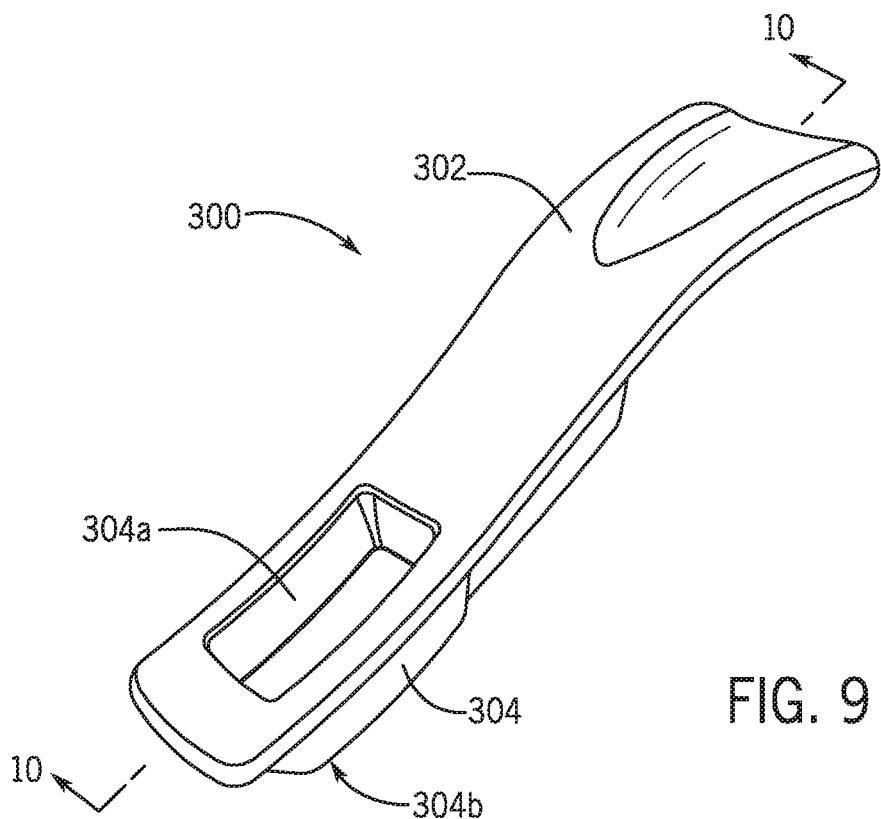
FIG. 9 is a perspective view of an alternative uroflowmeter in accordance with various embodiments of the present disclosure.
Figure 10:
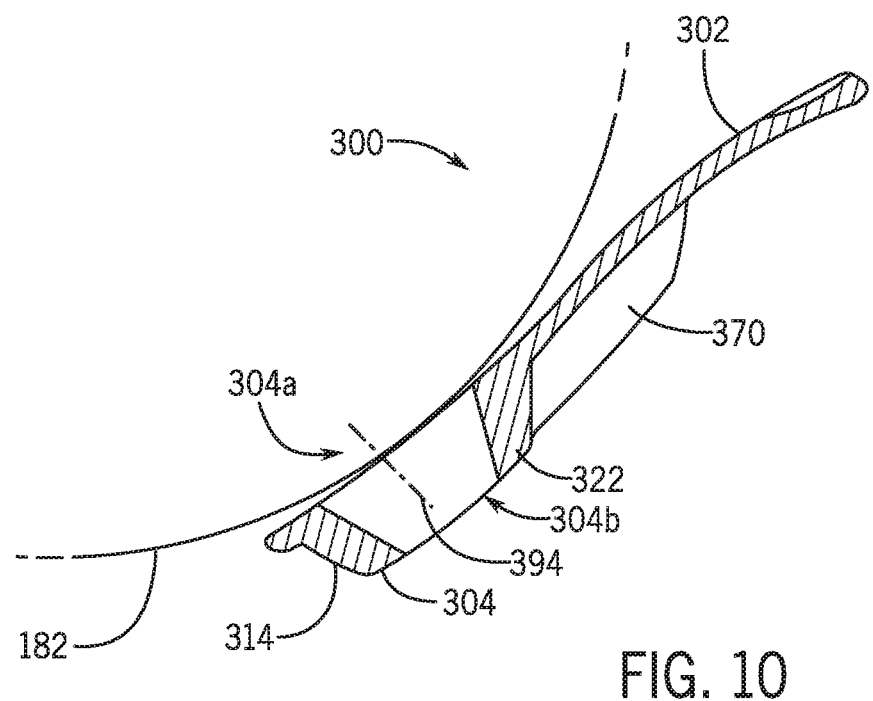
FIG. 10 is a longitudinal sectional view of the uroflowmeter of FIG. 9 taken along line 10-10 of FIG. 9 in accordance with various embodiments of the present disclosure.

FIG. 9 is a perspective view of another uroflowmeter 300, and FIG. 10 is a longitudinal sectional view of the uroflowmeter 300. As illustrated in FIGS. 9 and 10, the uroflowmeter 300 includes a handle 302 and a flow chamber 304. The uroflowmeter 300 generally includes the same or similar components and operates in the same manner as the uroflowmeter 100, and thus the description of the uroflowmeter 100, including the handle 102 and the flow chamber 104, is equally applicable to the uroflowmeter 300.

In the embodiment of FIG. 9, the uroflowmeter 300 does not include a float. Rather, the uroflowmeter 300 includes a thermal mass dispersion or mass flow rate meter or sensor 322 for measuring the mass flow rate of urine 394 traveling through the flow chamber 304 (e.g., from the inlet 304a to the outlet 304b of the flow chamber 304). Optionally, another "non-contact" sensing technology may be used, such as visual- to measure length, width or diameter of cross-section of urine stream passing through. The sensor 322 may be embedded in the side wall 314 of the flow chamber 304, and the sensor 322 may be electrically coupled to electronics 370 received in the handle 302. During use, a patient 182 may place the uroflowmeter 300 against their skin and urinate through the opening defined in the flow chamber 304. The sensor 322 may detect the mass flow rate of the urine 394, and the mass flow rate may be used to determine the total volume of urine evacuated by the patient 182.

Figure 11:
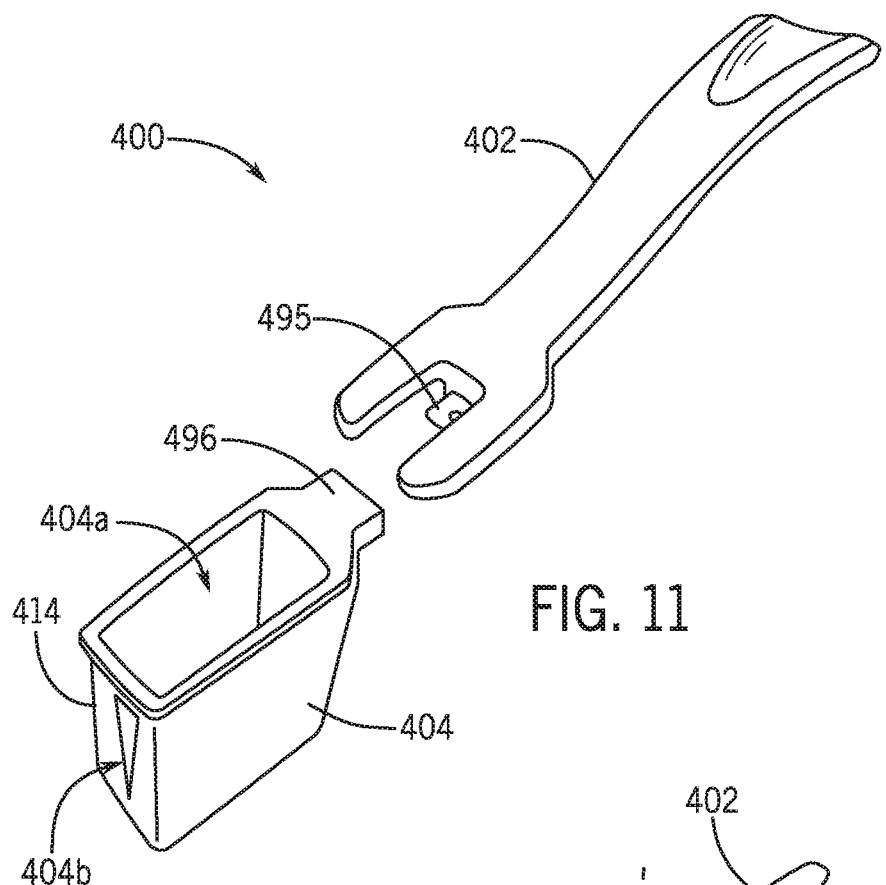
FIG. 11 is an exploded view of an alternative uroflowmeter in accordance with various embodiments of the present disclosure.
Figure 12:
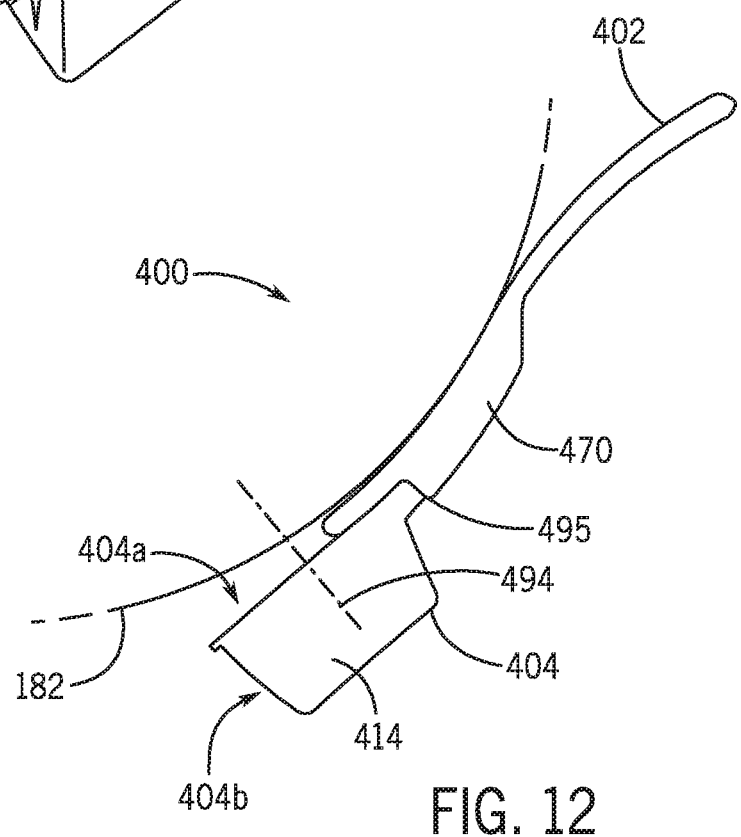
FIG. 12 is a longitudinal sectional view of the uroflowmeter of FIG. 11 in accordance with various embodiments of the present disclosure.

FIG. 11 is an exploded view of another uroflowmeter 400, and FIG. 12 is a longitudinal sectional view of the uroflowmeter 400. As illustrated in FIGS. 11 and 12, the uroflowmeter 400 includes a handle 402 and a flow chamber 404. The uroflowmeter 400 generally includes the same or similar components and operates in the same manner as the uroflowmeter 100, and thus the description of the uroflowmeter 100, including the handle 102 and the flow chamber 104, is equally applicable to the uroflowmeter 400, except as noted below.

In the embodiment of FIG. 11, the flow chamber 404 of the uroflowmeter 400 is removeably attached to the handle 402, thereby allowing the flow chamber 404 to be disposed of after patient use. In various embodiments, the uroflowmeter 400 does not include a disposable funnel. As illustrated in FIG. 11, the handle 402 may include a prong 495 for insertion into a corresponding recess or receptacle in the side wall 414 of the flow chamber 404. The recess or receptacle may be defined by an extension 496 that projects rearward from the side wall 414 toward the handle 402. When the prong 495 is inserted into the receptacle defined by the extension 496, the flow chamber 404 may be releasably secured to the handle 402 via the prong 495. In other words, the flow chamber 404 may be cantilevered from the handle 402 via the prong 495. The prong 495 may be a load flexure sensor that measures the weight of the flow chamber 404 at any given point of time. The prong 495 may be electrically coupled to electronics 470 housed in the handle 402.

During use, a patient may press the upper surface of the uroflowmeter 400 against their skin and urinate into the flow chamber 404. Urine 494 may travel through the flow chamber 404 (e.g., from the inlet 404a and out of the outlet 404b of the flow chamber 404). The weight of the flow chamber 404 changes based on the amount of urine 494 in the flow chamber 404, and the weight is measured by the load flexure prong 495. The measured weight of the flow chamber 404 including the urine 494 therein may be used to determine the flow rate and the total volume of urine evacuated by the patient 182.

Figure 13:
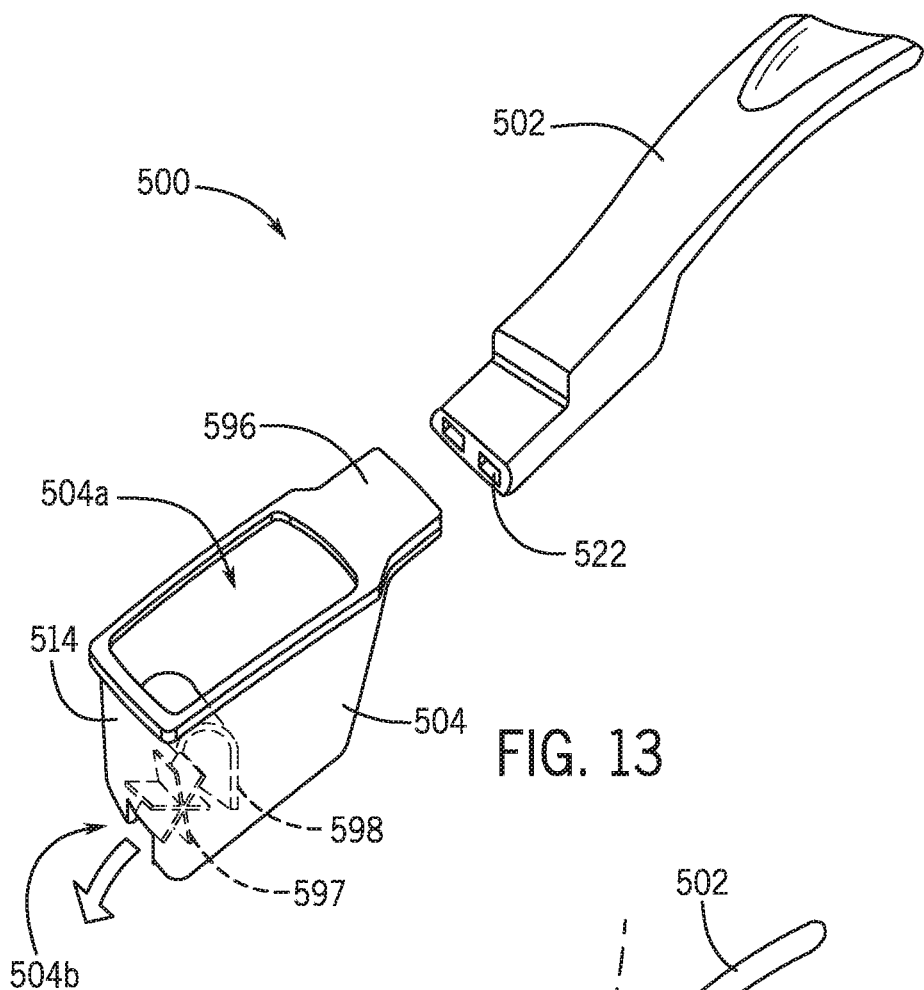
FIG. 13 is an exploded view of an alternative uroflowmeter in accordance with various embodiments of the present disclosure.
Figure 14:
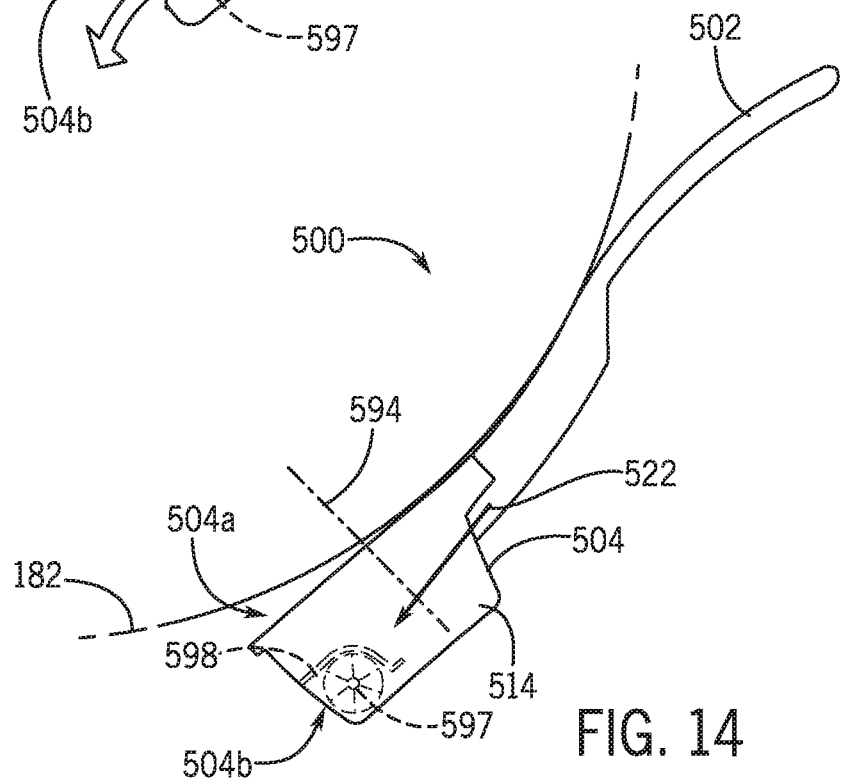
FIG. 14 is a longitudinal sectional view of the uroflowmeter of FIG. 13 in accordance with various embodiments of the present disclosure.

FIG. 13 is an exploded view of another uroflowmeter 500, and FIG. 14 is a longitudinal sectional view of the uroflowmeter 500. As illustrated in FIGS. 13 and 14, the uroflowmeter 500 includes a handle 502 and a flow chamber 504. The uroflowmeter 500 generally includes the same or similar components and operates in the same manner as the uroflowmeter 100, and thus the description of the uroflowmeter 100, including the handle 102 and the flow chamber 104, is equally applicable to the uroflowmeter 500, except as noted below.

In the embodiment of FIG. 13, the flow chamber 504 of the uroflowmeter 500 is removeably attached to the handle 502, thereby allowing the flow chamber 504 to be disposed of after patient use. Thus, in various embodiments, the uroflowmeter 500 does not include a disposable funnel. Although not illustrated in FIG. 13, the handle 502 may be attached to the flow chamber 504 similar to the attachment of the handle 402 of FIG. 11 to the flow chamber 404 (e.g., via a prong). As illustrated in FIG. 13, the handle 502 may include one or more optical sensors 522 located at a distal end 502b of the handle 502. When the handle 502 is attached to the flow chamber 504, the one or more optical sensors 522 may be positioned beneath an extension 596 of the flow chamber 504 that projects rearward from the side wall 514 toward the handle 502. The one or more optical sensors 522 may detect a urine stream 594 passing into the flow chamber 504 and may be operable to determine a fluid level in the flow chamber 504. The one or more optical sensors 522 may be electrically coupled to electronics housed in the handle 502.

To determine the flow rate of the urine stream 594, the uroflowmeter 500 may include a rotatable meter, such as a paddle wheel 597 or turbine. Rotation of the paddle wheel 597 may be proportional to the flow rate of the urine stream 594, and thus the flow rate of the urine stream 594 can be determined by measuring the rotational rate of the paddle wheel 597. The paddle wheel 597 may be associated with the outlet 504*b* of the flow chamber 504, and a shield or shroud 598 may ensure the urine stream 594 contacts only one side (e.g., a bottom half) of the paddle wheel 597 such that urine stream 594 forces the paddle wheel 597 to rotate in a single direction. The shield 598 may be attached to the side wall 514 of the flow chamber 504 and may extend around an outer periphery of the paddle wheel 597. The shield 598 may terminate at a position located below the rotational axis of the paddle wheel 597 to ensure the urine stream 594 contacts a lower half of the paddle wheel 597.

During use, a patient may press the upper surface of the uroflowmeter 500 against their skin and urinate into the flow chamber 504. The urine stream 594 may travel into the flow chamber 504 via the inlet 504*a* and out of the flow chamber 504 via the outlet 504*b*. The one or more optical sensors 522 may detect the fluid level in the flow chamber 504, and/or the paddle wheel 597 may detect the flow rate of the urine stream 594. The detected fluid level in the flow chamber 504 may be used to determine the flow rate and the total volume of urine evacuated by the patient 182. Additionally or alternatively, the detected flow rate of the urine stream 594 may be used to determine the total volume of urine evacuated by the patient 182.

Figure 15:
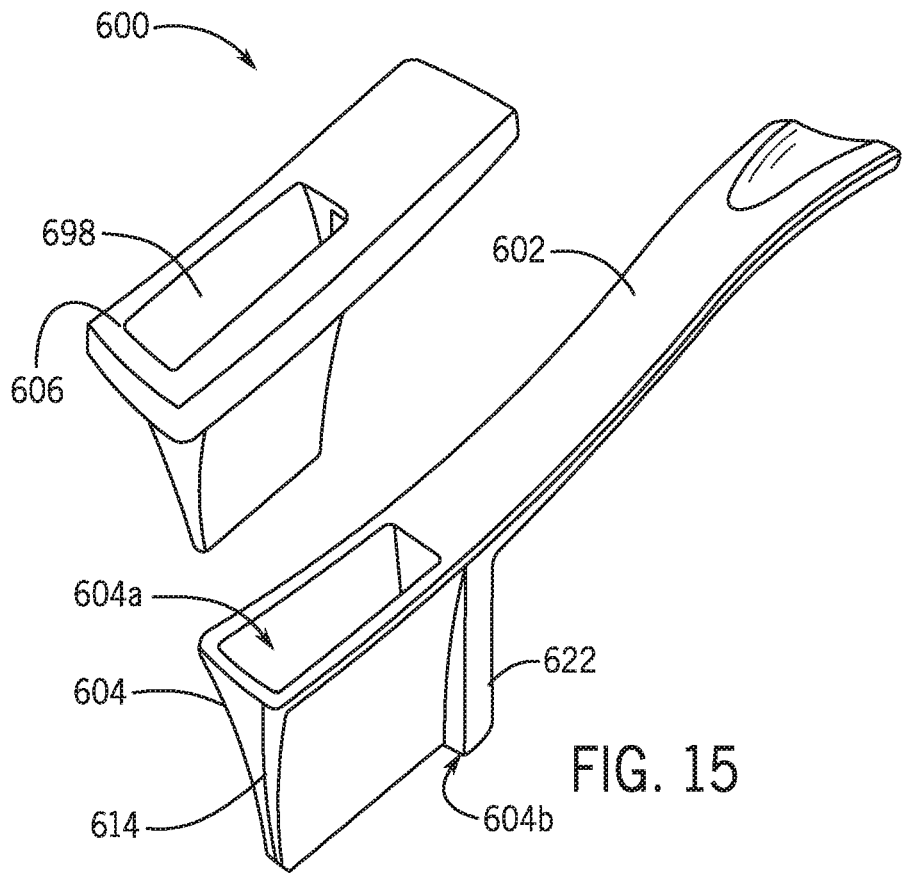
FIG. 15 is an exploded view of an alternative uroflowmeter in accordance with various embodiments of the present disclosure.
Figure 16:
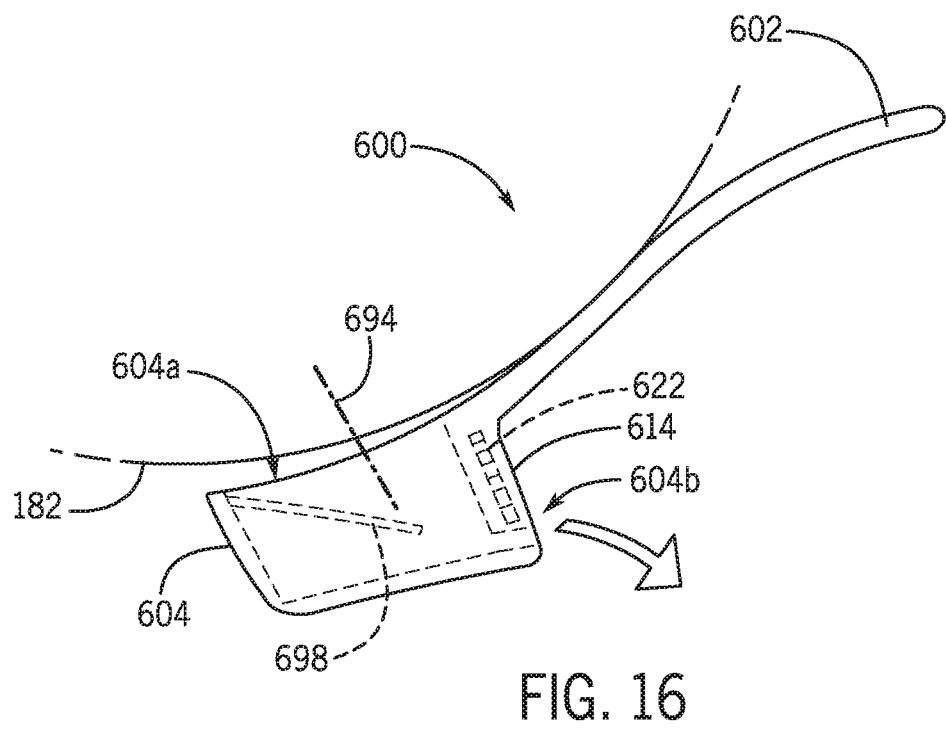
FIG. 16 is a longitudinal sectional view of the uroflowmeter of FIG. 15 in accordance with various embodiments of the present disclosure.

FIG. 15 is an exploded view of another uroflowmeter 600, and FIG. 16 is a longitudinal sectional view of the uroflowmeter 600. As illustrated in FIGS. 15 and 16, the uroflowmeter 600 includes a handle 602, a flow chamber 604, and a funnel 606. The uroflowmeter 600 generally includes the same components and operates in the same manner as the uroflowmeter 100, and thus the description of the uroflowmeter 100, including the handle 102, the flow chamber 104, and the funnel 106, is equally applicable to the uroflowmeter 600, except as noted below.

In contrast to the uroflowmeter 100, the uroflowmeter 600 does not include a float. Rather, the uroflowmeter 600 includes one or more optical sensors 622 for measuring the flow rate of urine 694 traveling through the outlet 604*b* of the flow chamber 604. The one or more optical sensors 622 may be embedded in the side wall 614 of the flow chamber 604. As illustrated in FIG. 16, the one or more optical sensors 622 may be positioned in the side wall 614 directly above the outlet 604*b* of the flow chamber 604. The one or more optical sensors 622 may be electrically coupled to electronics received in the handle 602.

During use, a patient 182 may place the uroflowmeter 600 against their skin and urinate through the inlet 604*a* of the flow chamber 604. The funnel 606 may include a shield 698 directing the patient's urine stream 694 toward the outlet 604*b* of the flow chamber 604. The one or more optical sensors 622 may be positioned to detect the flow rate of the urine stream 694 out of the flow chamber 604. For example, the one or more optical sensors 622 may be positioned in the side wall 614 of the flow chamber 604 and may be directed toward the outlet 604*b* of the flow chamber 604 such that the one or more optical sensors 622 detect the flow rate of the urine stream 694 as it is flowing out of the flow chamber 604 via the outlet 604*b*. The flow rate detected by the one or more optical sensors 622 may be used to determine the total volume of urine evacuated by the patient 182.

FIG. 17 is a perspective view of another uroflowmeter 700, and FIG. 18 is a longitudinal sectional view of the uroflowmeter 700. As illustrated in FIGS. 17 and 18, the uroflowmeter 700 includes a handle 702 and a flow chamber 704. The uroflowmeter 700 generally includes the same or similar components and operates in the same manner as the uroflowmeter 100, and thus the description of the uroflowmeter 100, including the handle 102 and the flow chamber 104, is equally applicable to the uroflowmeter 700.

In the embodiment of FIG. 17, the flow chamber 704 of the uroflowmeter 700 is removeably attached to the handle 702, thereby allowing the flow chamber 704 to be disposed of after patient use. In various embodiments, the uroflowmeter 700 does not include a disposable funnel. As illustrated in FIGS. 17 and 18, the handle 702 may include one or more depth or distance sensors 722 (e.g., time-of-flight sensors) located in a distal end 702*b* of the handle 702. When the handle 702 is attached to the flow chamber 704, the one or more depth sensors 722 may be positioned above the flow chamber 704 such that the one or more depth sensors 722 can detect a level of urine 794 in the flow chamber 704. The one or more depth sensors 722 may be electrically coupled to electronics housed in the handle 702.

To dissipate the energy of the patient's urine flowing into the flow chamber 704 via the inlet 704*a*, the uroflowmeter 700 may include an energy-dissipating device (e.g., grating 798) extending across the inlet 704*a*. The grating 798 may disperse the urine stream entering into the flow chamber 704, thereby dissipating the energy of the urine stream. The grating 798 may be recessed relative to the upper surface of the inlet 704*a* to limit urine splash back. Apertures 799 may be defined in the side wall 714 and/or the bottom wall 718 of the flow chamber 704 to define the outlet 704*b* of the flow chamber 704. The apertures 799 may provide a known exit flow rate based on the urine level in, and the orientation of, the flow chamber 704. Accordingly, the urinary flow rate of the patient may be determined based on the urine fluid level detected by the one or more depth sensors 722. As illustrated in FIGS. 17 and 18, the side wall 714 and the bottom wall 718 may be curved to provide a substantially continuous, arcuate wall.

During use, a patient may press the upper surface of the uroflowmeter 700 against their skin and urinate into the flow chamber 704. The urine stream may travel into the flow chamber 704 via the inlet 704*a* and out of the flow chamber 704 via the outlet 704*b*. For example, the urine stream may flow through the grating 798 located in the inlet 704*a* to dissipate the energy of the incoming urine stream, and the outlet 704*b* may include a plurality of apertures 799 defining a known outflow rate based on the fluid level of urine 794 in the flow chamber 704 and the orientation of the flow chamber 704. The one or more depth sensors 722 may detect the instantaneous fluid level in the flow chamber 704, and the fluid level data may be used to determine the urinary flow rate and the total volume of urine evacuated by the patient 182. As illustrated in FIG. 18, the one or more depth sensors 722 may be located above the urine 794 in the flow chamber 704 and may be directed towards the bottom wall 718 of the flow chamber 704. During use, the one or more depth sensors 722 may transmit a signal towards the urine 794 in the flow chamber 704, and the time elapsed between transmitting the signal and receiving a return signal reflected off of the upper surface of the urine 794 may be used to determine the distance between the sensor 722 and the upper surface of the urine 794. This distance may be used to calculate the depth, and thus the volume, of urine 794 in the flow chamber 704 based on the geometry of the flow chamber 704. Changes in the distance between the sensor 722 and the upper surface of the urine 794 can be used to determine the incoming flow rate of the patient's urine based on the outflow rate of the apertures 799.

Figure 19:
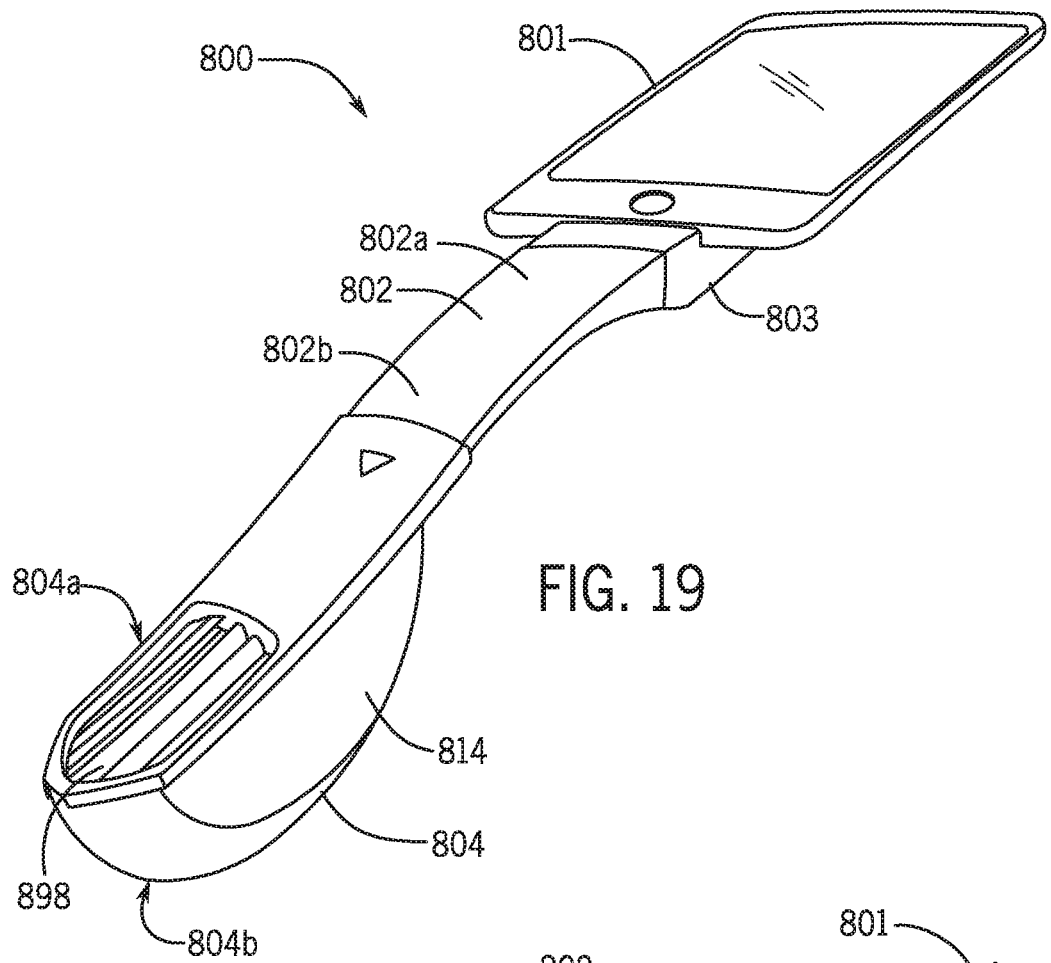
FIG. 19 is a perspective view of an alternative uroflowmeter in accordance with various embodiments of the present disclosure.
Figure 20:
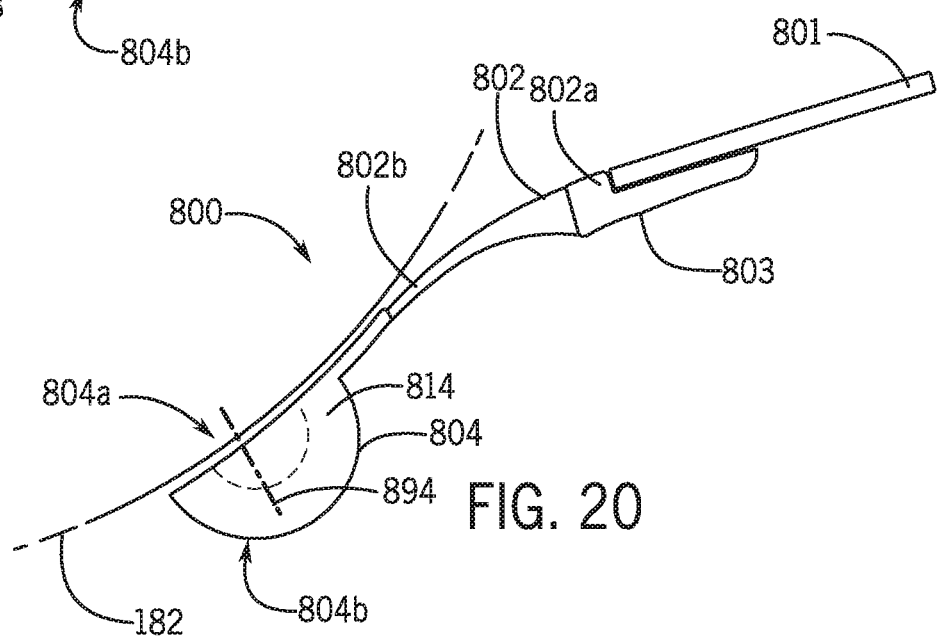
FIG. 20 is a longitudinal sectional view of the uroflowmeter of FIG. 19 in accordance with various embodiments of the present disclosure.

FIG. 19 is a perspective view of another uroflowmeter 800, and FIG. 20 is a longitudinal sectional view of the uroflowmeter 800. As illustrated in FIGS. 19 and 20, the uroflowmeter 800 includes a handle 802 and a flow chamber 804. The uroflowmeter 800 generally includes the same components and operates in the same manner as the uroflowmeter 100, and thus the description of the uroflowmeter 100, including the handle 102 and the flow chamber 104, is equally applicable to the uroflowmeter 800, except as noted below.

In contrast to the uroflowmeter 100, the flow chamber 804 of the uroflowmeter 800 is removeably attached to the handle 802, thereby allowing the flow chamber 804 to be disposed of after patient use. Thus, in various embodiments, the uroflowmeter 800 does not include a disposable funnel. As illustrated in FIGS. 19 and 20, the flow chamber 804 may be removeably connected to a distal end 802b of the handle 802. Although not illustrated in FIGS. 19 and 20, one or more sensors may be attached to the flow chamber 804 for detecting a urine level in the flow chamber 804 and/or a flow rate of a patient's urine stream 894. The one or more sensors may be electrically coupled to a mobile electronic device, such as a mobile phone 801, via an adaptor 803. The adaptor 803 may be connected to a proximal end 802a of the handle 802, and the mobile phone 801 may be connected to the adaptor 803. The adaptor 803 may physically and electrically connect the mobile phone 801 to the uroflowmeter 800. Thus, the mobile phone 801 may, for example via an application installed and running on the mobile phone 801, process the data received from the uroflowmeter 800 and generate a voiding diary entry based on the urinary event. Additionally or alternatively, the uroflowmeter 800 may use the accelerometers in the mobile phone to determine handle/device orientation, and may use other features of the phone, such as the touch screen, indicators (display) and connectivity (cellular) rather than including these features in the device.

To dissipate the energy of the patient's urine flowing into the flow chamber 804 via the inlet 804a, the uroflowmeter 800 may include an energy-dissipating device (e.g., grating 898) extending across the inlet 804a. The grating 898 may disperse the urine stream entering into the flow chamber 804, thereby dissipating the energy of the urine stream. After entering the flow chamber 804, the urine stream 894 may exit the flow chamber 804 via the outlet 804b of the flow chamber 704. The outlet 804b may provide a known exit flow rate. Accordingly, the urinary flow rate of the patient may be determined based on the urine fluid level detected by one or more sensors associated with the flow chamber 804.

During use, a patient may press the upper surface of the uroflowmeter 800 against their skin and urinate into the flow chamber 804. The urine stream may travel into the flow chamber 804 via the inlet 804a and out of the flow chamber 804 via the outlet 804b. For example, the urine stream may flow through the grating 898 located in the inlet 804a to dissipate the energy of the incoming urine stream, and the outlet 804b may define a known outflow rate based on the fluid level in the flow chamber 804 and the orientation of the flow chamber 804. The one or more sensors may detect the instantaneous fluid level in the flow chamber 804, and the fluid level data may be used by the application on the mobile phone 801 to determine the urinary flow rate and the total volume of urine evacuated by the patient 182.

Figure 21:
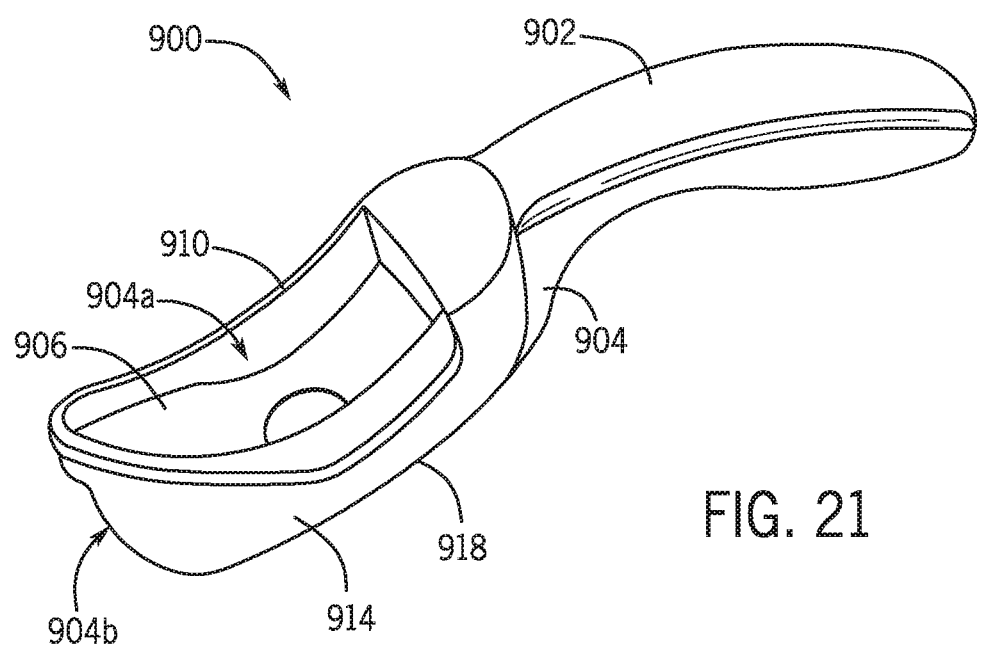
FIG. 21 is a perspective view of an alternative uroflowmeter in accordance with various embodiments of the present disclosure.

FIG. 21 is a perspective view of another uroflowmeter 900 in accordance with various embodiments of the present disclosure. As illustrated in FIG. 21, the uroflowmeter 900 includes a handle 902, a flow chamber 904, and a funnel 906. The uroflowmeter 900 generally includes the same components and operates in the same manner as the uroflowmeter 100, and thus the description of the uroflowmeter 100, including the handle 102 and the flow chamber 104, is equally applicable to the uroflowmeter 900, except as noted below.

In contrast to the uroflowmeter 100, the funnel 906 of the uroflowmeter 900 is not removeably attached to the flow chamber 904. Rather, the funnel 906 is formed as a unitary part with the flow chamber 904. Thus, the uroflowmeter 900 does not include a disposable funnel. In addition, a teeter totter type float may be used. In this way, the float is on the chamber side of the fulcrum and the sensing component is on another end near the sensor. The sensor may be a local capacitive element or vertical capacitive strip running up the back of the chamber. As illustrated in FIG. 21, the funnel 906 may be recessed relative to the rim 910 of the flow chamber 904. For example, the funnel 906 may be fixedly coupled to the side wall 914 of the flow chamber 904 at a distance below the rim 910 of the flow chamber 904 and above the bottom wall 918 of the flow chamber. During use, a urine stream may enter into the flow chamber 904 via the inlet 904a and exit the flow chamber 904 via the outlet 904b. One or more sensors associated with the flow chamber 904 may detect the fluid level and/or flow rate of the urine, and the fluid level and/or flow rate data can be processed locally by the uroflowmeter 900 or transmitted to a remote computing device for processing.

Figure 22:
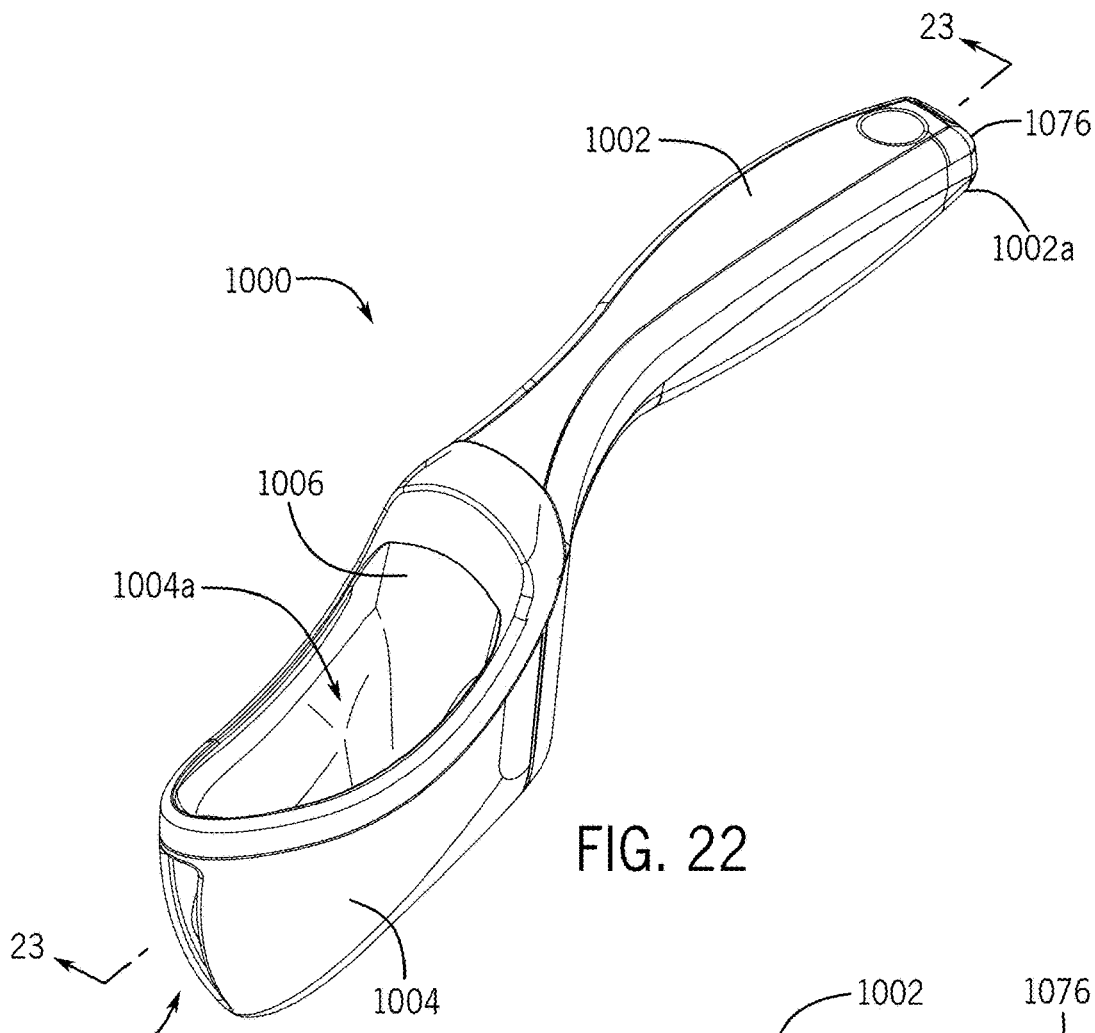
FIG. 22 is a perspective view of an alternative uroflowmeter in accordance with various embodiments of the present disclosure.
Figure 23:
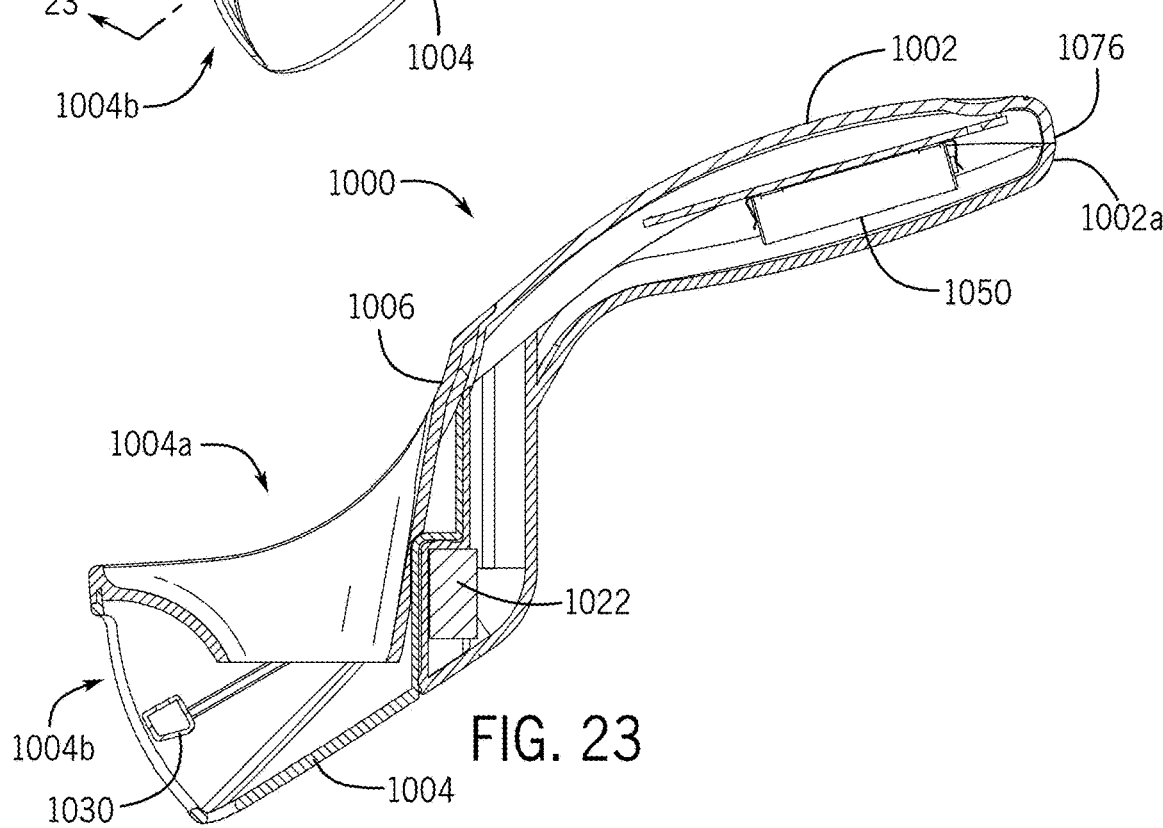
FIG. 23 is a longitudinal sectional view of the uroflowmeter of FIG. 22 taken along line 23-23 of FIG. 22 in accordance with various embodiments of the present disclosure.

FIG. 22 is a perspective view of another uroflowmeter 1000, and FIG. 23 is a longitudinal sectional view of the uroflowmeter 1000. As illustrated in FIGS. 22 and 23, the uroflowmeter 1000 includes a handle 1002, a flow chamber 1004, and a funnel 1006. The uroflowmeter 1000 generally includes the same or similar components and operates in the same manner as the uroflowmeter 100, and thus the description of the uroflowmeter 100, including the handle 102 and the flow chamber 104, is equally applicable to the uroflowmeter 1000.

As illustrated in FIGS. 22 and 23, the uroflowmeter 1000 may include a cover 1076 attached to the proximal end 1002a the handle 1002. The cover 1076 may provide access to electronics 1050 contained inside the handle 1002. The cover 1076 may be snap or interference fit to the handle 1002, thereby removing the fasteners 178 used to attach the cover 176 to the handle 102 of the uroflowmeter 100 illustrated in FIG. 3A. The handle 1002 may include components that are ultrasonically-welded together to ease assembly of the uroflowmeter 1000.

During use, a patient may press the upper surface of the uroflowmeter 1000 against their skin and urinate into the flow chamber 1004 via the funnel 1006. The urine stream may travel into the flow chamber 1004 via the inlet 1004a and out of the flow chamber 1004 via the outlet 1004b. The sensor 1022 may detect the instantaneous fluid level in the flow chamber 1004 via the float 1030, similar to the arrangement described with respect to the uroflowmeter 100, and the fluid level data may be used to determine the urinary flow rate and the total volume of urine evacuated by the patient.

Figure 24:
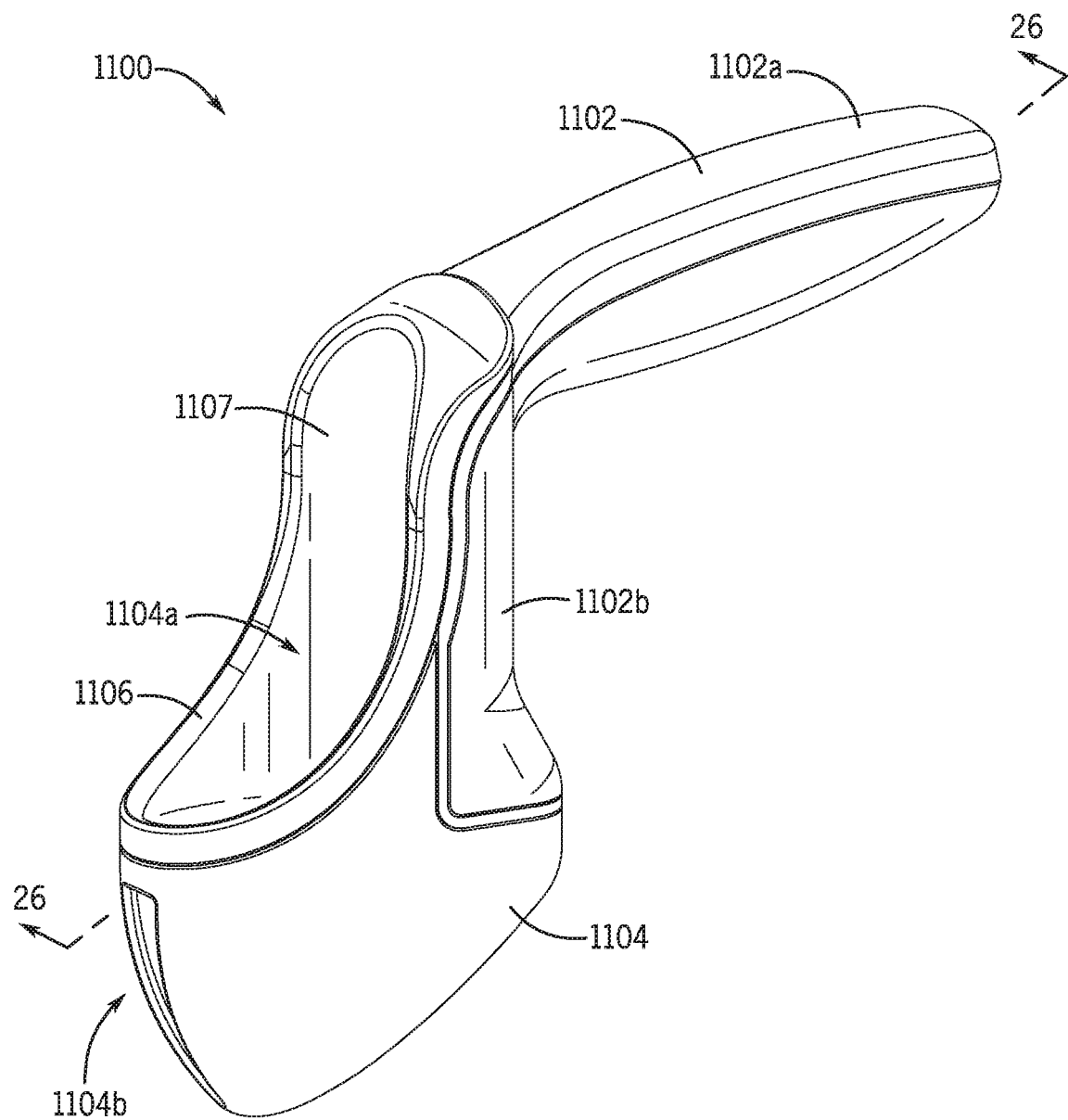
FIG. 24 is a perspective view of an alternative uroflowmeter in accordance with various embodiments of the present disclosure.
Figure 25:
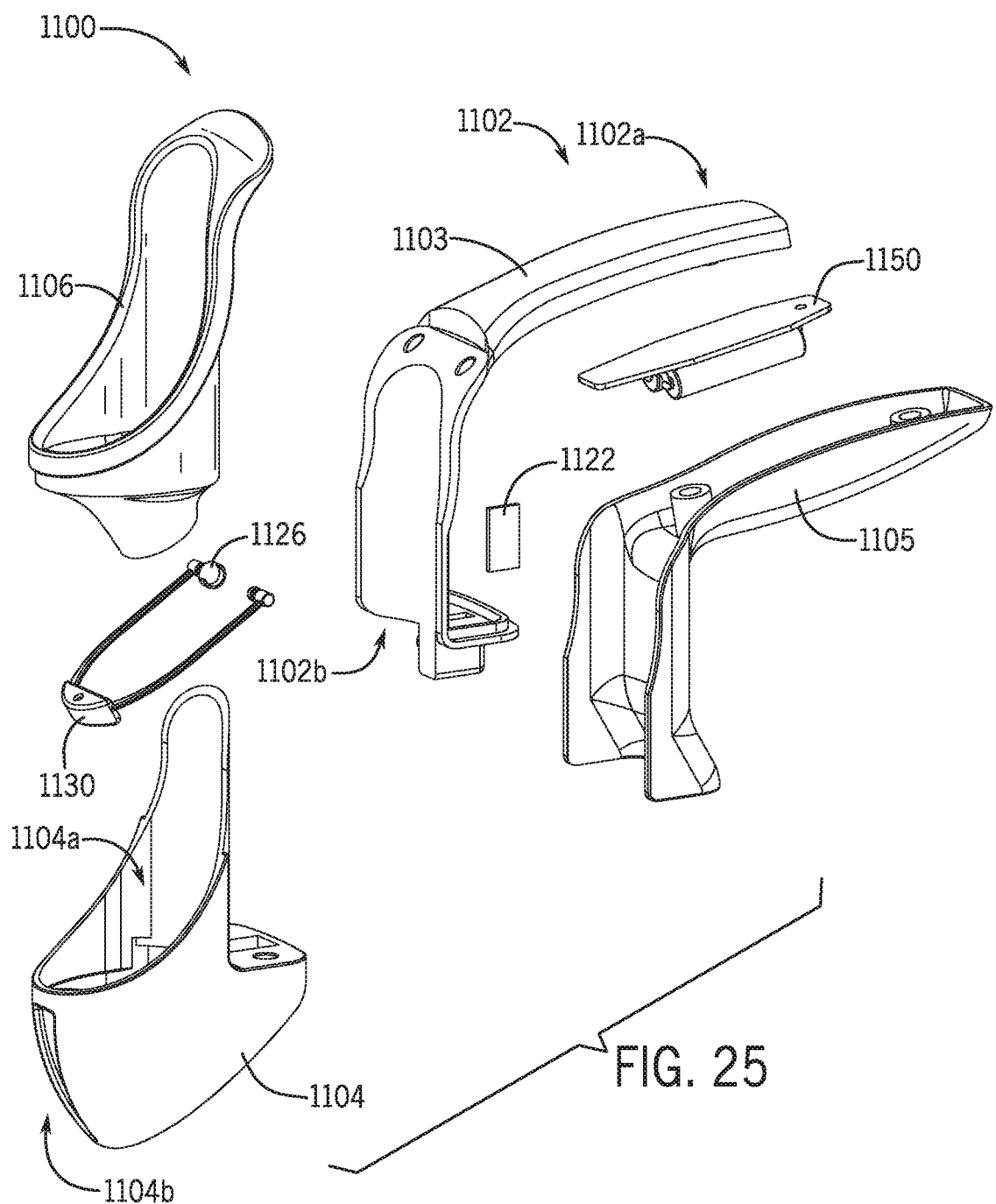
FIG. 25 is an exploded view of the uroflowmeter of FIG. 24 in accordance with various embodiments of the present disclosure.
Figure 26:
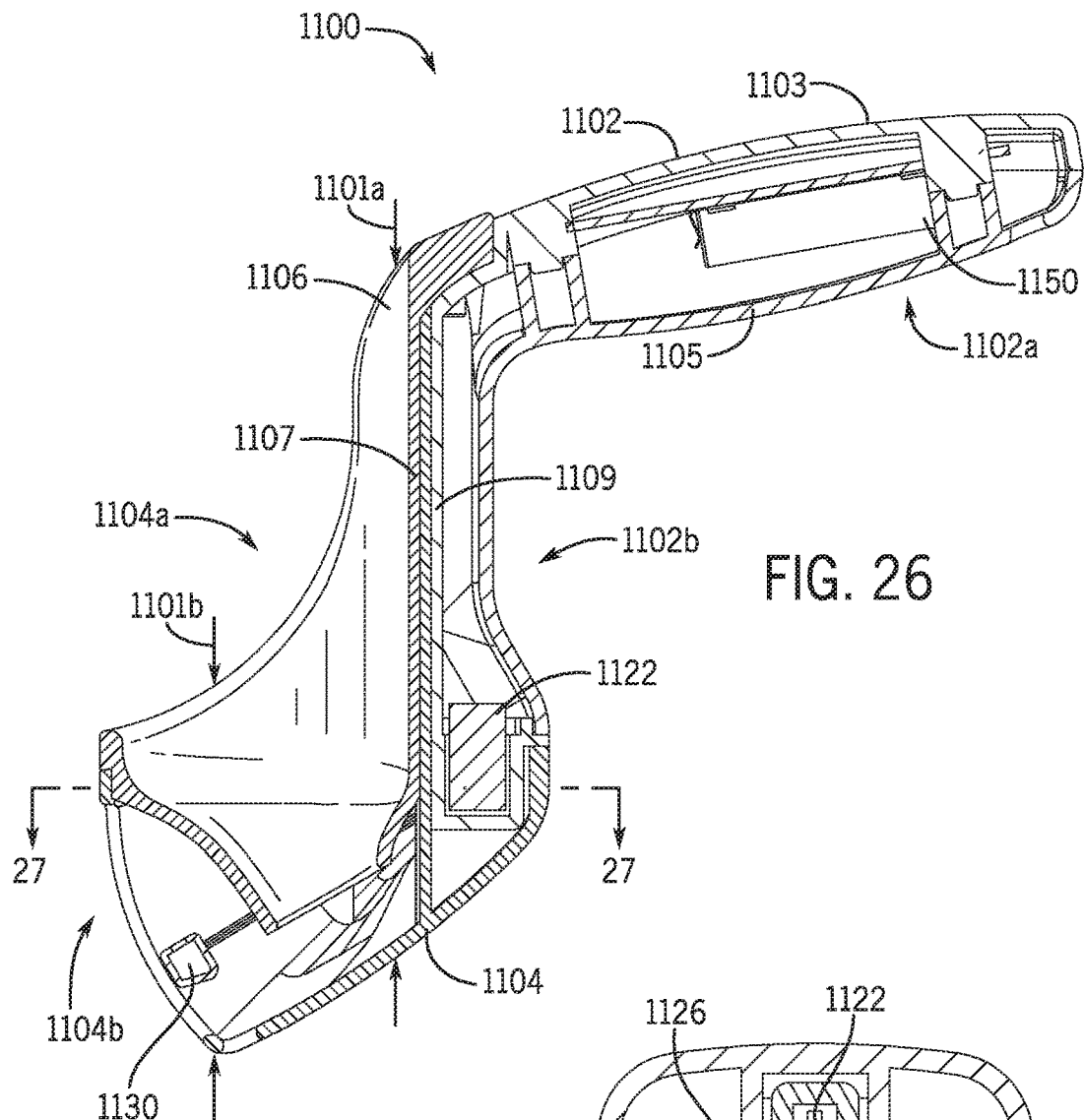
FIG. 26 is a cross-sectional view of the uroflowmeter of FIG. 24 taken along line 26-26 in accordance with various embodiments of the present disclosure.
Figure 27:
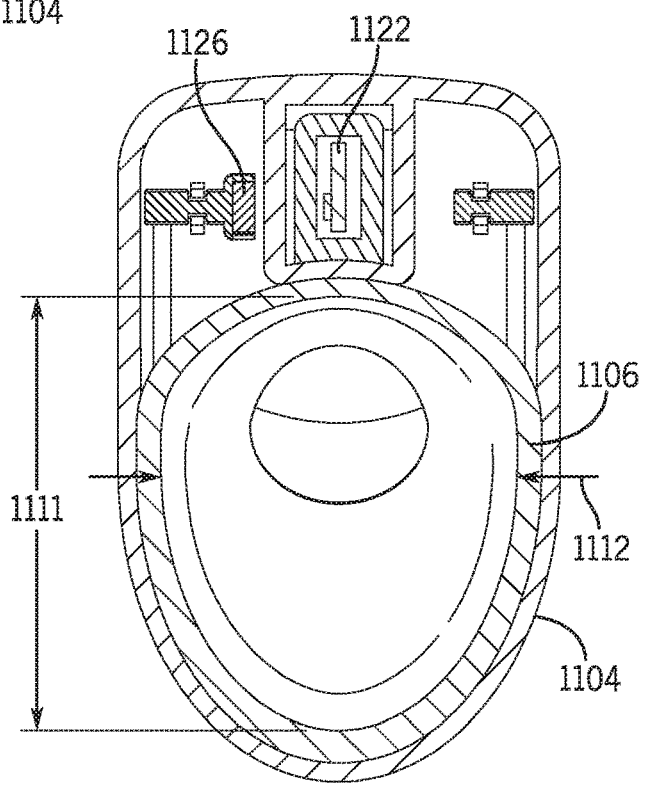
FIG. 27 is a cross-sectional view of the uroflowmeter of FIG. 26 taken along line 27-27 in accordance with various embodiments of the present disclosure.

FIG. 24 is a perspective view of another uroflowmeter 1100, FIG. 25 is an exploded view of the uroflowmeter 1100, and FIG. 26 is a longitudinal sectional view of the uroflowmeter 1100. As illustrated in FIGS. 24-27, the uroflowmeter 1100 includes a handle 1102, a bowl or flow chamber 1104, and a funnel 1106. The uroflowmeter 1100 generally includes the same or similar components and operates in the same manner as the uroflowmeter 100, and thus the description of the uroflowmeter 100, including the handle 102 and the flow chamber 104, is equally applicable to the uroflowmeter 1100, except as noted below.

As illustrated in FIGS. 24-27, the uroflowmeter 1100 may be configured for use by male patients. For example, as illustrated in FIG. 24, the funnel 1106 may include an elongated vertical backstop 1107 that may orientate or align anatomy of a male patient relative to the uroflowmeter 1100 in order to facilitate directing or guiding the male patient's urine into the inlet 1104a of the flow chamber 1104. To support the backstop 1107, the handle 1102 may be L-shaped. For example, as illustrated in FIG. 24, the handle 1102 may include a proximal portion 1102a and a distal portion 1102b oriented substantially perpendicular to the proximal portion 1102a. The distal portion 1102b of the handle 1102 may extend substantially coextensively with the vertical backstop 1107 to provide support to the backstop 1107. The proximal portion 1102a of the handle 1102 may provide an ergonomic grip for the patient to grasp.

The flow chamber 1104 may facilitate proper anatomic positioning of the uroflowmeter 1100 to receive urinary flow from a male patient. The flow chamber 1104 shown in FIGS. 26 and 27 has a width 1112 and a length 1111. The length 1111 may be greater than the width 1112 in order to define an exterior contour of the flow chamber 104. The flow chamber 104 may also have a height, such as the first height 1101a and the second height 1101b. The first height 1101a may be a height of the flow chamber 1104 adjacent the handle 1102 and the second height 1101b may be a height of the flow chamber 1104 adjacent the outlet 1104b. Generally, in the embodiment of FIGS. 26 and 27 one or both of the first height 107a or the second height 107b may be greater than the length 1111 and the width 1112. Further, the first height 1101a may be different than the second height 1101b, in order to define a contour of the backstop 1107.

As illustrated in FIGS. 25 and 26, the handle 1102 may include a top shell 1103 and a bottom shell 1105. The top and bottom shells 1103, 1105 may be attached together to define a hollow interior cavity for receiving electronics 1150 and/or sensor 1122, for example. The electronics 1150 may be received in the proximal portion 1102a of the handle 1102, and the sensor 1122 may be received in the distal portion 1102b of the handle 1102. The flow chamber 1104 may be attached to the distal portion 1102b of the handle 1102. For example, the flow chamber 1104 may be removeably attached to the distal portion 1102b of the handle 1102, thereby allowing the flow chamber 1104 and the funnel 1106 to be disposed after use while permitting the handle 1102 to be reused. As illustrated in FIG. 25, the flow chamber 1104 may include a vertical backstop 1109 that provides support to the vertical backstop 1107 of the funnel 1106. The vertical backstop 1107 may also be used to position correctly over the funnel.

During use, a patient may urinate into the inlet 1104a of the flow chamber 1104 via the funnel 1106, for example. The urine stream may travel into the flow chamber 1104 via the inlet 1104a and out of the flow chamber 1104 via the outlet 1104b. The sensor 1122 may detect the instantaneous fluid level in the flow chamber 1104 via the float 1130 and magnet 1126, similar to the arrangement described with respect to the uroflowmeter 100, and the fluid level data may be used to determine the urinary flow rate and the total volume of urine evacuated by the patient.

In FIGS. 24-27, the flow chamber 1104, the funnel 1106, and the float 1130 may be disposable, and the handle 1102 may be reusable. The respective components may be formed from various materials. For example, the funnel 1106 may be formed from rubber, and the handle 1102, the flow chamber 1104, and the float 1130 may be formed from plastic.

Figure 28:
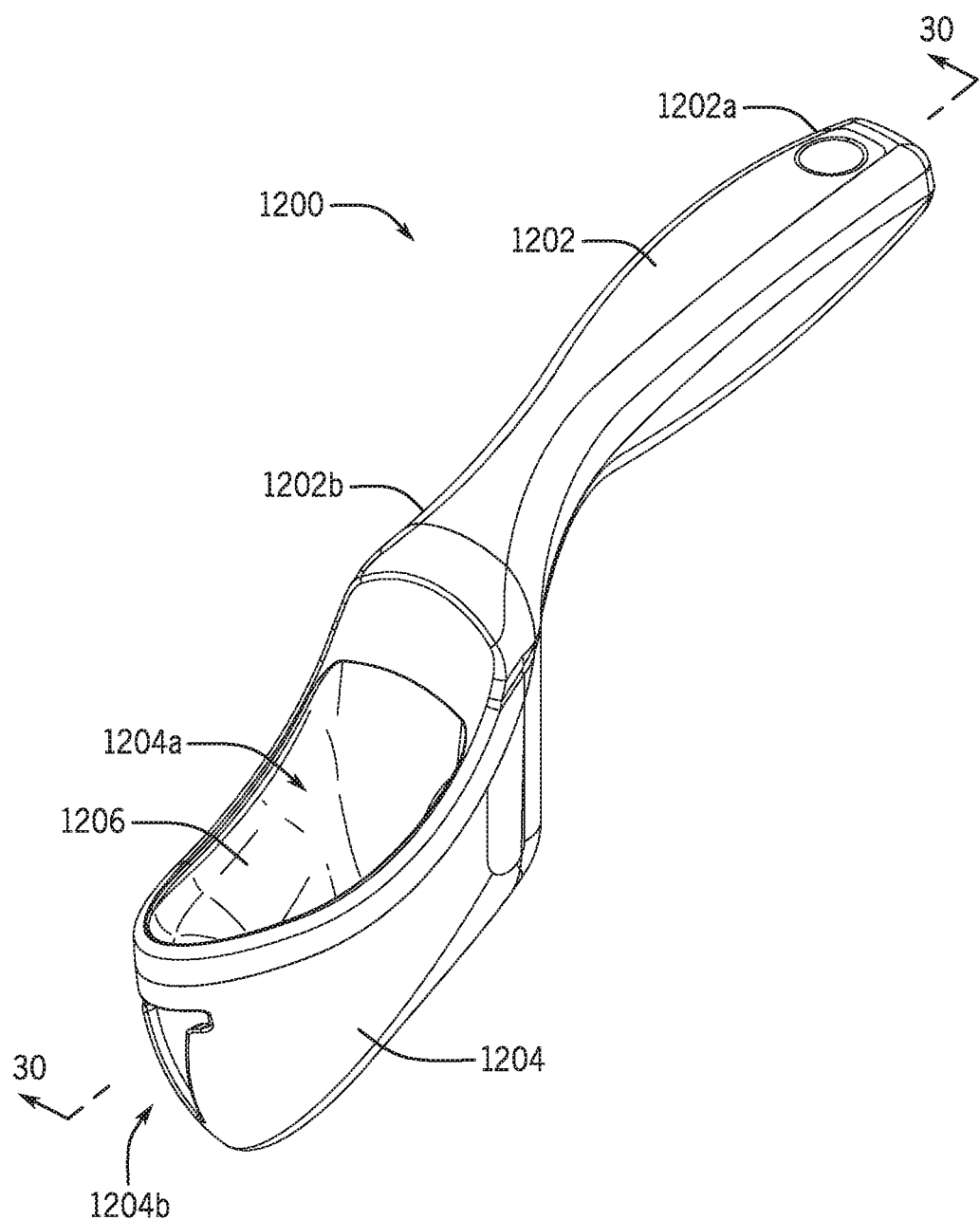
FIG. 28 is a perspective view of an alternative uroflowmeter in accordance with various embodiments of the present disclosure.
Figure 29:
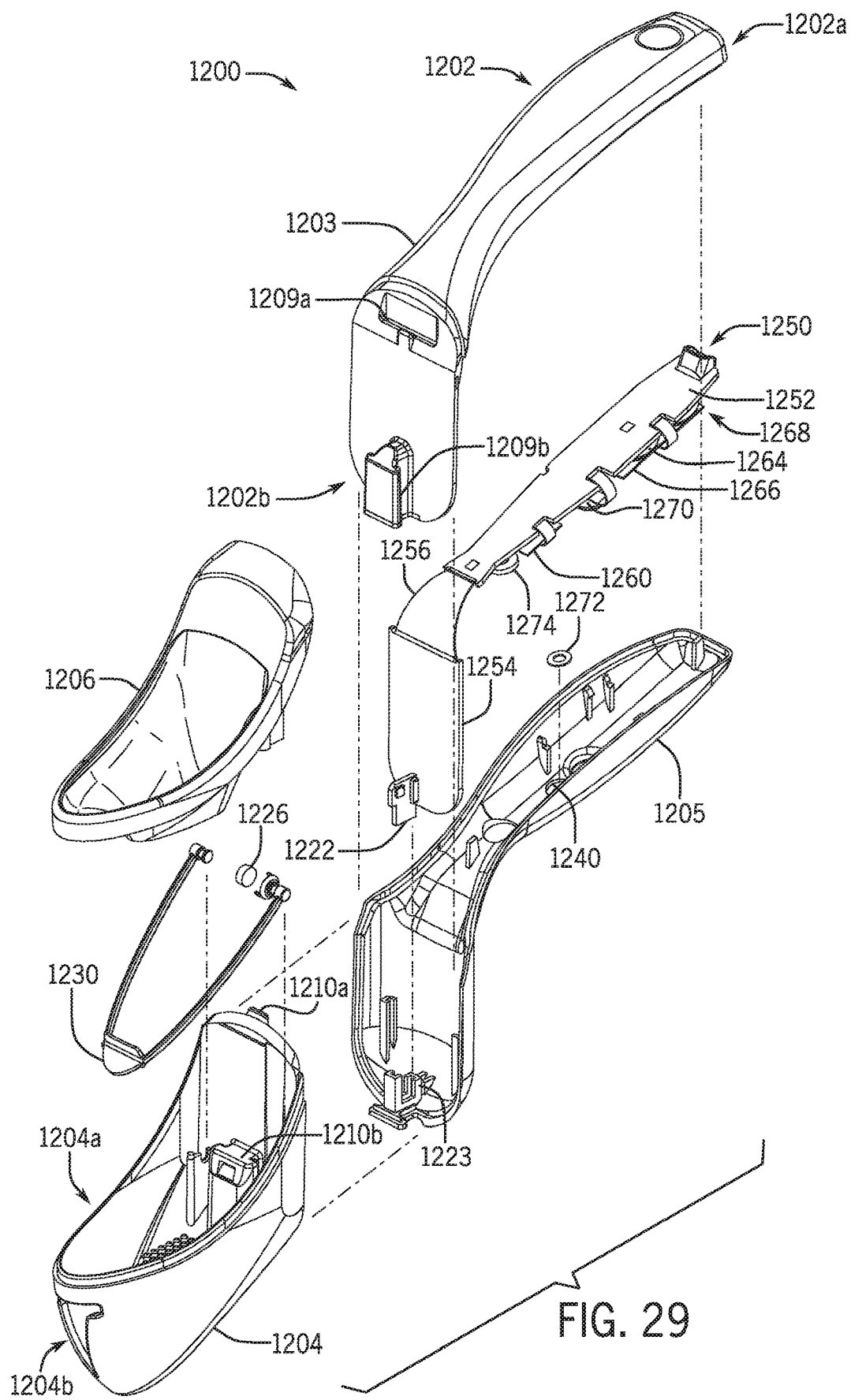
FIG. 29 is an exploded view of the uroflowmeter of FIG. 28 in accordance with various embodiments of the present disclosure.
Figure 30:
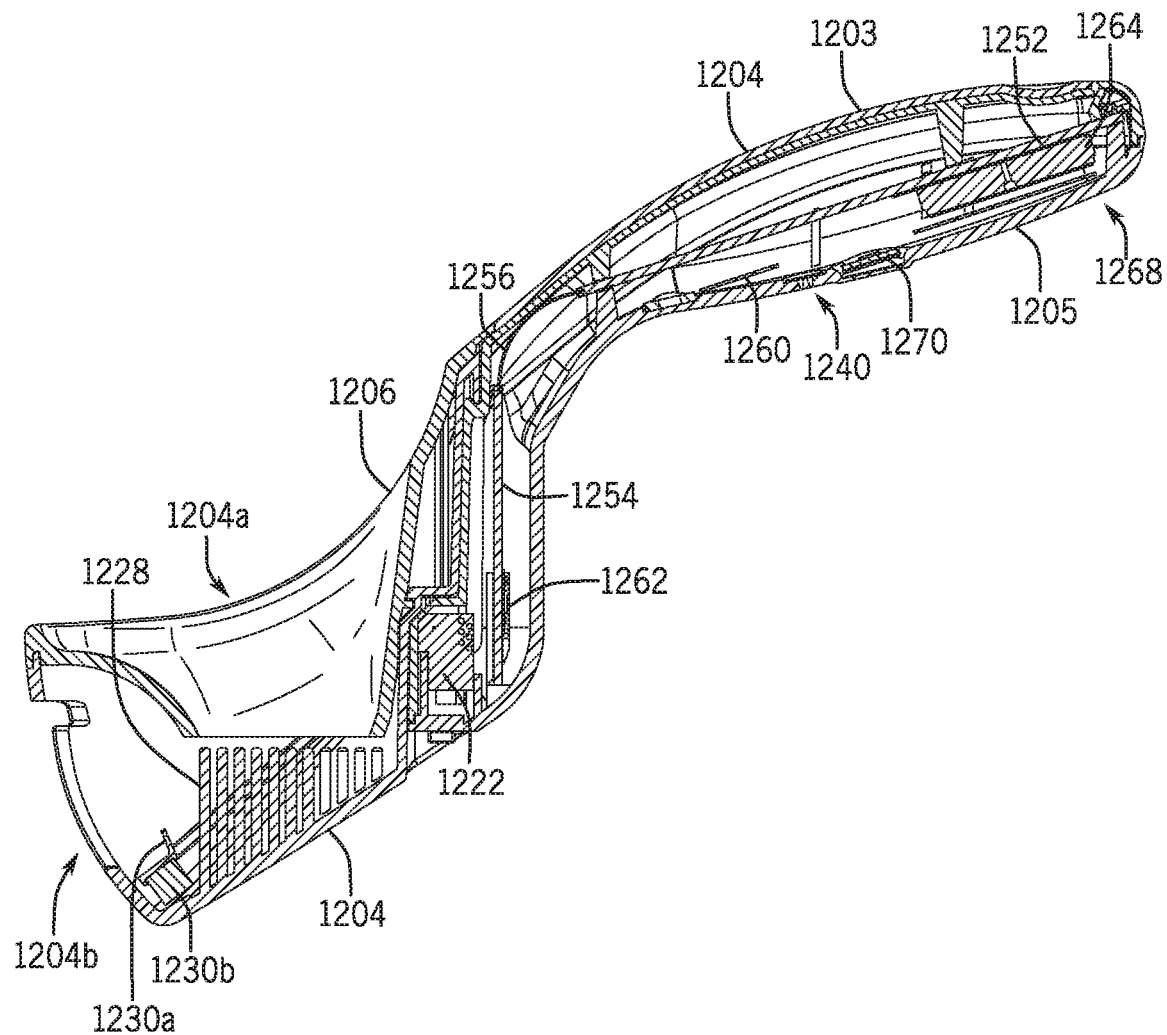
FIG. 30 is a cross-sectional view of the uroflowmeter of FIG. 28 taken along line 28-28 in accordance with various embodiment of the present disclosure.

FIG. 28 is a perspective view of another uroflowmeter 1200, FIG. 29 is an exploded view of the uroflowmeter 1200, and FIG. 30 is a cross-sectional view of the uroflowmeter 1200, taken along line 30-30 of FIG. 28. As illustrated in FIGS. 28-30, the uroflowmeter 1200 includes a handle 1202, a bowl or flow chamber 1204, and a funnel 1206. The uroflowmeter 1200 generally includes the same or similar components and operates in the same manner as the uroflowmeter 100, and thus the description of the uroflowmeter 100, is equally applicable to the uroflowmeter 1200. In this regard, substantially analogous to the embodiment of the uroflowmeter 100 described above, the uroflowmeter 1200 of FIGS. 28-30 further includes: a proximal portion 1202a, a distal portion 1202b, an inlet 1204a, an outlet 1204b, a magnet 1226, a float 1230, and a sensor 1222; redundant explanation of which is omitted here for clarity.

Notwithstanding the foregoing, the uroflowmeter 1200 includes energy dissipation features 1228. The energy dissipation features 1228 are shown positioned substantially within the flow chamber 1204. At least a portion of the energy dissipation features 1228 may be concealed by the funnel 1206 and at least another portion of the energy dissipation features 1228 may be visible and/or along or within the inlet 1204a. Broadly, the energy dissipation features 1228 may define a physical obstacle or obstruction for a flow of urine entering the flow chamber 1204 through the inlet 1204a. The energy dissipation features 1228 may have a size, shape, and contour that dissipates energy, e.g., kinetic energy, from the flow of urine. While many shapes are possible, in the embodiment of FIGS. 28-30, the energy dissipation features are shown as a collection of elongated cylinders. The elongated cylinders may generally extend from a bottom of the flow chamber 1204 toward the inlet 1204a. At the bottom of the flow chamber 1204, the elongated cylinders may generally be fixed, whereas near to the inlet 1204a each of the elongated cylinders may have a free end, allowed to deform, flex, sway, and so on. The elongated cylinders are separated from one another, thereby allowing flow among the collection of cylinders. In some cases, the elongated cylinders may have a taper or other contour that changes along a height of the cylinder.

The energy dissipation feature 1228 may facilitate urine level and flow detection. For example, the energy dissipation features 1228 may help reduce turbulent flow within the flow chamber 1204, for example, such as that which may be caused by a fluid flow impacting a stationary volume of fluid. In some cases, the energy dissipation features 1228 may also help mitigate fluid exit through the inlet 1204a. For example, the energy dissipation features 1228 may reduce kinetic energy of a flow of urine in a manner that arrests stray flow from exiting the uroflowmeter 1200 through the inlet 1204a, thereby facilitating smooth or uninterrupted operation of float 1230 and associated components.

As best shown in FIGS. 29 and 30, the uroflowmeter 1200 includes the float 1230 positioned within the flow chamber 1204. As described herein, the float 1230 moves within the flow chamber 1204 based on a volume of urine held therein. To facilitate the foregoing, the float 1230 is shown having a structural member 1230a and a buoyant member 1230b. The structural member 1230a may provide structural rigidity to the float 1230 and facilitate connection of the float 1230 to other components of the uroflowmeter 1200, such as pivoting arms. The buoyant member 1230b may be a floatable component of the float 1230 that exhibits one or more properties that allow the float 1230 to rise and fall with a volume of urine within the flow chamber 1204. As shown, the buoyant member 1230*b* is generally arranged below the structural member 1230*a*. In this manner, as the volume of urine increases, the buoyant member 1230*b* may rise. Upon rising, the buoyant member 1230*b* may, in turn, press up against the structural member 1230*a*, thereby causing it to rise within the flow chamber 1204. This dual component design may allow the float 1230 to exhibit buoyant properties while maintaining a structural rigidity and robustness that facilitates prolonged and repeated use.

Further, the embodiment of FIGS. 28-30 shows the uroflowmeter 1200 having the outlet 1204*b*. The outlet 1204*b* is generally defined by a T-shaped slot extending through an exterior wall of the flow chamber 1204. The outlet 1204*b* generally maximizes a volumetric range of the flow chamber 1204, across which high accuracy flow measurements may be obtained. For example, the outlet 1204*b* generally restricts flow from exiting the flow chamber 1204 when the flow chamber 1204 includes relatively little fluid. This may correspond to a lower flow rate of urine, and therefore the restriction of fluid exiting the flow chamber 1204 helps facilitate or increase the sensitivity of associated flow measurements in this configuration. As the volume of fluid in the flow chamber 1204 increases, the outlet 1204*b* reduces its fluid restriction, allowing an increasingly greater amount of fluid to exit. This may correspond to a higher flow rate of urine, at which less sensitivity in flow rate measurement may be required. The outlet 1204*b* also includes an elongated opening positioned above and connected to the triangular-shaped opening. This elongated opening may mitigate overflow or backflow conditions, for example, by allowing for additional fluid release when the flow chamber 1204 approaches capacity. It will be appreciated that the shape and arrangement of the outlet 1204*b* is depicted for purposes of illustration. In other embodiments, other shapes and arrangements of outlets are possible to facilitate the various functions of the uroflowmeter 1200 described herein.

As described herein, the uroflowmeters of the present disclosure may include detachable and optionally interchangeable components. For example, it may be desirable to have a handle that is detachable from a flow chamber. The flow chamber, for example, may be used by a patient over a course of treatment. When complete, the detachable handle may be removed from the flow chamber, and recycled and sanitized for use with a subsequent flow chamber for another patient's course of treatment.

While many structures are possible for providing a detachable handle and different embodiments are described herein, the uroflowmeter 1200 of FIGS. 28-31 shows an interlocking tongue and groove system for attaching and detaching the handle 1202 and the flow chamber 1204 from one another. By way of particular example and with reference to FIG. 29, the handle 1202 is shown exploded from the flow chamber 1204, revealing interlocking tongue and groove structures. The interlocking tongue and groove structures may allow the handle 1202 and the flow chamber 1204 to removably attach to one another without surplus fasteners, clips, pins, and so on, thereby streaming removable attachment.

With reference to FIG. 29, the handle 1202 is shown having a handle groove 1209*a* positioned near a topmost portion of the handle 1202 and at the distal portion 1202*b*. Further, the handle 1202 is shown having a handle tongue 1209*b* positioned near a bottommost portion of the handle 1202 and at the distal portion 1202*b*. The handle groove 1209*a* and the handle tongue 1209*b* may mate with complimentary features on the flow chamber 1204. For example, the flow chamber 1204 may include a flow chamber tongue 1210*a* and a flow chamber groove 1210*b*. The flow chamber tongue 1210*a* may be received by the handle groove 1209*a* and the flow chamber groove 1210*b* may receive the handle tongue 1209*b*.

Each of the mated flow chamber tongue 1210*a*/handle groove 1209*a* and the flow chamber groove 1210*b*/handle tongue 1209*b* may cooperate to restrain relative movement of the handle 1202 and the flow chamber 1204. For example, each mating of the flow chamber tongue 1210*a*/handle groove 1209*a* and/or the flow chamber groove 1210*b*/handle tongue 1209*b* may establish a physical obstruction, that blocks movement of the handle 1202 and/or the flow chamber 1204 along multiple directions. This may help mitigate unintentional separation the flow chamber 1204 and the handle 1202 from one another. In some cases, one or more features may define a friction fit between the handle 1202 and the flow chamber 1204 in order to further resist movement.

In addition to facilitating the removable attachment of the flow chamber 1204 and the handle 1202, the tongue and groove features may also facilitate operation of the sensor 1222, described herein. For example and with reference to FIGS. 29 and 30, the flow chamber groove 1210*b* may extend inwards, toward an inner volume of the flow chamber 1204. The sensor 1222 may be arranged substantially within the handle tongue 1209*b*, within an inner volume of the handle 1202 and seated within a sensor receiving feature 1223. Accordingly, when the handle 1202 and the flow chamber 1204 are attached to one another, the sensor 1222 is arranged in alignment with the magnet 1226 and other components positioned within the flow chamber 1204. This may facilitate operation of the sensor 1222, for example, by increasing a proximity of the sensor 1222 to the magnet 1226.

As described herein, the uroflowmeter 1200 may include electronics 1250. While many different components may be used to implement the operations of the uroflowmeter, as described herein, FIGS. 29 and 30 present a sample arrangement of components that define or are associated with the electronics 1250. Broadly, the electronics 1250 may include a first printed circuit board 1252 and a second printed circuit board 1254. The first printed circuit board 1252 and the second printed circuit board 1254 may be connected to one another by flex connectors 1256. In the embodiment of FIGS. 29 and 30, the first printed circuit board 1252 may be positioned within the handle 1202 near the proximal portion 1202*a* and the second printed circuit board 1254 may be positioned within the handle 1202 near the distal portion 1202*b*.

This dual circuit board arrangement may facilitate arranging components at different locations of the handle 1202 based on a target function. For example, the first printed circuit board 1252 may be positioned away from the flow chamber 1204 and be associated with battery operation, charging, and so on, whereas the second circuit board 1254 may be positioned closer to the flow chamber 1204 and be associated with sensors and operations of the flow chamber 1204. While the embodiment of FIGS. 28-30 shows the first printed circuit board 1252 and the second printed circuit board 1254 as separate circuit boards that are connected by the flexible connectors 1256, in other embodiments, other configurations are possible. For example, the first printed circuit board 1252 and the second printed circuit board 1254 may be portions of a single circuit board, such as a hybrid rigid/flexible circuit assembly having rigid portions and flexible portions. This single component or single assembly approach may facilitate reliability by reducing connections, and/or also reducing manufacturing costs.

In the embodiment of FIGS. 28-30, the first printed circuit board 1252 may be associated with at least a Radio-Frequency Identification ("RFID") element 1260, a battery 1264, an antenna 1266, a proximity sensor 1268, a charging coil 1270, a vent disc 1272, and/or other electrical mechanical components 1274. Further, the second printed circuit board 1254 may be associated with at least the sensor 1222 and a Subscriber Identity Module ("SIM") feature 1262. In other embodiments, other arrangements of components are contemplated to execute the functions of the uroflowmeter described herein, such as those in relation to FIGS. 6A-6C.

In some embodiments, the RFID element 1260 or other near field radio wave transmission or near field communication ("NFC") device, identification beacon, or the like, may facilitate reprocessing and tracking of the handle 1202. For example, the RFID element 1260 may include identifying information for the handle 1202, e.g., an identification number or data or the like. The identifying information may be used to associate the handle 1202 with a particular patient or a particular use of the uroflowmeter 1300. The identifying information may also be used to track the handle 1202 throughout reprocessing, including tracking the handle 1202 throughout a sanitization process. The identifying information may also facilitate real-time updates of inventory, such as being used to determine which units are in a condition for new patient-use, e.g., the units that have been reset to factory standards, sterilized, or otherwise processed as desired. Dynamic adjustments can therefore be made to facilitate inventory level maintenance, including initiating a resupply of handles, or other components, when the inventory drops below a threshold. For example, by periodically or randomly polling a supply of handles, such as with an RFID scanner, responses from the RFID or other element can be used to easily determine supply levels and categories of handles (e.g., awaiting processing, processed, etc.). In another example, a uroflowmeter is scanned by an RFID scanner when the uroflowmeter is associated or disassociated with a patient. The uroflowmeter status may then be stored in a server. The uroflowmeter may be scanned again when associated with a new patient, assigned to the same patient for a new study, the uroflowmeter is at the end of its life, or it is returned to the manufacturer.

Reprocessing may be facilitated by Global Positioning System ("GPS") localization of the handle 1202. In some embodiments, the handle 1202 may include a GPS assembly or other location sensor or element to facilitate determining a coordinate and/or relative position of the handle 1202. As described herein, the handle 1202 may be communicatively coupled with various remote computing systems. The GPS assembly of the handle 1202 may therefore determine information corresponding to a position of the handle 1202, which is in turn transmitted wirelessly to the remote computing system. The remote computing system may track the location of the handle 1202 and determine the handle 1202 being at one or more reprocessing, patient, healthcare provider, or other locations. The GPS assembly can be used to dynamically and automatically provide location information to the server, both during patient use and post processing. This may allow data to be automatically input into a patient use diary or other associated application that may provide additional metadata to be stored with patient voids.

FIGS. 29 and 30 also show the handle 1202 includes a vent 1240. The vent 1240 may define a path for air from an external environment to enter an internal volume of the handle 1202. This may include a barometric vent, for example, that allows for air pressure equalization between an internal volume of the handle 1202 and the external environment. The vent 1240 may generally allow infiltration of air, while block or mitigating the entrance of water or containments into the handle 1202. In this regard, the vent 1240 may define or be coupled with a water-proof or water-resistant barrier, such as that which may be defined by the vent disc 1272. The vent 1240 may also allow excess internal pressure relief in the event of battery off-gassing and/or other event in which pressure undesirably builds within the handle 1202.

Figure 31:
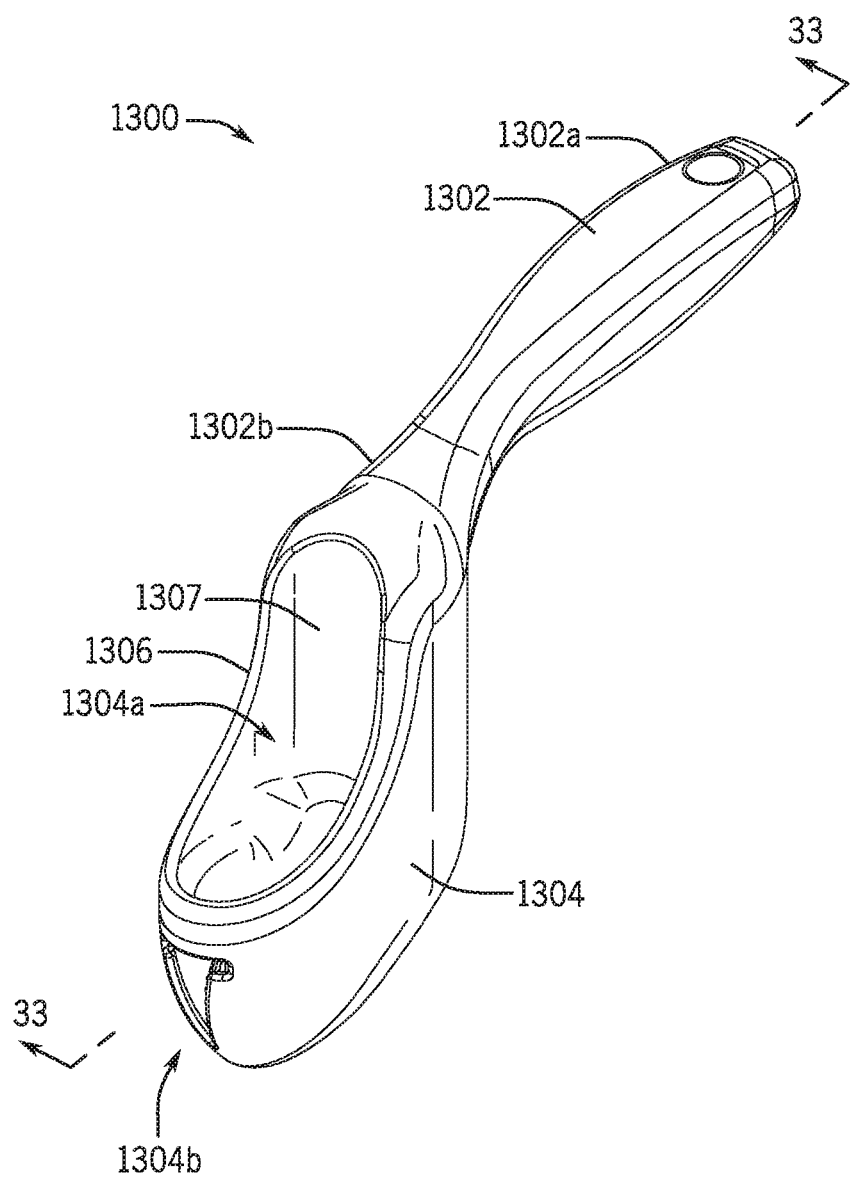
FIG. 31 is a perspective view of an alternative uroflowmeter in accordance with various embodiments of the present disclosure.
Figure 32:
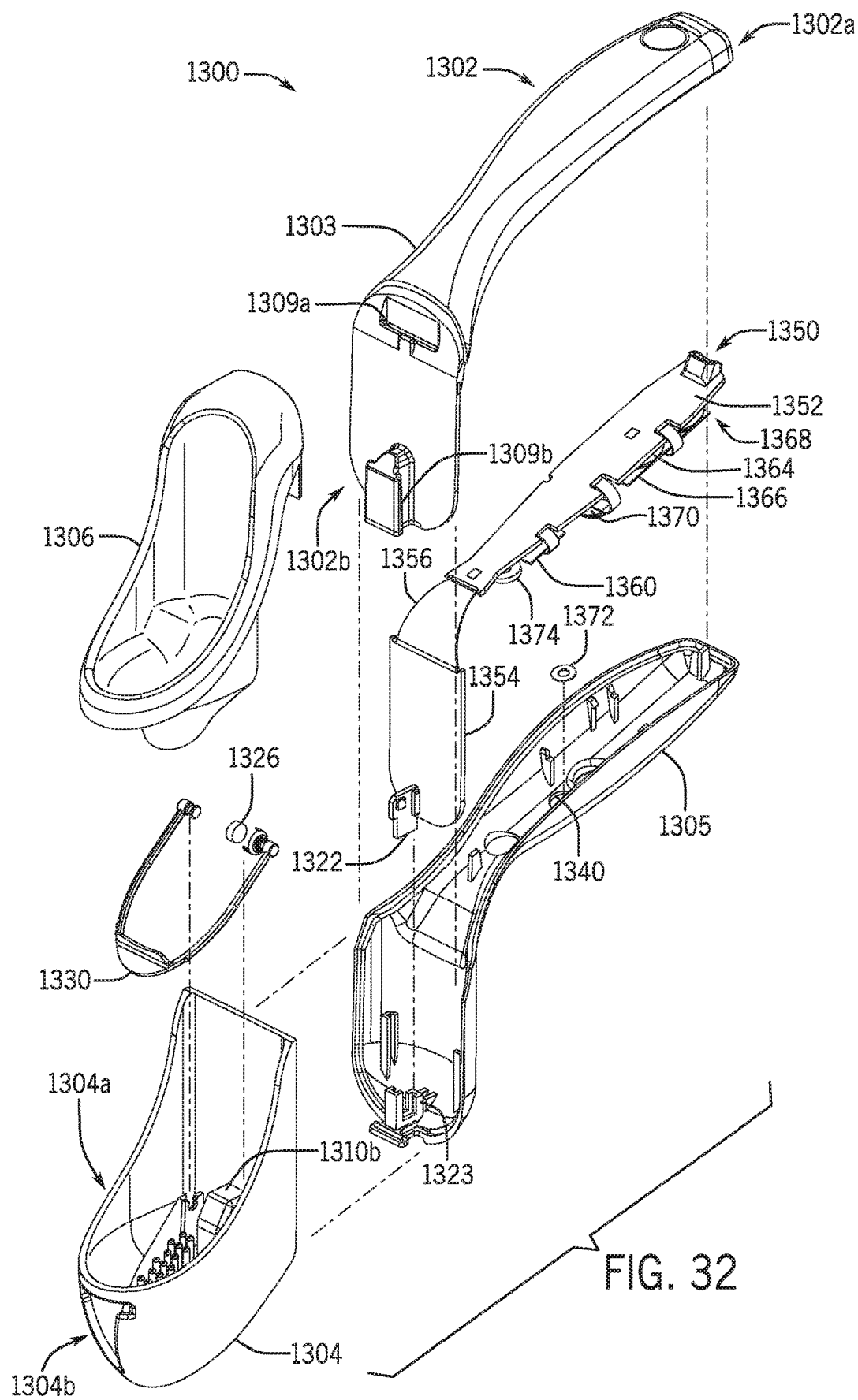
FIG. 32 is an exploded view of the uroflowmeter of FIG. 28 in accordance with various embodiments of the present disclosure.
Figure 33:
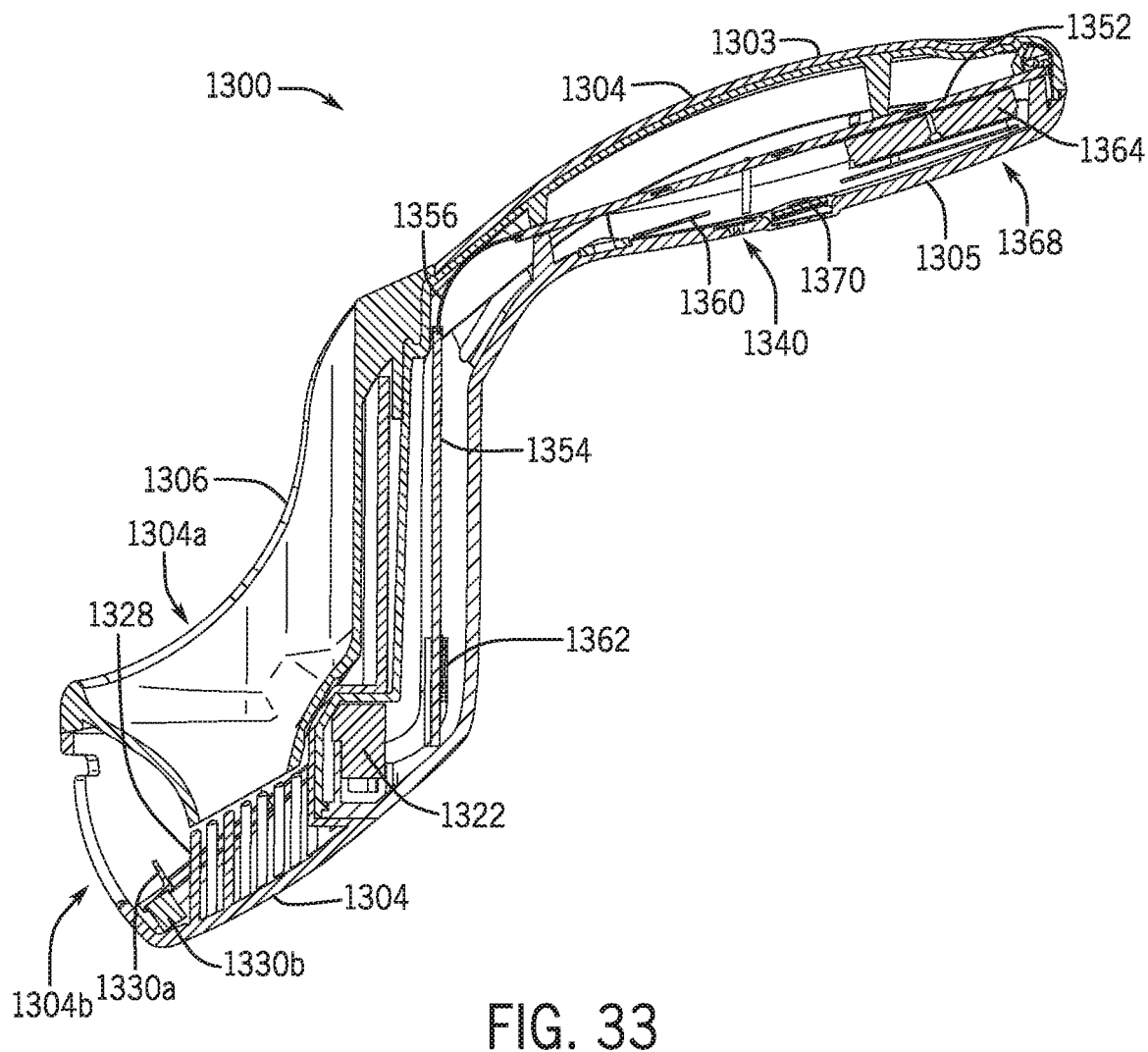
FIG. 33 is a cross-sectional view of the uroflowmeter of FIG. 30 taken along line 30-30 in accordance with various embodiment of the present disclosure.

The uroflowmeter 1200 may be configured for use by a female patient. With reference to FIGS. 31-33, another uroflowmeter 1300 is shown that is configured for use by male patients. FIG. 31 is a perspective view of the uroflowmeter 1300, FIG. 32 is an exploded view of the uroflowmeter 1300, and FIG. 33 is a cross-sectional view of the uroflowmeter 1300, taken along line 33-33 of FIG. 31.

As illustrated in FIGS. 31-33, the uroflowmeter 1300 includes a handle 1302, a bowl or flow chamber 1304, and a funnel 1306. The uroflowmeter 1300 generally includes the same or similar components and operates in the same or similar manner as the uroflowmeter 100 and 1200, and thus the description of the uroflowmeter 100 and the uroflowmeter 1200, is applicable to the uroflowmeter 1200. In this regard, substantially analogous to the embodiment of the uroflowmeter 1200 described above, the uroflowmeter 1300 of FIGS. 31-33 further includes: a proximal portion 1302*a*, a distal portion 1302*b*, a top shell 1303, an inlet 1304*a*, an outlet 1304*b*, a bottom shell 1305, a handle groove 1309*a*, a handle tongue 1309*b*, a flow chamber tongue 1310*a*, a flow chamber groove 1310*b*, a sensor 1322, a sensor receiving feature 1323, energy dissipation features 1328, a magnet 1326, a float 1330, a structural member 1330*a*, a buoyant member 1330*b*, a vent 1340, electronics 1350, a first printed circuit board 1352, a second printed circuit board 1354, flex connectors 1356, an RFID feature 1360, a SIM feature 1362, a battery 1364, an antenna 1366, a proximity sensor 1368, a charging coil 1370, a vent disc 1372, other electrical/mechanical components 1374; redundant explanation of which is omitted here for clarity. The structural member 1330*a* may be adapted to maintain accurate readings from the sensor 1322 during high periods of fluid flow. For example, the structural member 1330*a* may prevent urine flows from overrunning the top of the float assembly 1330, pushing it down, and impacting measurements.

Notwithstanding the foregoing similarities and as described above, the uroflowmeter 1300 is configured for use by a male patient. In this regard, the uroflowmeter 1300 includes an elongated vertical backstop 1307. The backstop 1307 may direct or guide the patient's urine into the inlet 1304*a* of the flow chamber 1304, for example, substantially analogous to that as described with respect to FIGS. 24-27. To support the backstop 1307, the handle 1302 may be L-shaped, as best shown in FIG. 32.

It will be appreciated that any of the uroflowmeters described herein may include a battery (e.g., battery 1264 of FIG. 29). The battery may be generally used to operate various electronics of the uroflowmeter, including a flow sensor and associated components, as described herein. To facilitate prolonged and/or multiple-patient use of the uroflowmeter, the battery may be rechargeable. While the battery may be recharged by a variety of techniques, in one embodiment, the battery is rechargeable using an inductive charging arrangement. An inductive charging arrangement permits charging the battery wirelessly, thereby allowing the uroflowmeter to maintain a sealed or water-resistant environment during charging.

Figure 34:
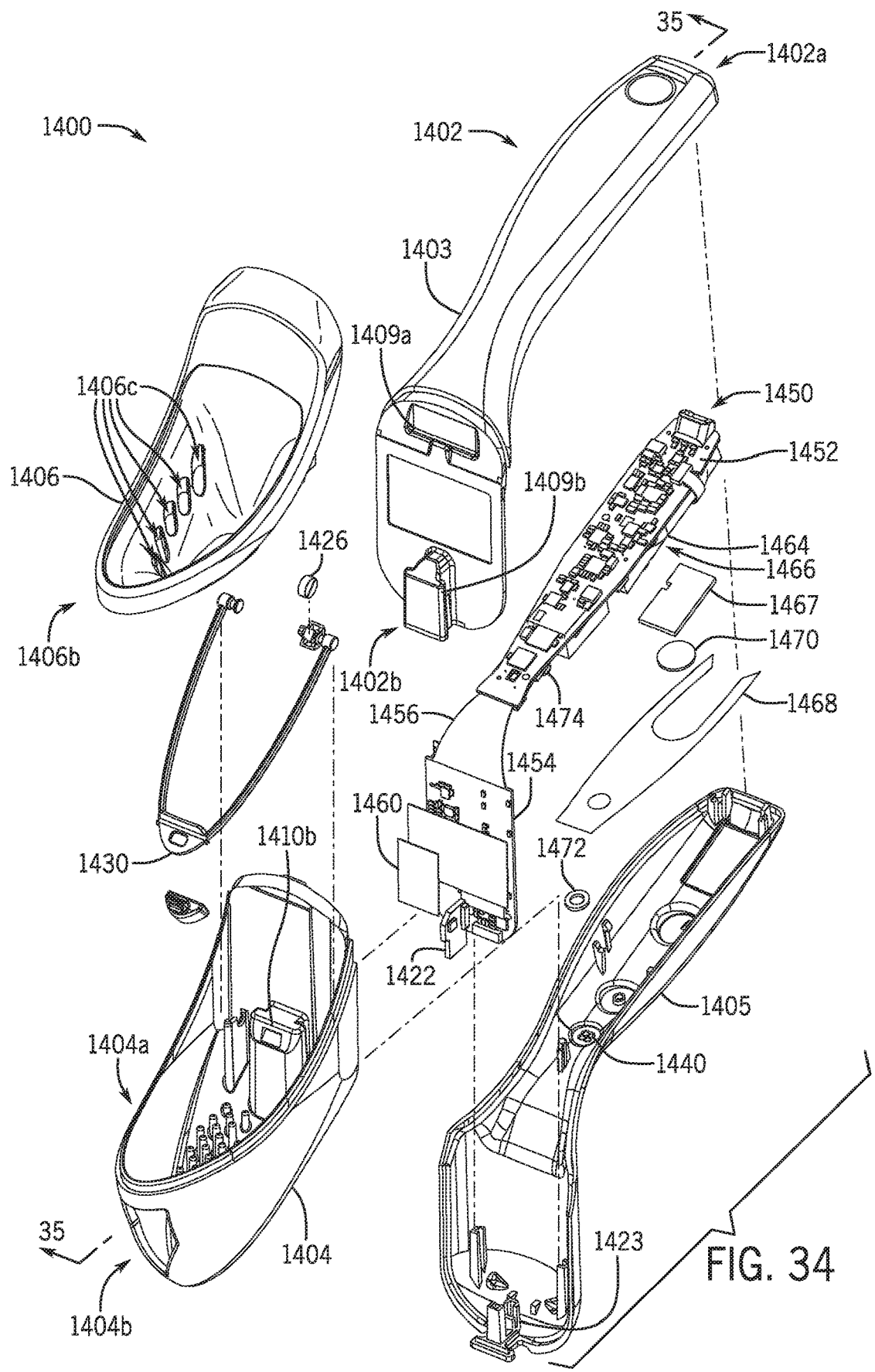
FIG. 34 is an exploded view of an alternative uroflowmeter in accordance with various embodiments of the present disclosure.
Figure 35:
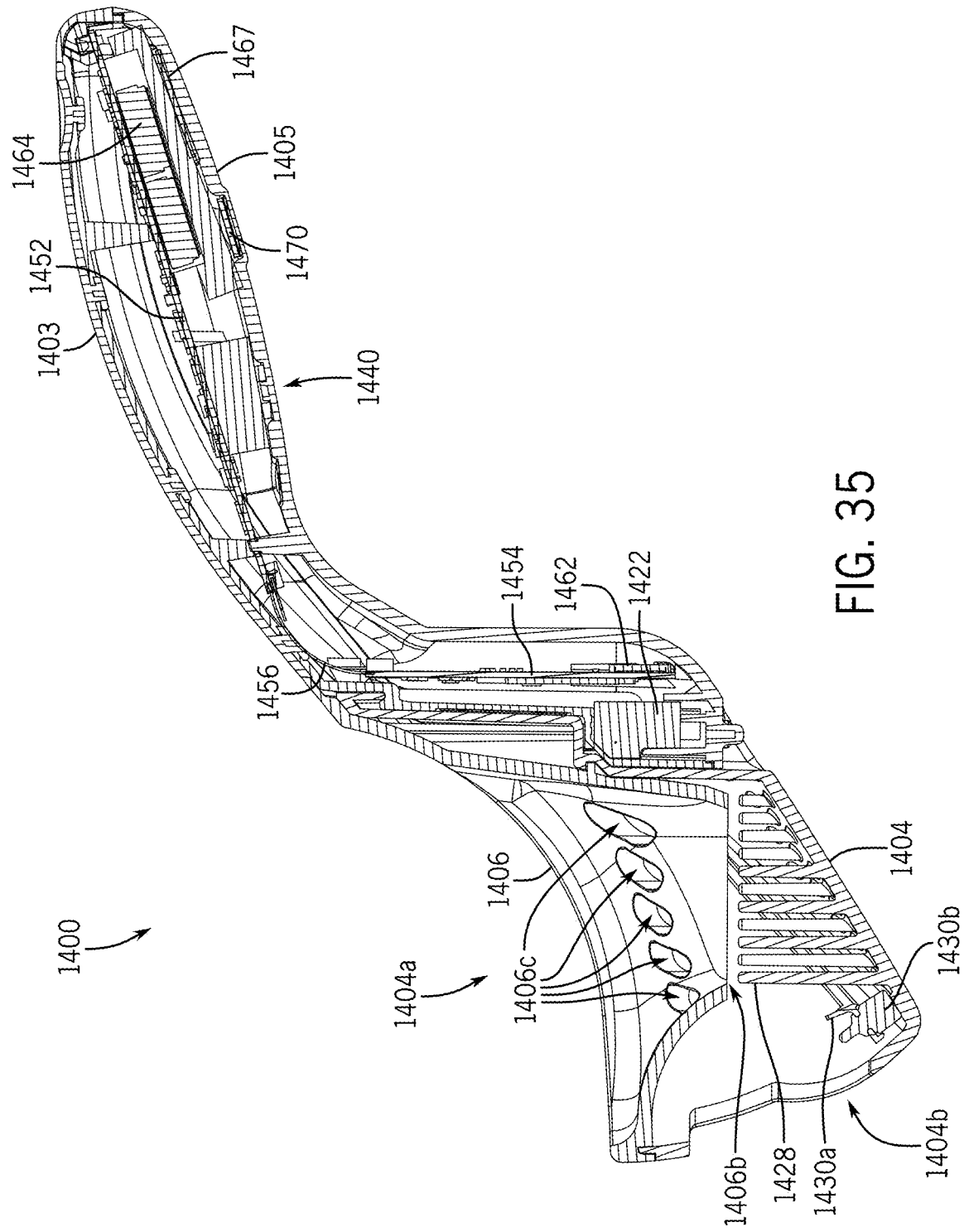
FIG. 35 is a cross-sectional view of the uroflowmeter of FIG. 34 taken along line 35-35 in accordance with various embodiment of the present disclosure.

With reference to FIGS. 34-35, a uroflowmeter 1400 is shown. FIG. 34 is an exploded view of the uroflowmeter 1400, and FIG. 35 is a cross-sectional view of the uroflowmeter 1400, taken along line 35-35 of FIG. 34.

As illustrated in FIGS. 34-35, the uroflowmeter 1400 includes a handle 1402, a bowl or flow chamber 1404, and a funnel 1406. The funnel 1406 includes one or more funnel inlets to allow fluid to pass from the funnel 1406 into the flow chamber 1404. The funnel inlets may be of any suitable shape and number to allow a smooth flow of fluid from the funnel 1406 into the flow chamber 1404. The funnel inlets may be in one configuration for male patients, and in a different configuration for female patients. In one example, the funnel 1460 has a primary funnel inlets 1406b. In another example, the funnel 1460 includes one or more secondary inlets 1406c. In one embodiment, the funnel includes five secondary inlets.

The uroflowmeter 1400 generally includes the same or similar components and operates in the same or similar manner as the uroflowmeter 100, 1200, and 1300, and thus the descriptions of the uroflowmeter 100, the uroflowmeter 1200, and/or the uroflowmeter 1300, are applicable to the uroflowmeter 1400. In this regard, substantially analogous to the embodiments of the uroflowmeter 1200 and/or 1300 described above, the uroflowmeter 1400 of FIGS. 34-35 further includes: a proximal portion 1402a, a distal portion 1402b, a top shell 1403, an inlet 1404a, an outlet 1404b, a bottom shell 1405, a handle groove 1409a, a handle tongue 1409b, a flow chamber tongue, a flow chamber groove 1410b, a sensor 1422, a sensor receiving feature 1423, energy dissipation features 1428, a magnet 1426, a float 1430, a structural member 1430a, a buoyant member 1430b, a vent 1440, electronics 1450, a first printed circuit board 1452, a second printed circuit board 1454, flex connectors 1456, an RFID feature 1460, a SIM feature 1462, a battery 1464, an antenna 1466, an NFC feature 1467, a proximity sensor 1468, a charging coil 1470, a vent disc 1472, other electrical/mechanical components 1474; redundant explanation of which is omitted here for clarity. The structural member 1430a may be adapted to maintain accurate readings from the sensor 1422 during high periods of fluid flow. For example, the structural member 1430a may prevent urine flows from overrunning the top of the float assembly 1430, pushing it down, and impacting measurements.

Figure 36:
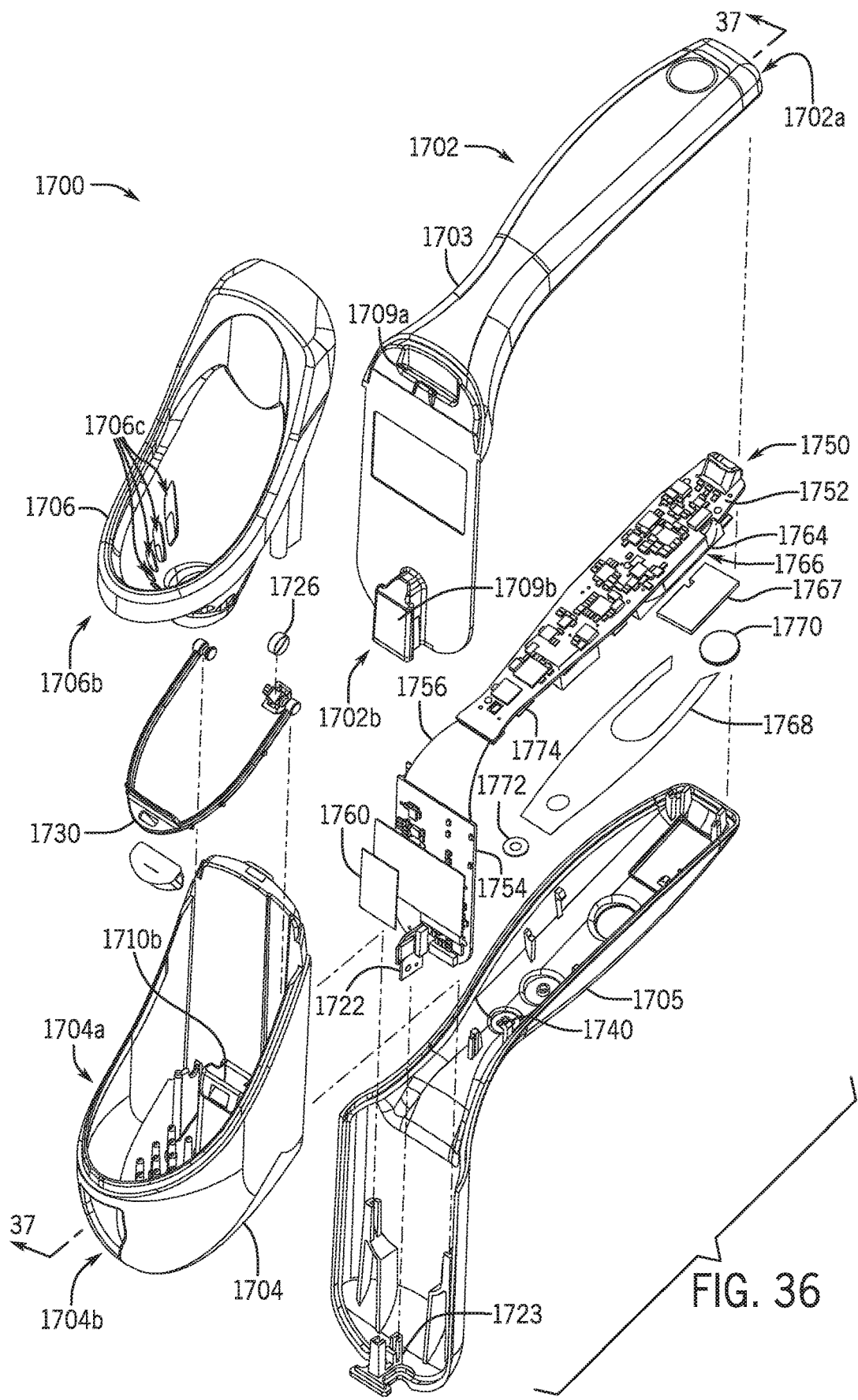
FIG. 36 is an exploded view of an alternative uroflowmeter in accordance with various embodiments of the present disclosure.
Figure 37:
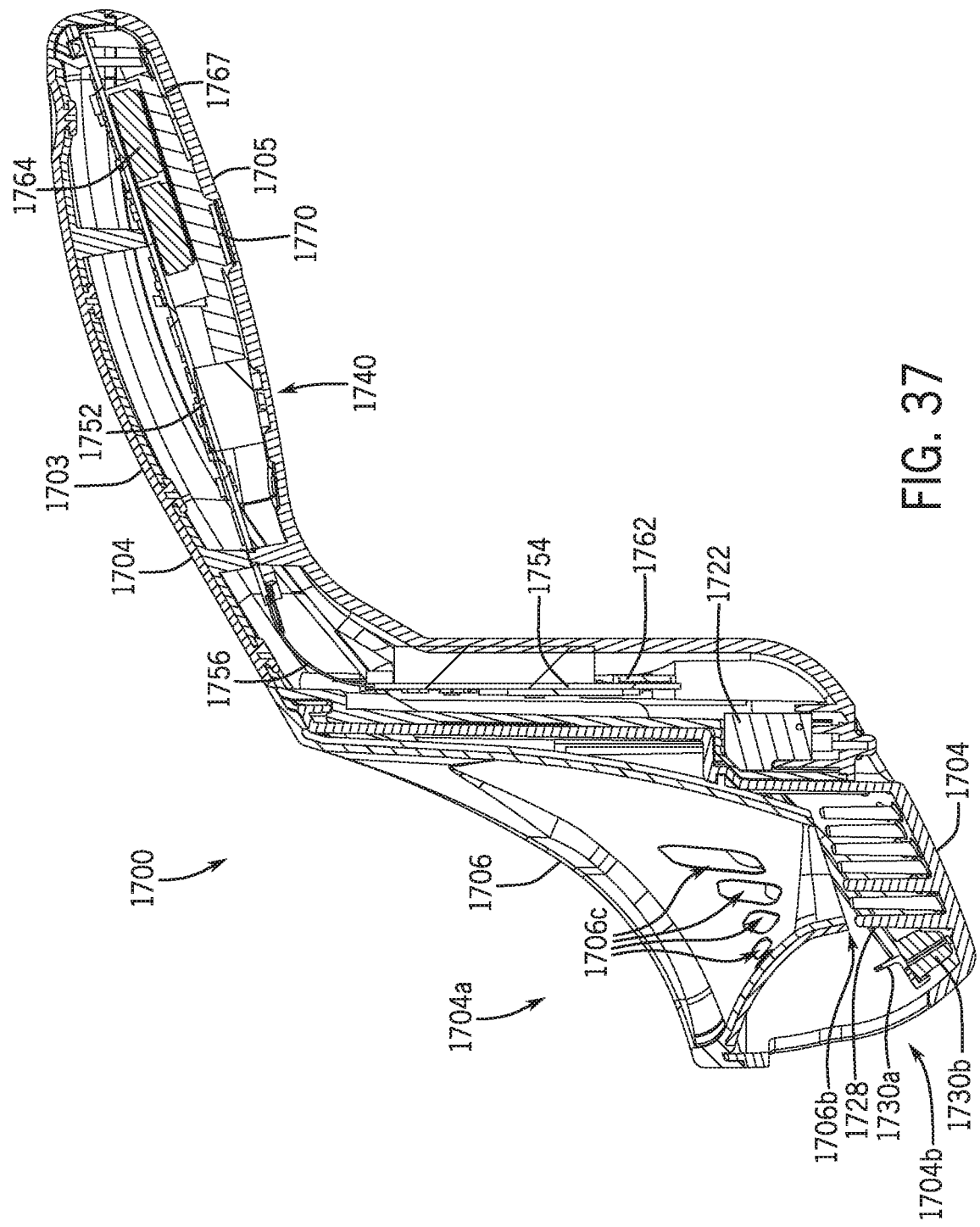
FIG. 37 is a cross-sectional view of the uroflowmeter of FIG. 36 taken along line 37-37 in accordance with various embodiment of the present disclosure.

With reference to FIGS. 36-38B, a uroflowmeter 1700 is shown. FIG. 36 is an exploded view of the uroflowmeter 1700, and FIG. 37 is a cross-sectional view of the uroflowmeter 1700, taken along line 37-37 of FIG. 36. FIG. 38A is a partial exploded view of the uroflowmeter 1700 of FIG. 36. FIG. 38B is a partial detailed view of the attachment between the flow chamber 1704 and the handle 1702 of the uroflowmeter 1700.

As illustrated in FIGS. 36-38B, the uroflowmeter 1700 includes a handle 1702, a bowl or flow chamber 1704, and a funnel 1706. The funnel 1706 includes one or more funnel outlets to allow fluid to pass from the funnel 1706 into the flow chamber 1704. The funnel outlets may be of any suitable shape and number to allow a smooth flow of fluid from the funnel 1706 into the flow chamber 1704. The funnel outlets may be in one configuration for male patients, and in a different configuration for female patients. In one example, the funnel 1760 has a primary funnel outlet 1706b. In another example, the funnel 1760 includes one or more secondary outlets 1706c. In one embodiment, the funnel includes five secondary outlets.

The uroflowmeter 1700 generally includes the same or similar components and operates in the same or similar manner as the uroflowmeter 100, 1200, 1300 and 1400, and thus the descriptions of the uroflowmeter 100, the uroflowmeter 1200, the uroflowmeter 1300, and/or the uroflowmeter 1400, are applicable to the uroflowmeter 1700. In this regard, substantially analogous to the embodiments of the uroflowmeter 100, 1200, 1300, and/or 1400 described above, the uroflowmeter 1700 of FIGS. 36-38B further includes: a proximal portion 1702a, a distal portion 1702b, a top shell 1703, an inlet 1704a, an outlet 1704b, a bottom shell 1705, a handle groove 1709a, a handle tongue 1709b, a flow chamber tongue, a flow chamber groove 1710b, a sensor 1722, a sensor receiving feature 1723, energy dissipation features 1728, a magnet 1726, a float 1730, a structural member 1730a, a buoyant member 1730b, a vent 1740, electronics 1750, a first printed circuit board 1752, a second printed circuit board 1754, flex connectors 1756, an RFID feature 1760, a SIM feature 1762, a battery 1764, an antenna 1766, an NFC feature 1467, an NFC feature 1767, a proximity sensor 1768, a charging coil 1770, a vent disc 1772, other electrical/mechanical components 1774; redundant explanation of which is omitted here for clarity. The structural member 1730a may be adapted to maintain accurate readings from the sensor 1722 during high periods of fluid flow.

FIG. 38A illustrates the embodiment of FIG. 36, where the flow chamber 1704 of the uroflowmeter 1700 is removably attached to the handle 1702, thereby allowing the flow chamber 1704 to be disposed of after patient use. In various embodiments, the uroflowmeter 1700 does not include a disposable funnel. As illustrated for example in FIGS. 38A-B, the flow chamber 1704 may have one or more grasping features 1778a and 1778b that grasp cooperating features of the handle 1702. In one example, the grasping features 1778a, 1778b are springs including a cantilevered section 1784 separated from the body of the flow chamber 1704 by a clearance 1788. In the example, the grasping features 1778a, 1778b include a tang 1786. When the grasping features 1778a, 1778b are in a relaxed position, the tangs 1786 grasp corresponding features of the handle, preventing a user from decoupling the flow chamber 1704 and the handle 1702. The flow chamber 1704 and the handle 17-2 may be decoupled with the use of a key 1776. The key 1776 may be available to medical professionals, or other authorized users, and not available to patients. The key 1776 may include a handle 1792 connected to a shaft 1790, a pivot 1782 defined at one of the shaft 1790, and one or more decouplers 1780a, 1780b disposed radially about the pivot 1782. The one or more decouplers 1780a, 1780b cooperate with the one or more grasping features 1778a, 1778b to allow a medical professional or other authorized user to decouple the flow chamber 1704 and the handle 1702 of the uroflowmeter 1700. In one example, a medical professional inserts the key 1776 into the uroflowmeter 1700 such that the pivot 1782 cooperates with a pin or other cooperating feature in the uroflowmeter 1700 or the handle 1702. The medical professional may rotate, or twist the key 1776 as shown for example by the directional arrow in FIG. 38B, causing the one or more decouplers 1780a, 1780b to press against the one or more grasping features 1778a, 1778b, flexing the cantilevered section 1784 and causing the tang 1786 to disengage from the handle 1702. The medical professional may then slide the flow chamber 1704 away from the handle 1702. The medical professional may then dispose of, or disinfect and process for reuse, the flow chamber 1704. The medical professional may then reprocess the handle 1702 for reuse as previously described. The key 1776 and associated features of the handle 1702 that prevent user decoupling of the handle 1702 and the flow chamber 1704 are shown with respect to the example of the uroflowmeter 1700, in FIGS. 38A-B for example and illustration purposes. The key and these or similar features are equally applicable to, and may be included in, any uroflowmeter disclosed herein, including the uroflowmeter 100, 200, 300, 400, 500, 600, 700, 800, 900, 1000, 1100, 1200, 1300, 1400, and/or 1700.

Figure 39:
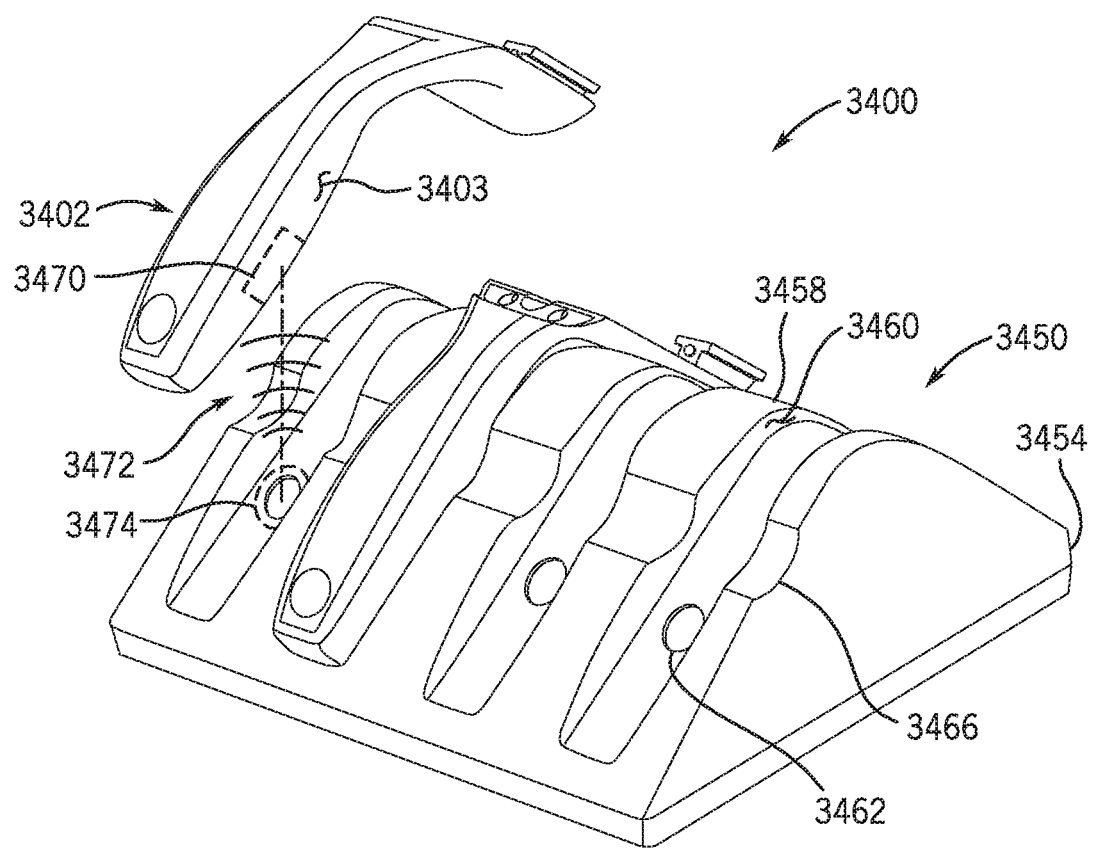
FIG. 39 depicts uroflowmeter handles and a sample charging station.

FIG. 39 depicts an example system 3400 including uroflowmeters configured for inductive charging and a charging station 3450 to facilitate the charging. Electronics of the uroflowmeters described herein, including rechargeable batteries, are arranged in a reusable and detachable handle of the uroflowmeter. In this regard, FIG. 39 depicts handle 3402 of a sample uroflowmeter that is associated with a charging station 3450. Broadly, the charging station 3450 may wirelessly charge a battery or other component of the handle 3402. While the handle 3402 is shown detached from a flow chamber or other single-patient feature, it will be appreciated that the uroflowmeter may be wirelessly or inductively charged in a condition where such features are attached to the handle 3402.

To facilitate the foregoing, the charging station 3450 may inductively charge a battery of the handle 3402. For example, the charging station 3450 may have an internal charging station component 3474, such as an induction coil, that is used to generate an electromagnetic field 3472 having various characteristics. The handle 3402 may have an internal handle component 3470, such as an induction coil (e.g., charging coil 1270 of FIG. 29). The internal handle component 3470 may use the electromagnetic field 3472 in order to charge the battery of the handle 3402 with electric current.

While the inductive charging arrangement of FIG. 39 may be accomplished in a variety of manners, the handle 3402 may generally be in a condition for charging as it is positioned closer to the charging station 3450. In this regard, the charging station 3450 may be constructed in a manner to facilitate arrangement and holding of the handle 3402 during inductive charging. In the embodiment of FIG. 39, the charging station 3450 includes a base 3454. The base 3454 may define a housing that enclose electronics of the charging station 3450, such as the internal charging component 3474. The base 3454 may also define an exterior surface that receives and/or aligns the handle 3402. For example, the base 3454 may include handle receiving portion 3458. The handle receiving portion 3458 may have a contour 3460 that matches a contour 3403 of the handle 3402. In this manner, the handle 3402 may be cradled and supported by the base 3454 during charging. In some cases, the handle receiving portion 3458 may define a friction fit with the handle 3402.

In addition to supporting the handle 3402, the charging station 3450 may also define features for aligning the handle 3402 with inductive charging elements of the charging station 3450. As shown in FIG. 39, the base 3454 includes alignment features 3462 generally arranged within the handle receiving portions 3458. The alignment features 3462 may be detents, grooves, protrusions, or other features that engage with complimentary features on the handle 3402. The alignment features 3462 may be associated with the internal charging station component 3474 and the complimentary features may be associated with the internal handle component 3470. In this manner, when the handle 3402 is positioned substantially within the handle receiving portion 3458, internal coils or other elements may be in close proximity to one another, thereby facilitating inductive charging. The charging station 3400 may include one or more recesses 3466 formed therein such that when a handle 3402 is received in the charging station 3400, the recesses 3466 provide a clearance between the handle 3402 and the charging station 3400, for example to facilitate gripping of a handle 3402 to remove it from the charging station.

Additionally and/or alternatively to facilitating wireless charging of the handle 3402, the charging station 3450 may be used to communicatively coupled the handle 3402 with one or more computing systems (e.g., computing system of FIG. 6A). For example, the internal handle component 3470 and the internal charging station component 3474 may be elements of an radio frequency ("RF") communication arrangement that cooperate to provide bi-directional communication between the handle 3402 and the charging station 3450, which may include or be associated with an external computing system. This bi-direction communication may allow the charging station 3450 to provide updates to the handle 3402. This may include firmware updates for the various electronic components of the handle 3402, diagnostic programs, or other information. The bi-directional communication may also allow the handle 3402 to provide updates to the charging station 3450. This may include information associated with a status of the handle 3402 among other information. The communication may also include the transfer of data associated with a void event, (e.g., data captured by the processing element 152 from one or more validation sensors 160, and/or the fluid level sensor 162) from the uroflowmeter to the charging station 3450, and then on to other devices, such as the server environment 2008 (see, FIG. 6C).

The example of FIG. 39 shows the charging station 3450 including four handle receiving portion 3458 for purposes of illustration. In other cases, the charging station 3450 may include more or less handle receiving portions. Further, while the system 3400 shows a single charging station 3450, in some embodiments, multiple charging stations 3450 may be associated with one another to facilitate charging of multiple handles simultaneously.

In another example, a server, such as the server 2008 may monitor remaining battery life of a uroflowmeter, which is regularly communicated from the device. If the battery becomes so low that measurements cannot be collected and transmitted, an indicator, such as the LED may indicate such a condition, and a notification may be sent to a health care provider device, such as a tablet. In another example, if the battery is no longer able to be recharged while docked on the charging station, the uroflowmeter, the server 2008, or other device may indicate a fault. The faulty uroflowmeter may be removed from service so it cannot be assigned to a patient.

Figure 40:
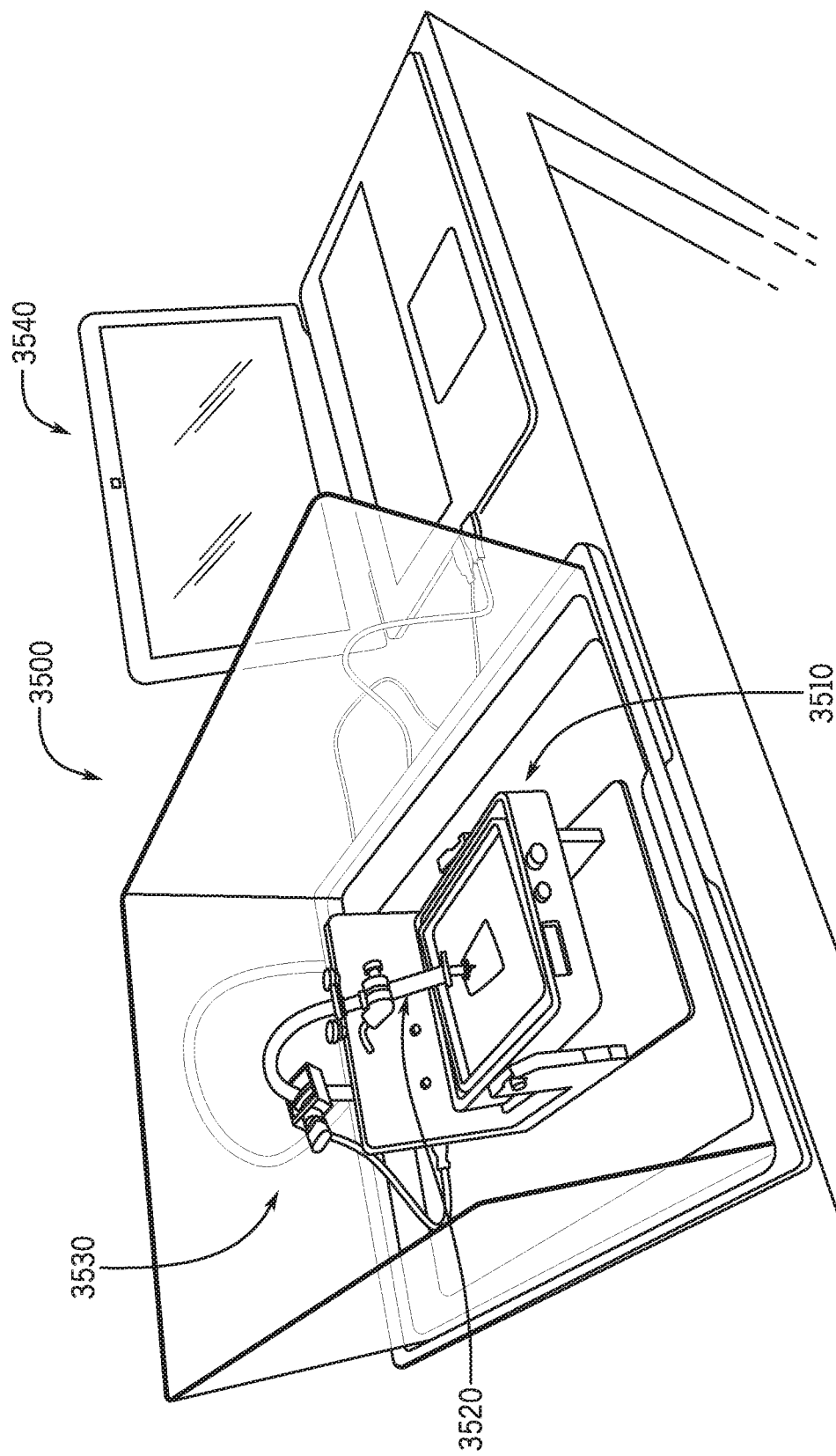
FIG. 40 depicts a test lab set up that may be used to test a uroflowmeter.

The uroflowmeters as disclosed herein may be developed and tested in a test lab set-up or system developed specifically for uroflowmeters. As shown in FIG. 40, the test lab system 3500 may include a well and adjustable reservoir (flow chamber) frame 3510, one or more adjustable nozzles 3520, a peristaltic pump 3530, a reference flow meter, and a computing device, such as a personal computer ("PC") 3540 in communication with the system to adjust the parameters and components to test the flow chamber. The test lab is used to design and improve a uroflowmeter, such as the uroflowmeter described herein. For example, the flow chamber of an exemplary uroflowmeter may be generated on a 3D printer, fitted with exemplary level sensors, and placed in the well. The frame may be adjusted for orientation angle (pitch/roll, or xz/yz planes). The nozzle may be adjusted for inflow angle, position, and stream shape. The PC controls the pump while reading the reference flow meter and the exemplary fluid level sensors, then processes data to calculate flow rate, and compare it to the rate reported by the reference flow meter. The test lab system may also be fitted with motors so that adjustable parameters (e.g., pitch and roll) can be controlled programmatically and testing can be automated.

The above specifications, examples, and data provide a complete description of the structure and use of exemplary embodiments of the invention as defined in the claims. Although various embodiments of the disclosure have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as only illustrative of particular embodiments and not limiting. Changes in detail or structure may be made without departing from the basic elements of the invention as defined in the following claims.

All relative and directional references (including: upper, lower, upward, downward, left, right, leftward, rightward, top, bottom, side, above, below, front, middle, back, vertical, horizontal, and so forth) are given by way of example to aid the reader's understanding of the particular examples described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

What is claimed is:

1. A portable handheld uroflowmeter comprising:
   a flow chamber configured to receive a direct flow of urine and continuously discharge the urine through an outlet defined in the flow chamber as the urine is received;
   a handle detachably coupled to the flow chamber and configured to selectively position the flow chamber to receive the flow of urine;
   a magnet associated with the flow chamber and configured to move in response to the flow or a level of urine in the flow chamber;
   a sensor adjacent the magnet and configured to detect a movement of the magnet;
   a buoyant float within the flow chamber, the buoyant float positionable according to the level of urine within the flow chamber; and
   an arm connecting the buoyant float and the magnet, such that a change in a position of the buoyant float causes the movement of the magnet in response to the level of urine in the flow chamber.

2. The portable handheld uroflowmeter of claim 1, wherein:
   the arm and the magnet are connected to one another about a pivot axis;
   the magnet rotates about the pivot axis in response to movement of the float; and
   the sensor further detects a change in an angular position of the magnet.

3. The portable handheld uroflowmeter of claim 1, further comprising a funnel that directs the flow of urine into a reservoir space of the flow chamber.

4. The portable handheld uroflowmeter of claim 3, wherein the funnel produces a smooth flow of urine into the flow chamber.

5. The portable handheld uroflowmeter of claim 1, wherein:
   the flow chamber defines an inlet that receives the flow of urine; and
   the outlet evacuates urine from the flow chamber at a predetermined rate.

6. The portable handheld uroflowmeter of claim 5, wherein the outlet is defined by a T-shaped slot.

7. The portable handheld uroflowmeter of claim 5, further comprising electronics that determine a fill volume of the flow chamber using the movement of the magnet.

8. The portable handheld uroflowmeter of claim 5, further comprising a funnel at least partially received within the inlet and having one or more contoured surfaces.

9. The portable handheld uroflowmeter of claim 1, the buoyant float further comprising a structural member adapted to prevent the flow of urine from overrunning a top of the buoyant float.

10. The portable handheld uroflowmeter of claim 1, wherein the handle is cantilevered and extending away from the flow chamber.

11. A portable handheld uroflowmeter comprising:
    a flow chamber defining a reservoir space, the reservoir space having an inlet configured to receive a direct flow of urine and an outlet, positioned away from the inlet and defined in the flow chamber, the outlet configured to continuously empty the reservoir space as the urine is received;
    a handle detachably coupled to the flow chamber and configured to selectively position the flow chamber to receive the flow of urine;
    a funnel at least partially received within the inlet and having one or more contoured surfaces;
    a buoyant float within the flow chamber, the buoyant float positionable according to the level of urine within the flow chamber; and
    electronics operatively coupled to the buoyant float and associated with the flow chamber responsive to the flow of urine.

12. The portable handheld uroflowmeter of claim 11, where the electronics comprise a sensor associated with the flow chamber that detects a parameter of urine received in the chamber.

13. The portable handheld uroflowmeter of claim 12, wherein:
    the uroflowmeter further comprises a magnet positionally responsive to the flow of urine; and
    the sensor further detects a movement of the magnet.

14. The portable handheld uroflowmeter of claim 11, where the flow chamber comprises contoured side walls.

15. The portable handheld uroflowmeter of claim 11, wherein the outlet is a triangular-shaped slot.

16. The portable handheld uroflowmeter of claim 15, where the triangular-shaped slot empties the reservoir space at an increasing rate as the reservoir space fills with urine.

17. The portable handheld uroflowmeter of claim 11, wherein the handle houses the electronics.

18. The portable handheld uroflowmeter of claim 11, wherein the handle is cantilevered and extending away from the flow chamber.

* * * * *